(12) United States Patent
Willett et al.

(10) Patent No.: US 10,307,166 B2
(45) Date of Patent: Jun. 4, 2019

(54) MANUAL SURGICAL LIGATION CLIP APPLIER

(71) Applicant: TELEFLEX MEDICAL INCORPORATED, Research Triangle Park, NC (US)

(72) Inventors: Lynn Willett, Raleigh, NC (US); Philip Schmidt, Roxboro, NC (US); Dan Monahan, Raleigh, NC (US); Adam Lehman, Northford, CT (US); Leland Ray Adams, Ansonia, CT (US); Paul Whiting, Wake Forest, NC (US); Salvatore Castro, Raleigh, NC (US); Alan Bachman, Milford, CT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 199 days.

(21) Appl. No.: 15/283,991

(22) Filed: Oct. 3, 2016

(65) Prior Publication Data

US 2017/0020530 A1    Jan. 26, 2017

Related U.S. Application Data

(62) Division of application No. 13/618,858, filed on Sep. 14, 2012, now Pat. No. 9,456,824.
(Continued)

(51) Int. Cl.
*A61B 17/12* (2006.01)
*A61B 17/128* (2006.01)
(Continued)

(52) U.S. Cl.
CPC ............ *A61B 17/12* (2013.01); *A61B 17/128* (2013.01); *A61B 17/1222* (2013.01);
(Continued)

(58) Field of Classification Search
CPC ............ A61B 17/068; A61B 17/0682; A61B 17/0684; A61B 17/0686; A61B 17/122;
(Continued)

(56) References Cited

U.S. PATENT DOCUMENTS 125,311 A    4/1872    Lucas
717,367 A    12/1902   Ellis
(Continued)

FOREIGN PATENT DOCUMENTS

DE    202010008714 U1    12/2010
EP       0105414 A1       4/1984
(Continued)

OTHER PUBLICATIONS

Chris H. Luebkeman and Donald Peting; Architectronics the Science of Architecture "What is a Moment",1995; printed from; http://web.mit.edu/4.441/1_lectures/1_lecture5/1_lecture5.html.

*Primary Examiner* — Robert A Lynch
(74) *Attorney, Agent, or Firm* — Baker & Hostetler LLP

(57) ABSTRACT

A ligation clip applier is provided. The clip applier includes: a pair of jaws; a distal clevis tube to which the jaws are pivotally mounted; a proximal clevis tube located behind the distal clevis tube, wherein the distal clevis tube and the proximal clevis tubes move axially with respect to each other; a clip lock actuator fixed to one of the proximal and distal clevis tubes; and a distal pushrod extending through the distal and proximal clevis tubes and forming a camming connection with the jaws configured to close and move the jaws toward a proximal direction toward the clip lock actuator when the distal pushrod is moved in the proximal direction. A method for applying a clip on a vessel is disclosed.

14 Claims, 99 Drawing Sheets

Related U.S. Application Data

(60) Provisional application No. 61/535,190, filed on Sep. 15, 2011.

(51) Int. Cl.
*A61B 90/00* (2016.01)
*A61B 17/122* (2006.01)

(52) U.S. Cl.
CPC ............ *A61B 90/03* (2016.02); *A61B 17/122* (2013.01); *A61B 17/1285* (2013.01); *A61B 2017/12004* (2013.01)

(58) Field of Classification Search
CPC .............. A61B 17/128; A61B 17/1285; A61B 2017/00668; A61B 2017/2933; A61B 2017/2936
See application file for complete search history.

(56) References Cited

U.S. PATENT DOCUMENTS

| | | |
|---|---|---|
| 2,277,139 A | 3/1942 | Niemand et al. |
| 2,931,086 A | 4/1960 | Martin et al. |
| 2,968,041 A | 1/1961 | Skold et al. |
| 3,234,636 A | 2/1966 | Brown et al. |
| 3,274,658 A | 9/1966 | Edward et al. |
| 3,279,479 A | 10/1966 | Solomon et al. |
| 3,326,216 A | 6/1967 | Wood |
| 3,463,156 A | 8/1969 | Mcdermott et al. |
| 3,616,497 A | 11/1971 | Esposito et al. |
| 3,733,656 A | 5/1973 | Stalder |
| 3,827,438 A | 8/1974 | Kees, Jr. |
| 4,038,987 A | 8/1977 | Komiya |
| 4,140,125 A | 2/1979 | Smith |
| 4,296,751 A | 10/1981 | Blake, III et al. |
| 4,337,774 A | 7/1982 | Perlin |
| 4,372,316 A | 2/1983 | Blake, III et al. |
| 4,408,603 A | 10/1983 | Blake, III et al. |
| 4,414,721 A | 11/1983 | Hufnagel |
| 4,458,682 A | 7/1984 | Cerwin |
| 4,487,205 A | 12/1984 | Di Giovanni et al. |
| 4,493,495 A | 1/1985 | Linn |
| 4,514,885 A | 5/1985 | Delahousse et al. |
| 4,550,729 A | 11/1985 | Cerwin et al. |
| 4,579,118 A | 4/1986 | Failla |
| 4,586,501 A | 5/1986 | Claracq |
| 4,590,937 A | 5/1986 | Deniega |
| 4,638,804 A | 1/1987 | Jewusiak |
| 4,658,822 A | 4/1987 | Kees, Jr. |
| 4,660,558 A | 4/1987 | Kees, Jr. |
| 4,671,281 A | 6/1987 | Beroff et al. |
| 4,722,466 A | 2/1988 | Hsu |
| 4,763,390 A | 8/1988 | Rooz |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,834,096 A | 5/1989 | Oh et al. |
| 4,835,824 A | 6/1989 | Durham et al. |
| 4,932,955 A | 6/1990 | Merz et al. |
| 4,942,886 A | 7/1990 | Timmons |
| 4,966,603 A | 10/1990 | Focelle et al. |
| 5,015,249 A | 5/1991 | Nakao et al. |
| 5,030,226 A | 7/1991 | Green et al. |
| 5,046,611 A | 9/1991 | Oh |
| 5,049,153 A | 9/1991 | Nakao et al. |
| 5,053,045 A | 10/1991 | Schmidt et al. |
| 5,062,846 A | 11/1991 | Oh et al. |
| 5,067,958 A | 11/1991 | Sandhaus |
| 5,074,870 A | 12/1991 | von Zeppelin |
| 5,078,731 A | 1/1992 | Hayhurst |
| 5,084,057 A | 1/1992 | Green et al. |
| 5,100,416 A | 3/1992 | Oh et al. |
| 5,100,418 A | 3/1992 | Yoon et al. |
| 5,100,420 A | 3/1992 | Green et al. |
| 5,125,915 A | 6/1992 | Berry et al. |
| 5,129,885 A | 7/1992 | Green et al. |
| 5,156,609 A | 10/1992 | Nakao et al. |
| 5,171,247 A | 12/1992 | Hughett et al. |
| 5,171,249 A | 12/1992 | Stefanchik et al. |
| 5,171,250 A | 12/1992 | Yoon |
| 5,197,970 A | 3/1993 | Green et al. |
| 5,201,416 A | 4/1993 | Taylor |
| 5,219,353 A | 6/1993 | Garvey, III et al. |
| 5,222,961 A | 6/1993 | Nakao et al. |
| 5,232,450 A | 8/1993 | Green et al. |
| 5,285,556 A | 2/1994 | Shorin et al. |
| 5,289,963 A | 3/1994 | McGarry et al. |
| 5,292,326 A | 3/1994 | Green et al. |
| 5,300,081 A | 4/1994 | Young et al. |
| 5,306,283 A | 4/1994 | Conners |
| 5,308,337 A | 5/1994 | Bingisser |
| 5,354,306 A | 10/1994 | Garvey, III et al. |
| 5,356,064 A | 10/1994 | Green et al. |
| 5,366,458 A | 11/1994 | Korthoff et al. |
| 5,366,459 A | 11/1994 | Yoon |
| 5,378,928 A | 1/1995 | Anderson et al. |
| 5,382,254 A | 1/1995 | McGarry et al. |
| 5,383,881 A | 1/1995 | Green et al. |
| 5,389,102 A | 2/1995 | Green et al. |
| 5,395,381 A | 3/1995 | Green et al. |
| 5,423,831 A | 6/1995 | Nates |
| 5,423,835 A | 6/1995 | Green et al. |
| 5,423,856 A | 6/1995 | Green |
| 5,431,668 A | 7/1995 | Burbank, III et al. |
| 5,437,680 A | 8/1995 | Yoon |
| 5,447,513 A | 9/1995 | Davison et al. |
| 5,456,401 A | 10/1995 | Green et al. |
| 5,462,558 A | 10/1995 | Kolesa et al. |
| 5,464,413 A | 11/1995 | Siska, Jr. et al. |
| 5,464,416 A | 11/1995 | Steckel |
| 5,474,567 A | 12/1995 | Stefanchik et al. |
| 5,474,569 A | 12/1995 | Zinreich et al. |
| 5,474,572 A | 12/1995 | Hayhurst |
| 5,474,732 A | 12/1995 | Korthoff et al. |
| 5,478,003 A | 12/1995 | Green et al. |
| 5,478,353 A | 12/1995 | Yoon |
| 5,480,405 A | 1/1996 | Yoon |
| 5,489,287 A | 2/1996 | Green et al. |
| 5,496,333 A | 3/1996 | Sackier et al. |
| 5,509,920 A | 4/1996 | Phillips et al. |
| 5,514,149 A | 5/1996 | Green et al. |
| 5,523,629 A | 6/1996 | Anderson et al. |
| 5,527,318 A | 6/1996 | McGarry |
| 5,527,319 A | 6/1996 | Green et al. |
| 5,535,510 A | 7/1996 | Anderson et al. |
| 5,542,949 A | 8/1996 | Yoon |
| 5,545,167 A | 8/1996 | Lin |
| 5,573,541 A | 11/1996 | Green et al. |
| 5,575,802 A | 11/1996 | McQuilkin et al. |
| 5,591,178 A | 1/1997 | Green et al. |
| 5,593,414 A | 1/1997 | Shipp et al. |
| 5,601,573 A | 2/1997 | Fogelberg et al. |
| 5,601,574 A | 2/1997 | Stefanchik et al. |
| 5,607,436 A | 3/1997 | Pratt et al. |
| 5,626,592 A | 5/1997 | Phillips et al. |
| 5,632,753 A | 5/1997 | Loeser |
| RE35,525 E | 6/1997 | Stefanchik et al. |
| 5,643,291 A | 7/1997 | Pier et al. |
| 5,645,551 A | 7/1997 | Green et al. |
| 5,645,553 A | 7/1997 | Kolesa et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,700,270 A * | 12/1997 | Peyser et al. ........... A61B 17/10 606/142 |
| 5,700,271 A | 12/1997 | Whitfield et al. |
| 5,709,706 A | 1/1998 | Kienzle et al. |
| 5,713,912 A | 2/1998 | Porter |
| 5,720,756 A | 2/1998 | Green et al. |
| 5,725,537 A | 3/1998 | Green et al. |
| 5,725,538 A | 3/1998 | Green et al. |
| 5,732,921 A | 3/1998 | Lemire |

(56) References Cited

U.S. PATENT DOCUMENTS

| | | | |
|---|---|---|---|
| 5,749,881 | A | 5/1998 | Sackier et al. |
| 5,755,726 | A | 5/1998 | Pratt et al. |
| 5,769,857 | A | 6/1998 | Reztzov et al. |
| 5,772,673 | A | 6/1998 | Cuny et al. |
| 5,776,146 | A | 7/1998 | Sackier et al. |
| 5,776,147 | A | 7/1998 | Dolendo |
| 5,779,718 | A | 7/1998 | Green et al. |
| 5,792,150 | A | 8/1998 | Pratt et al. |
| 5,810,853 | A | 9/1998 | Yoon |
| 5,833,696 | A | 11/1998 | Whitfield et al. |
| 5,833,700 | A | 11/1998 | Fogelberg et al. |
| 5,843,097 | A | 12/1998 | Mayenberger et al. |
| 5,843,101 | A | 12/1998 | Fry |
| 5,858,018 | A | 1/1999 | Shipp et al. |
| 5,908,430 | A | 6/1999 | Appleby |
| 5,913,862 | A | 6/1999 | Ramsey et al. |
| 5,921,991 | A | 7/1999 | Whitehead et al. |
| 5,921,997 | A | 7/1999 | Fogelberg et al. |
| 5,938,667 | A | 8/1999 | Peyser et al. |
| 5,941,890 | A | 8/1999 | Voegele et al. |
| 5,951,574 | A | 9/1999 | Stefanchik et al. |
| 5,984,934 | A | 11/1999 | Ashby et al. |
| 5,993,465 | A | 11/1999 | Shipp et al. |
| RE36,720 | E | 5/2000 | Green et al. |
| 6,088,889 | A | 7/2000 | Luther et al. |
| 6,139,555 | A | 10/2000 | Hart et al. |
| 6,179,850 | B1 | 1/2001 | Goradia |
| 6,206,897 | B1 | 3/2001 | Jamiolkowski et al. |
| 6,210,419 | B1 | 4/2001 | Mayenberger et al. |
| 6,258,105 | B1 | 7/2001 | Hart et al. |
| 6,261,303 | B1 | 7/2001 | Mayenberger et al. |
| 6,269,819 | B1 | 8/2001 | Oz et al. |
| 6,273,253 | B1 | 8/2001 | Forster et al. |
| 6,273,898 | B1 | 8/2001 | Kienzle et al. |
| 6,277,131 | B1 | 8/2001 | Kalikow |
| 6,290,575 | B1 | 9/2001 | Shipp |
| 6,293,956 | B1 | 9/2001 | Crainich et al. |
| 6,350,269 | B1 | 2/2002 | Shipp et al. |
| 6,391,035 | B1 | 5/2002 | Appleby et al. |
| 6,397,439 | B1 | 6/2002 | Langford |
| 6,421,920 | B1 | 7/2002 | Jensen |
| 6,464,710 | B1 | 10/2002 | Foster |
| 6,569,171 | B2 | 5/2003 | Deguillebon et al. |
| 6,599,298 | B1 | 7/2003 | Forster et al. |
| 6,620,184 | B2 | 9/2003 | De Laforcade et al. |
| 6,638,282 | B2 | 10/2003 | Ramsey et al. |
| 6,652,539 | B2 | 11/2003 | Shipp et al. |
| 6,652,545 | B2 | 11/2003 | Shipp et al. |
| 6,699,258 | B1 | 3/2004 | Sadler et al. |
| 6,716,226 | B2 | 4/2004 | Sixto, Jr. et al. |
| 6,743,240 | B2 | 6/2004 | Smith et al. |
| 6,746,461 | B2 | 6/2004 | Fry |
| 6,776,783 | B1 | 8/2004 | Frantzen et al. |
| 6,780,195 | B2 | 8/2004 | Porat |
| 6,824,547 | B2 | 11/2004 | Wilson, Jr. et al. |
| 6,824,548 | B2 | 11/2004 | Smith et al. |
| 6,840,945 | B2 | 1/2005 | Manetakts et al. |
| 6,843,794 | B2 | 1/2005 | Sixto, Jr. et al. |
| 6,863,675 | B2 | 3/2005 | Wilson, Jr. |
| 6,880,699 | B2 | 4/2005 | Gallagher |
| 6,911,033 | B2 | 6/2005 | De Guillebon et al. |
| 7,001,412 | B2 | 2/2006 | Gallagher et al. |
| 7,022,126 | B2 | 4/2006 | De Canniere |
| 7,056,330 | B2 | 6/2006 | Gayton |
| 7,070,602 | B2 | 7/2006 | Smith et al. |
| 7,090,685 | B2 | 8/2006 | Kortenbach et al. |
| 7,131,977 | B2 | 11/2006 | Fowler |
| 7,141,056 | B2 | 11/2006 | Manetakis |
| 7,144,402 | B2 | 12/2006 | Kuester, III |
| 7,175,648 | B2 | 2/2007 | Nakao |
| 7,179,265 | B2 | 2/2007 | Manetakis et al. |
| 7,182,775 | B2 | 2/2007 | de Guillebon et al. |
| 7,207,997 | B2 | 4/2007 | Shipp et al. |
| 7,211,092 | B2 | 5/2007 | Hughett |
| 7,223,272 | B2 | 5/2007 | Francese et al. |
| 7,288,098 | B2 | 10/2007 | Huitema et al. |
| 7,297,149 | B2 | 11/2007 | Vitali et al. |
| 7,326,223 | B2 | 2/2008 | Wilson, Jr. |
| 7,431,724 | B2 | 10/2008 | Manetakis et al. |
| 7,464,712 | B2 | 12/2008 | Oz et al. |
| 7,509,959 | B2 | 3/2009 | Oz et al. |
| 7,572,266 | B2 | 8/2009 | Young et al. |
| 7,582,095 | B2 | 9/2009 | Shipp et al. |
| 7,585,304 | B2 | 9/2009 | Hughett |
| 7,615,058 | B2 | 11/2009 | Sixto, Jr. et al. |
| 7,637,917 | B2 | 12/2009 | Whitfield et al. |
| 7,648,514 | B1 | 1/2010 | Nakao |
| 7,678,125 | B2 | 3/2010 | Shipp |
| 7,686,820 | B2 | 3/2010 | Huitema et al. |
| 7,713,276 | B2 | 5/2010 | Dennis |
| 7,717,926 | B2 | 5/2010 | Whitfield et al. |
| 7,727,247 | B2 | 6/2010 | Kimura et al. |
| 7,731,724 | B2 | 6/2010 | Huitema et al. |
| 7,740,641 | B2 | 6/2010 | Huitema |
| 7,758,596 | B2 | 7/2010 | Oz et al. |
| 7,819,886 | B2 | 10/2010 | Whitfield et al. |
| 7,862,571 | B2 | 1/2011 | Dennis |
| 7,905,890 | B2 | 3/2011 | Whitfield et al. |
| 8,038,686 | B2 | 10/2011 | Huitema et al. |
| 8,075,571 | B2 | 12/2011 | Vitali et al. |
| 8,097,004 | B2 | 1/2012 | Wild |
| 8,114,098 | B2 | 2/2012 | Kimura et al. |
| 8,133,239 | B2 | 3/2012 | Oz et al. |
| 8,172,870 | B2 | 5/2012 | Shipp |
| 8,216,257 | B2 | 7/2012 | Huitema et al. |
| 8,236,012 | B2 | 8/2012 | Molitor et al. |
| 8,246,634 | B2 | 8/2012 | Huitema et al. |
| 8,246,635 | B2 | 8/2012 | Huitema |
| 8,262,679 | B2 | 9/2012 | Nguyen |
| 8,267,944 | B2 | 9/2012 | Sorrentino et al. |
| 8,267,945 | B2 | 9/2012 | Nguyen et al. |
| 8,267,946 | B2 | 9/2012 | Whitfield et al. |
| 8,282,655 | B2 | 10/2012 | Whitfield et al. |
| 8,328,822 | B2 | 12/2012 | Huitema et al. |
| 8,357,171 | B2 | 1/2013 | Whitfield et al. |
| 8,403,945 | B2 | 3/2013 | Whitfield et al. |
| 8,409,222 | B2 | 4/2013 | Whitfield et al. |
| 2001/0005787 | A1 | 6/2001 | Oz et al. |
| 2002/0068945 | A1 | 6/2002 | Sixto, Jr. et al. |
| 2002/0068946 | A1 | 6/2002 | Kortenbach et al. |
| 2002/0111643 | A1 | 8/2002 | Herrmann et al. |
| 2002/0198537 | A1 | 12/2002 | Smith et al. |
| 2002/0198539 | A1 | 12/2002 | Sixto, Jr. et al. |
| 2003/0014060 | A1 | 1/2003 | Wilson, Jr. et al. |
| 2004/0097971 | A1 | 5/2004 | Hughett |
| 2004/0193185 | A1 | 9/2004 | McBrayer |
| 2004/0193186 | A1 | 9/2004 | Kortenbach et al. |
| 2005/0049616 | A1 | 3/2005 | Rivera et al. |
| 2005/0125010 | A1 | 6/2005 | Smith et al. |
| 2005/0277951 | A1 | 12/2005 | Smith et al. |
| 2005/0277952 | A1 | 12/2005 | Arp et al. |
| 2005/0277953 | A1 | 12/2005 | Francese et al. |
| 2005/0277954 | A1 | 12/2005 | Smith et al. |
| 2005/0277955 | A1 | 12/2005 | Palmer et al. |
| 2005/0277956 | A1 | 12/2005 | Francese et al. |
| 2006/0064117 | A1 | 3/2006 | Aranyi et al. |
| 2006/0235444 | A1 | 10/2006 | Huitema et al. |
| 2007/0049948 | A1 | 3/2007 | Menn et al. |
| 2007/0049949 | A1 | 3/2007 | Manetakis |
| 2007/0049950 | A1 | 3/2007 | Theroux et al. |
| 2007/0049951 | A1 | 3/2007 | Menn |
| 2007/0191868 | A1 | 8/2007 | Theroux et al. |
| 2008/0004637 | A1 | 1/2008 | Klassen et al. |
| 2008/0004639 | A1 | 1/2008 | Huitema et al. |
| 2008/0027465 | A1 | 1/2008 | Vitali et al. |
| 2008/0207995 | A1 | 8/2008 | Kortenbach et al. |
| 2008/0234703 | A1 | 9/2008 | Cropper et al. |
| 2008/0243145 | A1 | 10/2008 | Whitfield et al. |
| 2009/0240266 | A1 | 9/2009 | Dennis |
| 2010/0057104 | A1 | 3/2010 | Sorrentino et al. |
| 2010/0057106 | A1 | 3/2010 | Sorrentino et al. |
| 2010/0249804 | A1 | 9/2010 | Huitema |
| 2011/0087243 | A1 | 4/2011 | Nguyen et al. |
| 2011/0218555 | A1 | 9/2011 | Huitema |

(56) References Cited

U.S. PATENT DOCUMENTS

| | | |
|---|---|---|
| 2011/0218556 A1 | 9/2011 | Nguyen et al. |
| 2011/0224700 A1 | 9/2011 | Schmidt et al. |
| 2011/0288571 A1 | 11/2011 | Steinhilper et al. |
| 2011/0295291 A1 | 12/2011 | Trivisani |
| 2012/0116420 A1 | 5/2012 | Sorrentino et al. |
| 2012/0143217 A1 | 6/2012 | Oz et al. |

FOREIGN PATENT DOCUMENTS

| | | |
|---|---|---|
| EP | 0122046 A1 | 10/1984 |
| EP | 2361560 A2 | 8/2011 |
| FR | 1212165 A | 3/1960 |
| FR | 1356257 A | 6/1964 |
| JP | 2004500190 A | 1/2004 |
| JP | 2005021587 A | 1/2005 |
| JP | 2008100071 A | 5/2008 |
| JP | 2010172663 A | 8/2010 |
| SE | 1000848 A1 | 2/2012 |
| WO | 9109569 A1 | 7/1991 |
| WO | 1995011620 A3 | 5/1995 |
| WO | 1998000066 A1 | 1/1998 |
| WO | 1999000059 A1 | 1/1999 |
| WO | 2002067789 A1 | 9/2002 |
| WO | 2003017827 A3 | 3/2003 |
| WO | 2003071959 A1 | 9/2003 |
| WO | 2006042076 A3 | 4/2006 |
| WO | 2006042084 A3 | 4/2006 |
| WO | 2006042141 A3 | 4/2006 |
| WO | 2009136397 A3 | 11/2009 |
| WO | 2011044039 A1 | 4/2011 |
| WO | 2011112577 A1 | 9/2011 |
| WO | 2012023890 A1 | 2/2012 |

\* cited by examiner

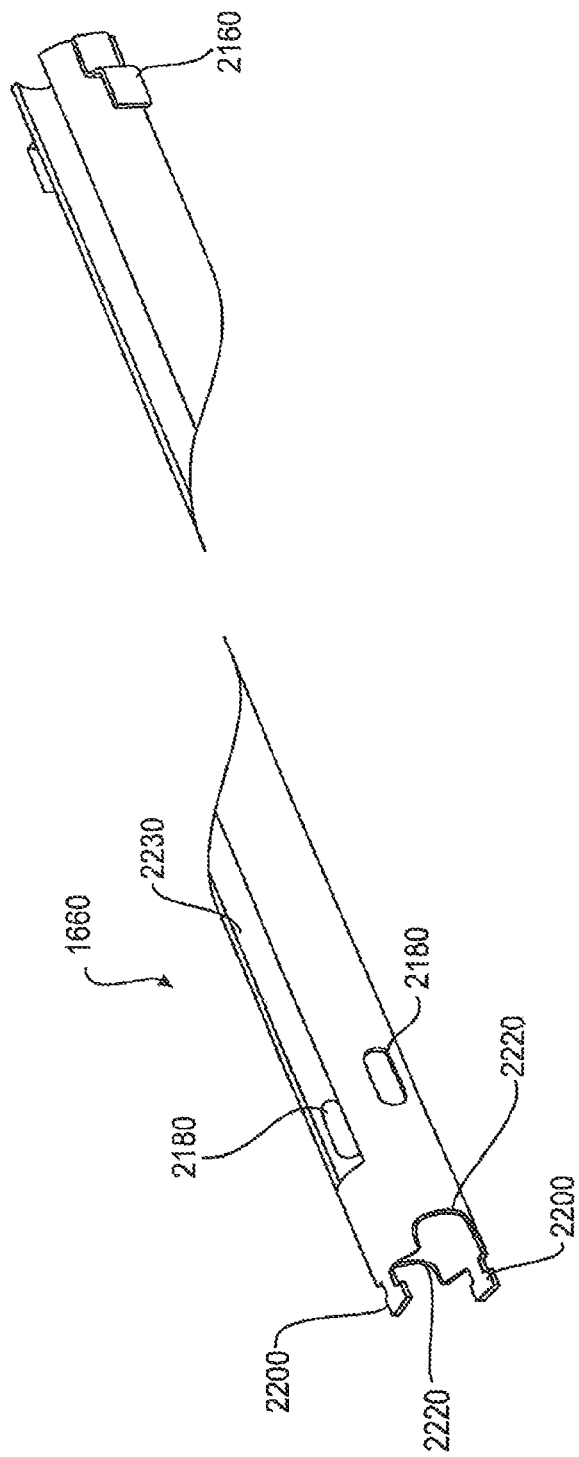

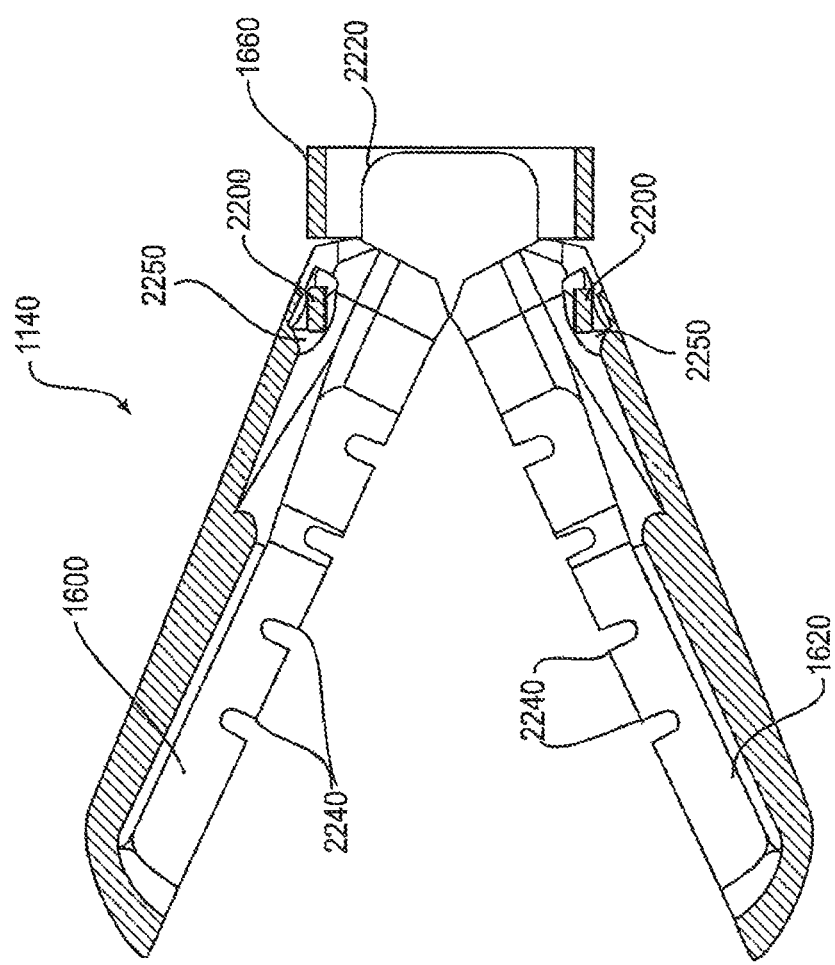

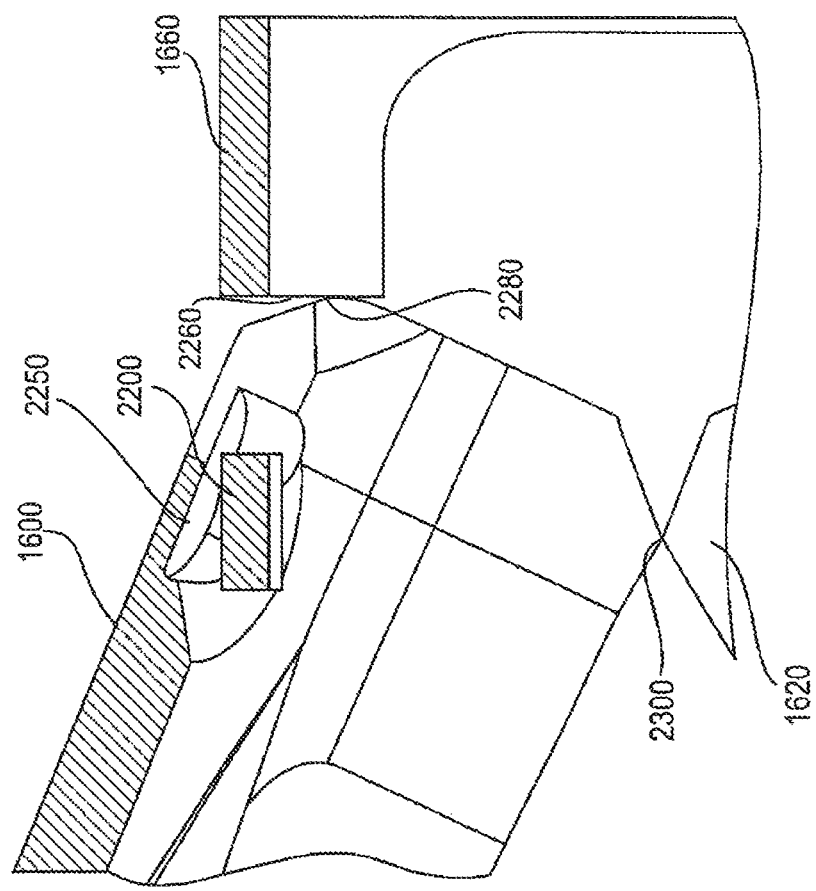

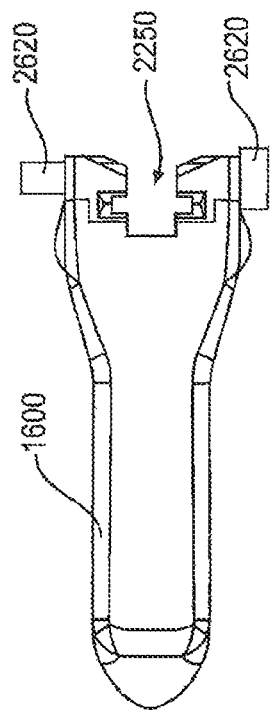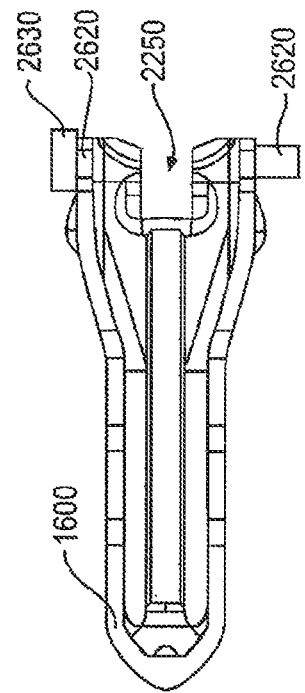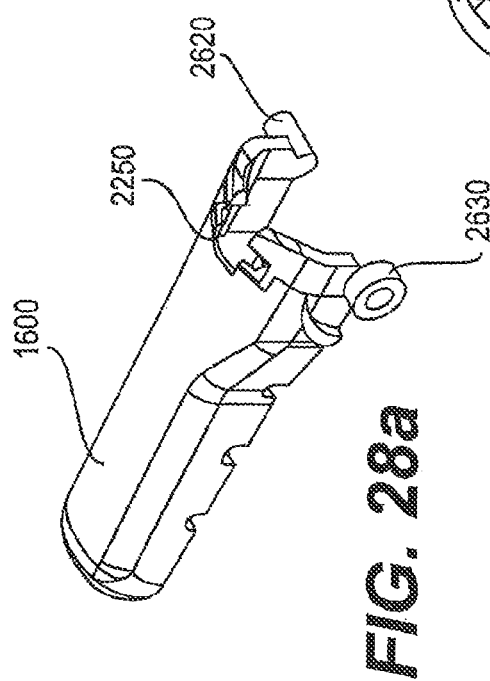

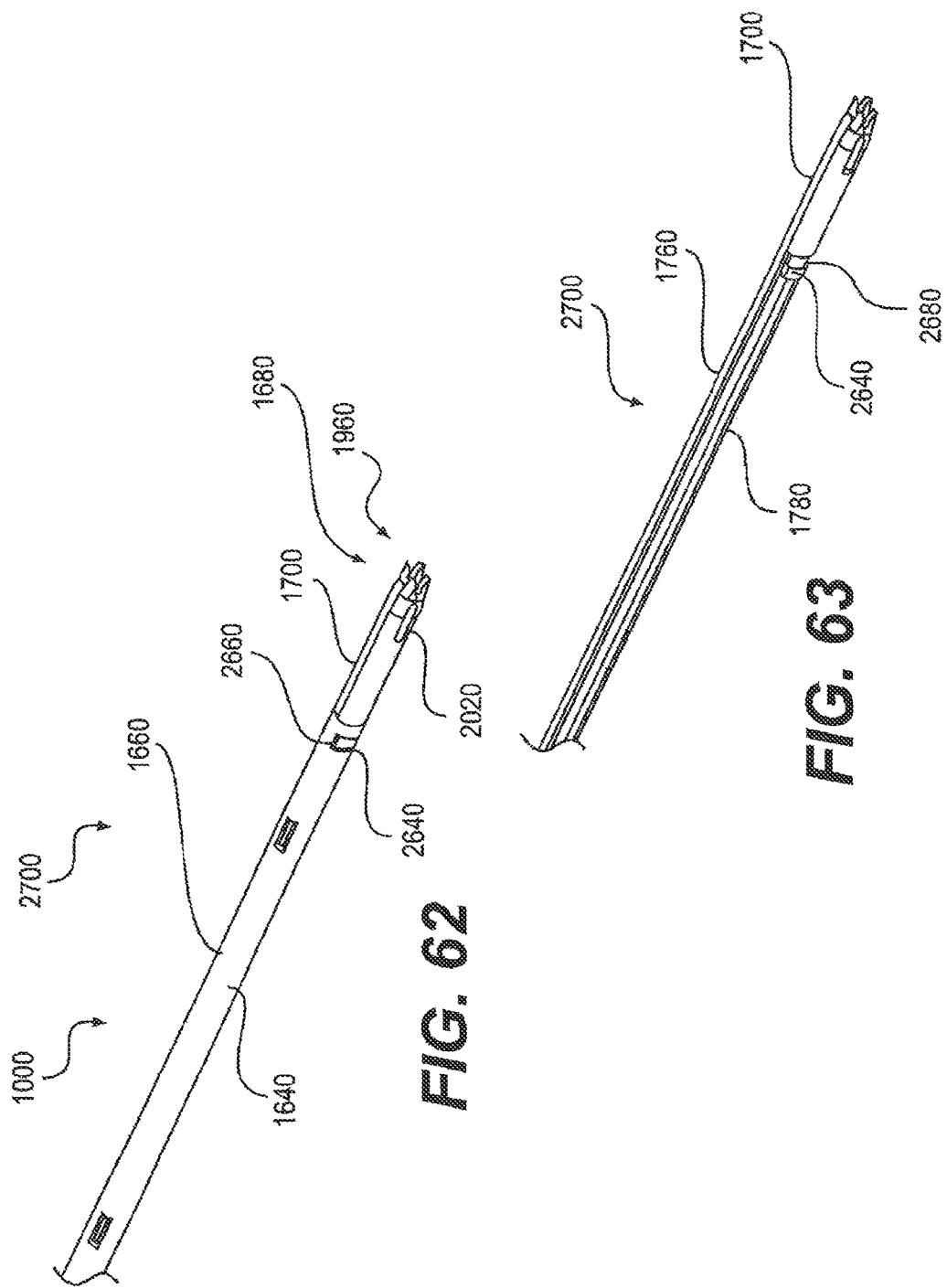

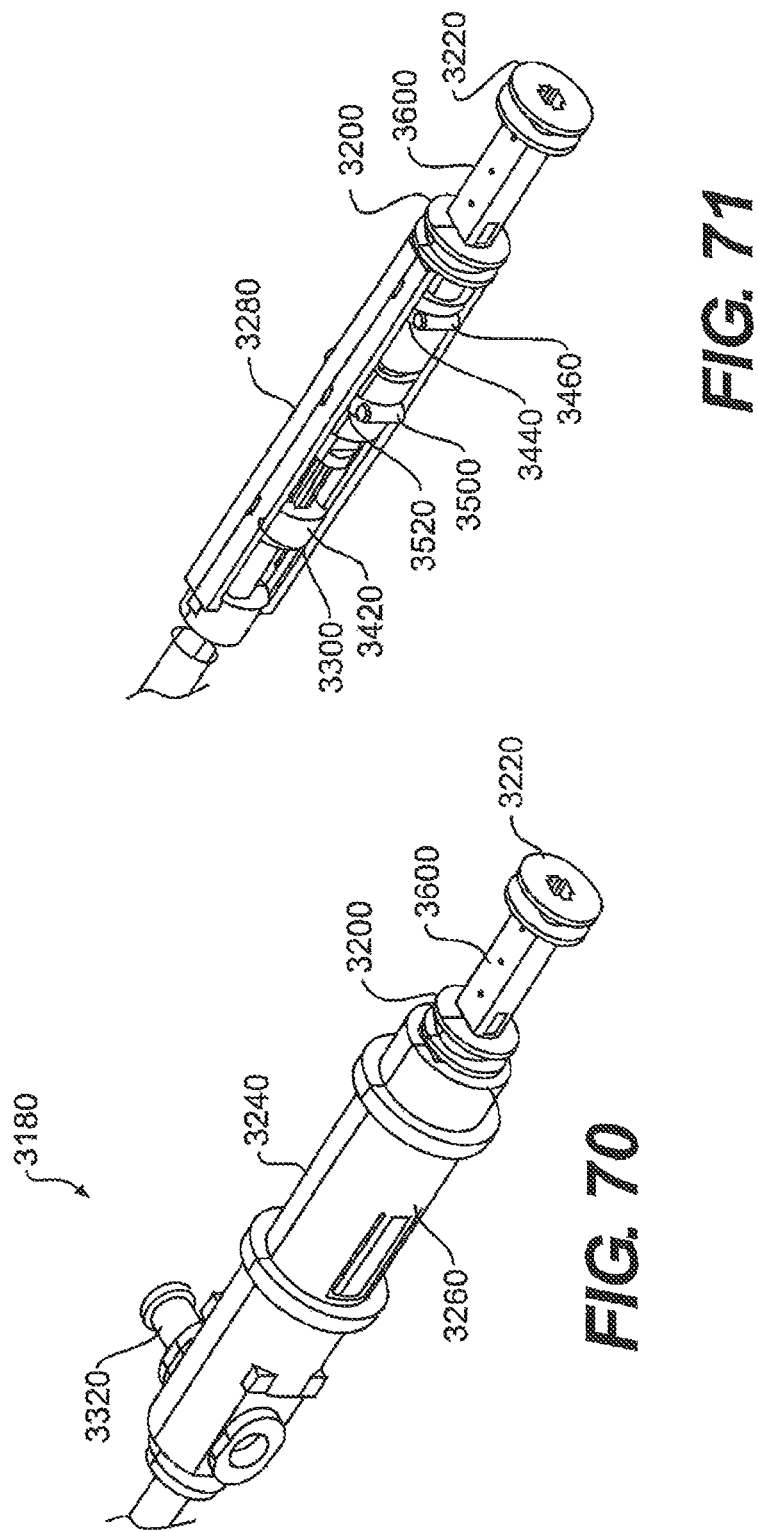

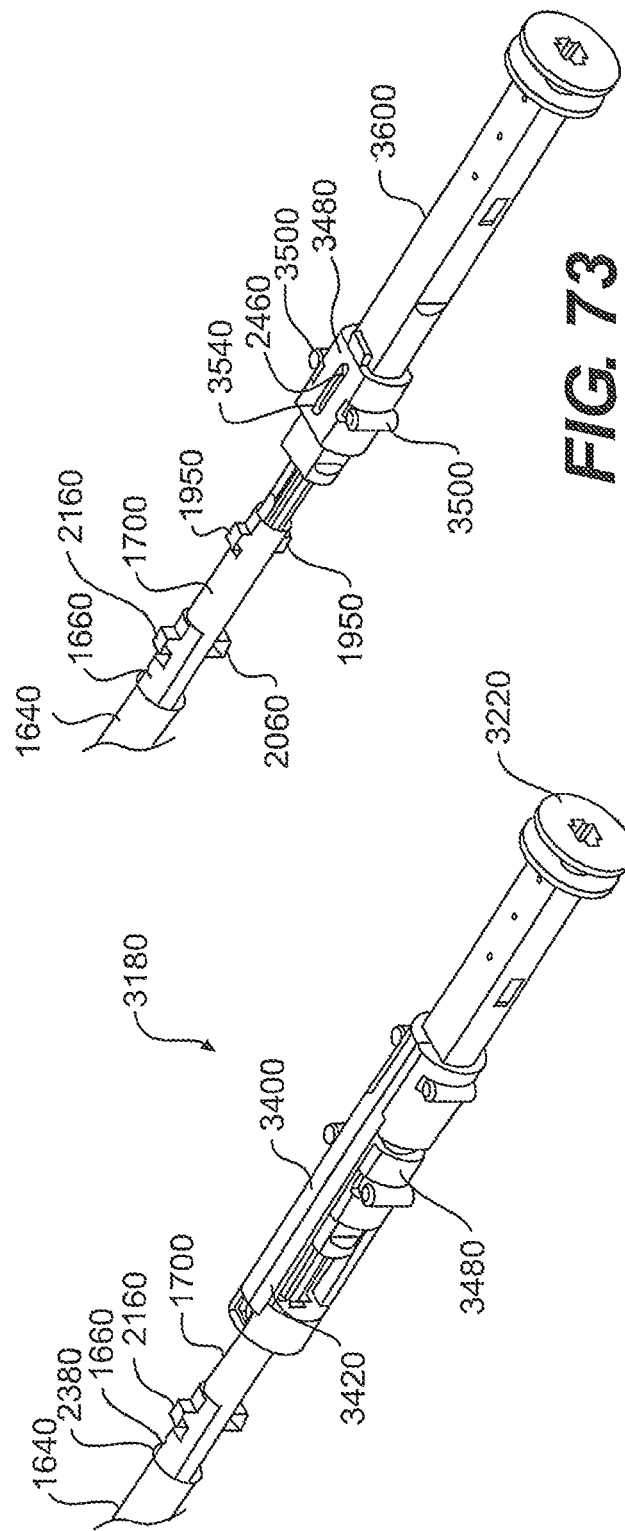

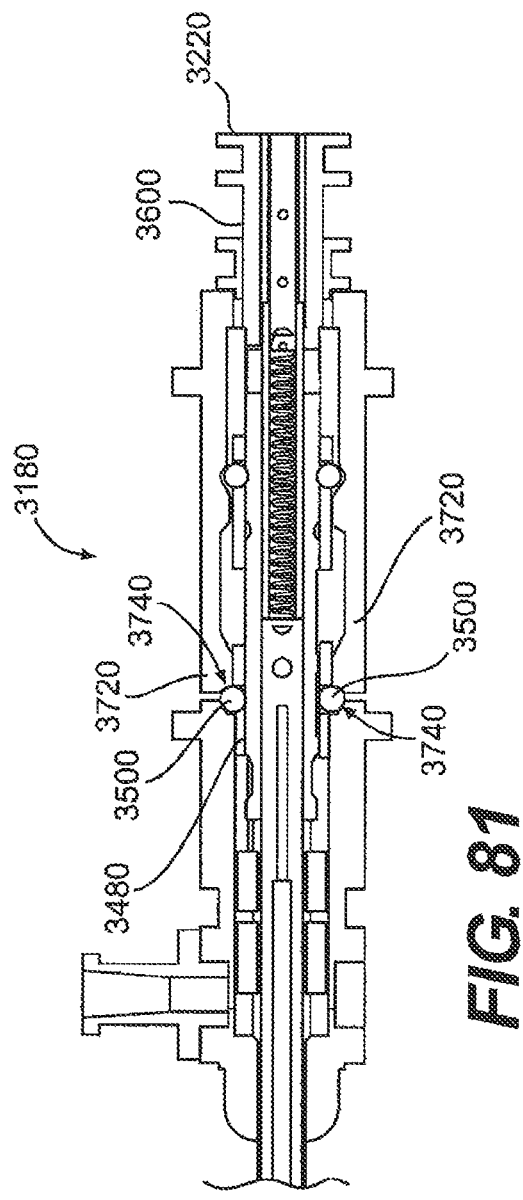
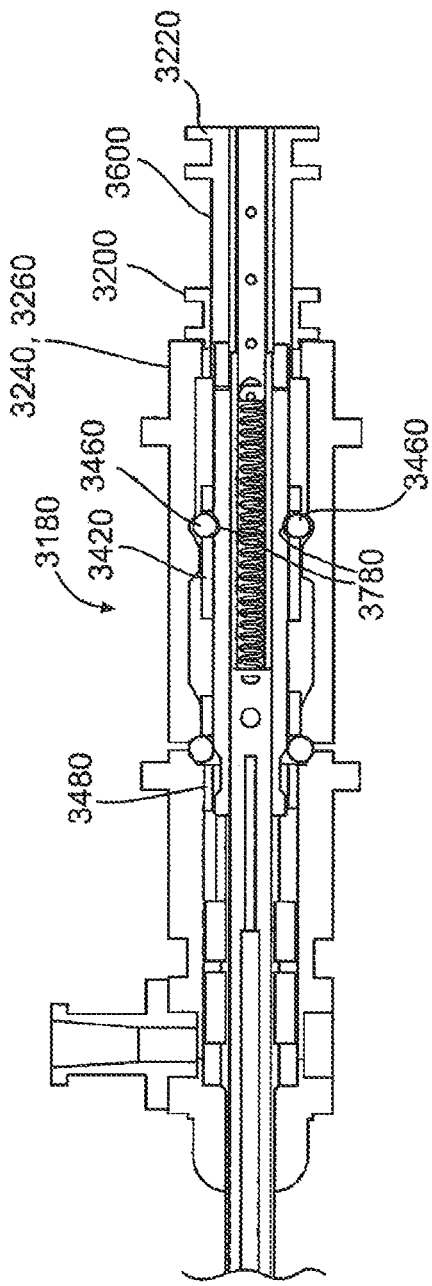
FIG. 81
FIG. 82

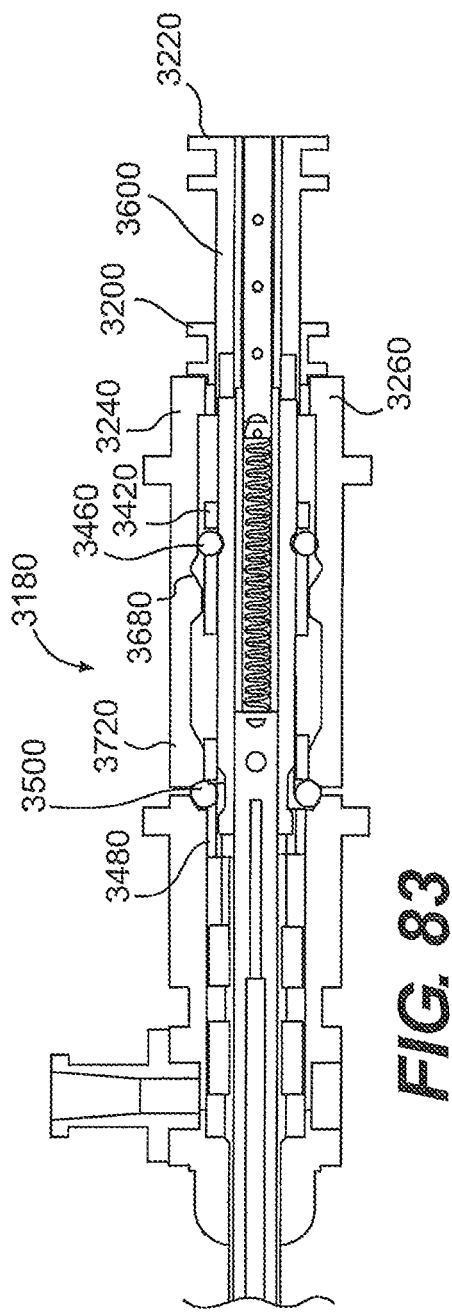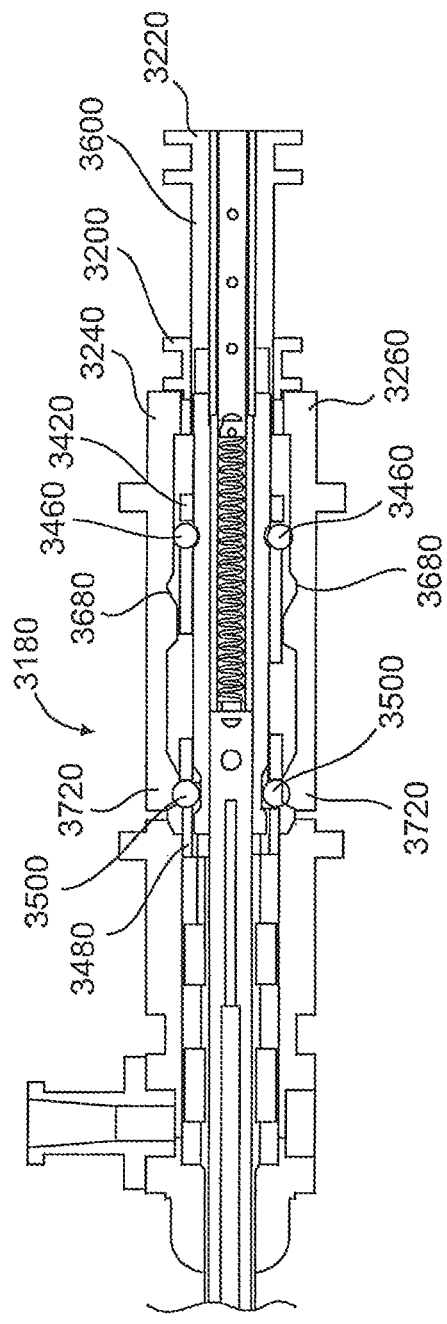

MANUAL SURGICAL LIGATION CLIP APPLIER

CROSS-REFERENCE TO RELATED APPLICATIONS

This application is a Divisional of pending application Ser. No. 13/618,858, filed Sep. 14, 2012, which claims priority to earlier filed U.S. Provisional Application No. 61/535,190, filed on Sep. 15, 2011. This application claims priority to the above mentioned applications and the disclosures of which are hereby incorporated by reference, in their entirety.

FIELD OF THE INVENTION

The present invention relates to medical devices and, in particular, a device for applying surgical clips for ligation of vessels or tissue.

BACKGROUND

Many surgical procedures require vessels or other fluid ducts or tissue conduits and structures to be ligated during the surgical process, such as, for example, veins or arteries in the human body. For example, many surgical procedures require cutting blood vessels, and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. Generally, the clip is left in place after application to the tissue until hemostasis or occlusion occurs.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. But, with the advent of high technology diagnostic techniques using computer tomography (CATSCAN) and magnetic resonance imaging (MRI), metallic clips have been found to interfere with the imaging techniques. To overcome such interference limitations, biocompatible polymers have been increasingly used for surgical clips.

Some well known polymeric clips are disclosed in U.S. Pat. Nos. 4,834,096 and 5,062,846. These plastic clips generally comprise a pair of curved legs joined at their proximal ends with an integral hinge or heel, and a closure or locking mechanism at their distal ends. Another example of a bio-compatible clip is shown in U.S. Pat. No. 4,671,281, which includes a mechanism to be actuated on a proximal end of the clip for causing the distally extending legs of the clip to converge. However this clip is: (i) rudimentary in construction, (ii) does not provide adequate clip closing or clamping strength, (iii) lacks any complex geometry which would adequately retain the clip in a closed position, and further (iv) is too unstable when closed to be safely applied over vessels. Examples of metal hemostatic clips are shown in U.S. Pat. Nos. 3,326,216 and 5,908,430.

In all of the known ligating clips however, there remains a need to improve the effectiveness of clamping about a vessel, while minimizing the damage to the vessel and surrounding tissue. For endoscopic surgical procedures, it is important to use tools and instruments that have the smallest, narrowest profile possible, such as the shafts of a tubular endoscope. Prior art polymeric and metal clips do not lend themselves to deployment through small diameter instrumentation, such as, for example, a ~5 mm endoscope. Known prior art clips can be very wide profile, especially when in the open position prior to closure and ligation, and thus require larger, wider endoscopic instruments and appliers for use in surgery. It is desirable therefore to provide for a surgical ligation clip that has the narrowest profile possible. It may also be desirable to allow for a clip to be opened again after initial closure, which is especially a problem with known surgical clips, such as metal hemostatic clips. Furthermore, prior art polymeric clips involve locking the distal ends of their legs together in order to clamp down on the vessel or structure being ligated. Such closure of a clip having locking parts at its distal end generally causes or requires dissection, removal, or clearance of additional surrounding tissue, in order to allow the clip's locking features to come together, and/or due to actuation of an applier tool surrounding or applied against the distal clip ends, requiring additional time during a surgical procedure and damage to tissue. In other cases, the user may choose not to prepare a path for the locking features and rely on the locking features penetrating through the tissue. In these cases, the locking feature may have difficulty penetrating the tissue or may have difficulty locking after it has penetrated the tissue. This technique may also result in unintended penetration of tissue or vessels.

Therefore it is desirable to provide a clip and a method and/or device for applying the clip which minimizes such dissection of tissue during application. It is further desirable to provide a clip which provides a proper, well-calibrated, reliable clamping force, such that the clip, when closed, is stable around the vessel ligated.

Accordingly, there is a need to provide an improved surgical ligating clip and a method and/or device for applying the clip, where the clip serves to reliably secure the tissue or vessel engaged by the clip, while robustly remaining attached to the vessel with a minimum level of damage to tissue.

SUMMARY OF THE INVENTION

The invention provides, in one or more embodiments, a surgical ligation clip and a device and/or a method of applying the clip to a vessel or tissue. The device may contain a plurality of claims and may apply a first clip to a vessel or tissue and advance a second clip contained in the applier to an applying position.

In another aspect of the invention, a method of applying a surgical ligation clip includes positioning the clip in an open position proximate an inner anatomical body vessel, the clip having first and second legs each extending along a longitudinal axis of the clip and having proximal and distal end portions with respect to said longitudinal axis, a clip hinge means joining the first and second legs at a point on their respective proximal end portions, the first and second legs each having inner clamping surface means between the clip hinge and the distal end portions of said first and second legs, the clamping surface means being apposed when the clip is in a fully closed position, and a locking means for biasing the legs closed extending proximal to the clip hinge means. An external force is applied substantially along the longitudinal axis to a proximal end portion of one of the legs which forms a portion of the locking means, to move a body formed as a first part of said locking means from a first position to a second position to provide an abutment force between a curved planar segment abutment portion of said body and a curved surface formed on a second part of said locking means disposed on the first leg to bias the clip in a closed position. The method may further include moving the clip through an instrument prior to positioning the clip proximate the vessel, and may also further include that a portion of the instrument opens the clip from a closed position to an open position.

In some embodiments, a ligation clip applier is provided. The applier includes: a pair of jaws; a distal clevis tube to which the jaws are pivotally mounted; a proximal clevis tube located behind the distal clevis tube, wherein the distal clevis tube and the proximal clevis tubes move axially with respect to each other; a clip lock actuator fixed to one of the proximal and distal clevis tubes; and a distal pushrod extending through the distal and proximal clevis tubes and forming a camming connection with the jaws configured to close and move the jaws toward a proximal direction toward the clip lock actuator when the distal pushrod is moved in the proximal direction.

A method of applying a clip on a vessel is provided. The method may include: retaining a clip in a pair of jaws by inclined surfaces on a distal portion on each leg of the clip with a corresponding inclined surfaces on the jaws; moving a distal pushrod in a proximal direction; sliding projections along a slot in at least one jaw to rotate the at least one jaw to a closed position; and moving the legs of the clip by closing the jaws.

In some embodiments, a ligation clip applier is provided. The applier may include: means for pinching; a distal clevis tube to which the means for pinching are pivotally mounted; a proximal clevis tube located behind the distal clevis tube, wherein the distal clevis tube and the proximal clevis tubes move axially with respect to each other; means for locking a clip fixed to one of the proximal and distal clevis tubes; and means for moving the means for pinching extending through the distal and proximal clevis tubes and forming a camming connection with the means for pinching configured to close and move the means for pinching toward a proximal direction toward the means for locking a clip when the means for moving the means for pinching is moved in the proximal direction.

The applier is a manually loaded instrument used to deploy proximal locking polymeric ligation clips. The manual applier will load/apply a single clip at a time. The applier is an endoscopic instrument suitable for use in laparoscopic surgery applications.

The polymeric clips will be positioned in clip cartridges. The clips will then be loaded into the applier manually by pressing the distal end of the applier down on the end of the clip. The will be guided by features on the cartridge and will grab the clip in the clip catch mechanism internal to the applier. When the applier is pulled away from the cartridge the clip will release from the cartridge and stay internal to the applier. A clip indicator internal to the applier will indicate that a clip is present at the proximal end of the applier shaft. This will allow the user to know a clip is present prior to and during insertion/manipulation of the applier.

The jaws will be able to actuate without disturbing the loaded clip. This allows the jaws to be used in the dissection and grasping of tissue around the vessel being ligated if necessary.

In a first embodiment of the invention; the jaws of the applier will clamp over the vessel to flatten the section to be ligated. The clip is opened internally in the applier by a set of wedges during clip load. The clip is then positioned over the vessel and subsequently closed with actuation of the wedges and catch mechanism. Once closed, a punch mechanism will engage the locking feature to maintain the clamping pressure of the clip. The jaws then will open allowing the ligated vessel and clip to clear the applier jaws.

In a seconded embodiment of the invention; the clip is positioned over the vessel with actuation of the wedge and catch mechanism and is subsequently closed when a punch mechanism is engaged with the locking feature on the clip. The features of the clip lock cause the legs of the clip to close and once fully locked the clip maintains the clamping pressure on the vessel.

Each of the distal end actuations are accomplished through the use of a proximal handle. The handle is made of a housing and rotation knob, which allow for a 360° continuous rotation of the distal end, separate triggers for jaw actuation and clip functions, and a multi stage transmission that allows the distal end to be actuated in the proper sequence for effective clip delivery.

There has thus been outlined, rather broadly, certain embodiments of the invention in order that the detailed description thereof herein may be better understood, and in order that the present contribution to the art may be better appreciated. There are additional embodiments and features of the invention that will be described below.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

BRIEF DESCRIPTION OF THE DRAWINGS

FIG. 12 is a perspective view from the top of the clip shown in FIG. 11a.

FIG. 13 is a side view of the clip shown in FIG. 11a.

FIG. 25 shows an inner tube.

FIG. 26 shows a jaw/inner tube camming.

FIG. 27 shows a jaw/inner tube cam points.

FIGS. 28a, 28b and 28c shows jaws.

FIG. 62 shows a second embodiment—catch tube with wedges and catches.

FIG. 63 shows a second embodiment—catches and wedges.

FIG. 70 shows an assembled multistage transmission.

FIG. 71 shows a transmission outer shell and with the Leur port removed.

FIG. 72 shows a transmission with the jaw actuator links removed.

FIG. 73 shows a transmission with the catch pusher latches and dowels removed.

FIG. 81 shows a cross-section of the transmission where the clip is latched.

FIG. 82 shows a cross-section of the transmission where the wedges return.

FIG. 83 shows a cross-section of the transmission where the connection pins are no longer in the pocket.

FIG. 84 shows a cross-section of the transmission where the punch is unlatched.

FIG. 122 is a partial cutaway view of the jaws of applier.

FIG. 123 is a side view of another clip that may be used in accordance with invention.

FIG. 124 is a side view of the clip shown FIG. 123 and a closed position.

FIG. 125 is a isometric view of the clip illustrated in FIG. 123.

DETAILED DESCRIPTION

Figure 1:
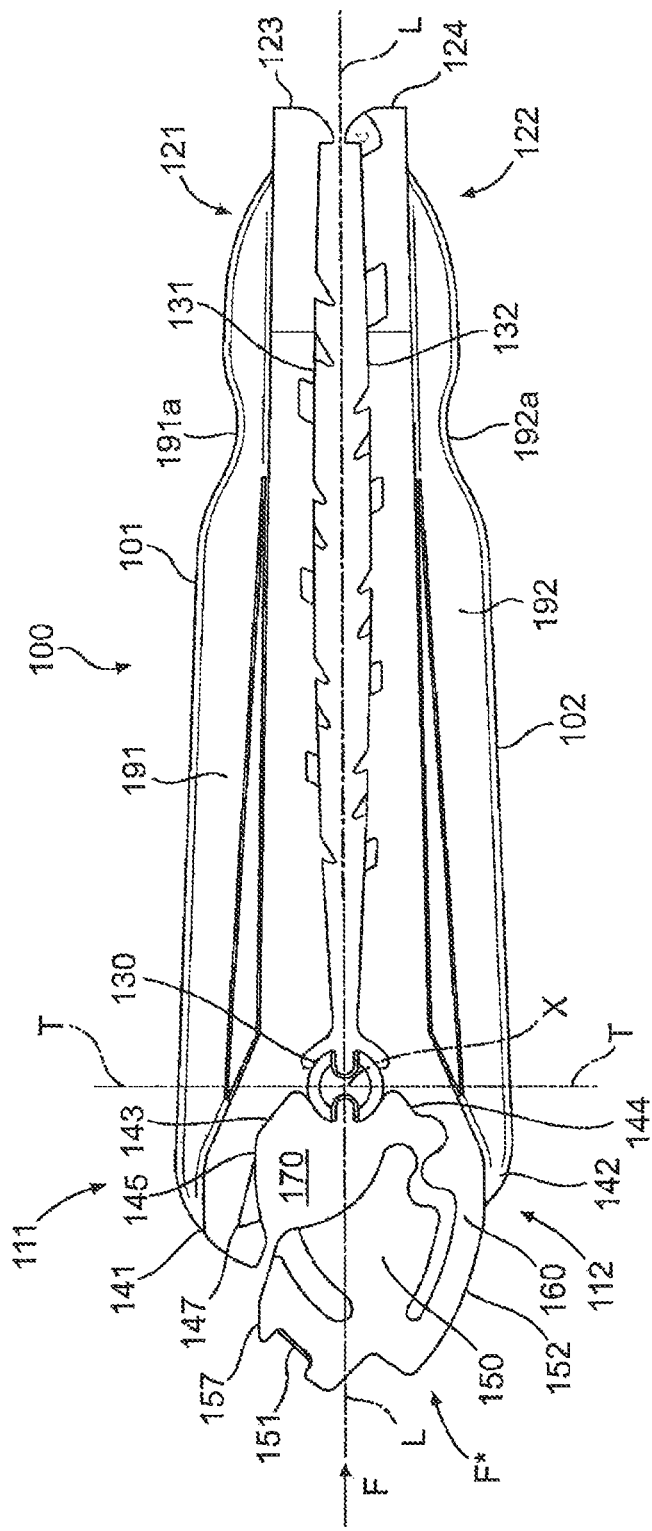
FIG. 1 shows a view of a first embodiment of a surgical ligation clip of the present invention.

The invention will now be described with reference to the drawing figures, in which like parts are referred to with like reference numerals throughout. Clips that may be used in accordance with some embodiments of the invention are described in U.S. provisional patent application No. 61/312, 156, filed on Mar. 9, 2010, and U.S. non-provisional application Ser. No. 13/042,864, filed on Mar. 8, 2011 by Philip Schmidt, et al. the disclosures of which are both incorporated by reference in their entirety.

FIG. 1 shows a view of a first embodiment of a surgical ligation clip 100 in accordance with present invention. The clip 100 defines a longitudinal axis "L" along its longest dimension and includes a first leg 101 and a second leg 102 each extending along the longitudinal axis L and having proximal 111, 112 and distal 121, 122 end portions with respect to said longitudinal axis. As used herein, the term "proximal" shall refer to the portion of the clip referenced herein which is away from the tips of the clip which open, and "distal" shall refer to the portion of the clip at the tips which open, in accordance with the convention that the clip is inserted distal tip first through an instrument towards an anatomical body to be ligated, such that distal generally refers to the direction away from the user or applier of the surgical clip and proximal refers to the direction opposite to distal.

In clip 100, a clip hinge 130 joins the first and second legs 101, 102 at a point on their respective proximal end portions 111, 112, the first and second legs each having respective inner clamping surfaces 131, 132 between the clip hinge 130 and the distal ends 123, 124 of said first and second legs, the clamping surfaces being apposed when the clip is in a fully closed position. As used herein, the term "apposed" when used with regard to the inner clamping surfaces 131, 132 shall mean close to, or nearly in contact with each other, allowing for some small spacing therebetween or a concave radius of curvature for the clamping surfaces, such to allow for a clipped vessel to reside between such apposed surfaces, as is more fully illustrated herein and with respect to the drawing figures. The clip hinge 130 can include a bar or cylindrically shaped body or tube which defines a lateral pivot axis "P" (shown in FIGS. 2b and 2c) about which the legs 101 and 102 pivot as the clip moves from open to closed position and vice versa. A first jaw structure 141 on the first leg 101 extends proximal to a transverse axis "T" which is perpendicular to both the longitudinal axis L and lateral pivot axis P, all intersecting at a point "X" centered on the clip hinge 130, as shown in FIG. 1. As used throughout herein, the term "lateral" shall directionally mean orthogonal to both the directions of the longitudinal axis L and transverse axis T, and parallel to pivot axis P as shown in the figures. The first jaw structure 141 includes a first curved inner surface 143 extending from the clip hinge 130, the first curved inner surface 143 having a complex surface which is oriented at changing angles with respect to, but is generally facing towards, the longitudinal axis L, as shown in FIG. 1. The curved inner surface 143 is therefore substantially concave when viewed from the longitudinal axis (or plane spanning the longitudinal axis and pivot axis). As used herein, the term "substantially concave" shall mean a surface which is concave in overall curvature, but which may include one or more component areas which may have convex segments or protrusions, such as a notch surface or recess for mating thereto. A second jaw structure 142 is on the second leg 102 extending proximal to the transverse axis T and has a second curved inner surface 144 extending from the clip hinge 130. As used herein, the "curved inner surface" can include either a single smoothly curved surface segment, or a series of connected curved or straight planar segments, which, taken together, form an overall generally curving surface. As described herein, the surgical clip of the present invention provides that the jaws 141 and 142 are each substantially proximal to a transverse plane extending through transverse axis T and lateral pivot axis P, thus behind the clip hinge 130, thereby providing a means for actuating the clip legs 101 and 102 and biasing or locking the clip and its mating faces 131, 132 in a closed position, which biasing or locking means can be actuated and/or applied by acting only on the proximal end portions of the clip 100, without having to lock the distal ends 123, 124 to each other or use a clip applier tool which acts on said distal ends 123, 124, thereby obviating the need to dissect tissue around the distal end of the clip as in previously known surgical ligation clips.

As shown in FIG. 1, the means for biasing or locking the clip closed includes a wedge or buttress body 150 which extends from and is connected to the second jaw structure 142 by a first living hinge 160 at a proximal end of said second jaw structure 142, the buttress body 150 having an outer surface 151 at a proximal first end portion thereof, which is also disposed approximately as the proximal end of the clip 100 overall. The first and second jaw structures 141, 142 are spaced on opposite sides of the longitudinal axis L and define a locking space 170 therebetween. The wedge or buttress body 150 is pivotable about the living hinge 160 to move into the locking space 170 such that the outer surface 151 of the proximal first end portion of the buttress body 150 abuts against a proximal portion 145 of the curved inner surface 143 of the first jaw structure 141 to bias the clip in a closed position (as best shown in FIGS. 11a, and 12-14). Although the clip 100 is shown in FIG. 1 in a closed position, this is with the locking means of the first and second jaws 141, 142 and buttress body 150 being in the "unlocked" position as shown in FIGS. 1, 2a, and 3-7. Once the buttress body is in the "locked" position as shown in FIGS. 11a and 12-14, the first and second jaws 141, 142 are urged or spread apart (shown, as an example, by arrows "J1" and "J2" in FIGS. 13a and 14a) by action of surfaces of the wedge/buttress body 150 acting on portions of curved inner surfaces 143, 144, which act as moments about the clip hinge 130 and lateral pivot axis P to urge the legs 101, 102 and its inner clamping surfaces 131, 132 to become more closely apposed to each other, thereby providing additional clamping and closing force over a vessel around which the clip is applied.

A variety of means may be used to actuate the wedge or buttress body 150 from the unlocked position in FIG. 1 to the locked position shown in FIGS. 11a, 12-14. As shown in FIG. 1, an external force, shown, for example, as arrow "F" in FIG. 1, may be applied to a proximal end of the pivoting buttress body 150, in this example the external force F being substantially aligned with the longitudinal axis L. Alternatively, the external force applied may be at a small angle to the longitudinal axis L, such as, for example, a force shown by arrow "F*" shown in FIG. 1. In either case, the applied external force will create a moment about living hinge 160 to pivot the buttress body 150 into the locking space 170. The external force may be applied by an actuating rod or other structural means in an applier instrument, or may be another clip as fed through a multi-clip applier. As one example, the clip 100 may be inserted through an instrument having a bore or channel for receiving the clip 100, through which the clip 100 may travel distally for positioning near a vessel during a surgical procedure. The clip may be inserted in a legs closed position, but with the proximal locking means including buttress body 150 in open, unlocked position. Because the clip 100 can be inserted in such fashion in closed form, the clip forms a narrow profile and can fit in smaller sized surgical instruments, thereby allowing for smaller incisions and tissue dissection or damage during surgery. A rod or other actuating mechanism translating or moveable on the instrument inserting the clip, or a second instrument or second clip used in conjunction with the instrument used for inserting and positioning the clip in place, maybe used to lock the clip by application of an external force on the proximal end portion of the clip as discussed above.

Thus, a method of applying a surgical ligation clip on a vessel in accordance with an embodiment of the invention includes positioning a clip, such as, for example, clip 100, in an open position proximate a vessel, the clip having first and second legs each extending along a longitudinal axis of the clip and having proximal and distal end portions with respect to said longitudinal axis, a clip hinge means joining the first and second legs at a point on their respective proximal end portions, the first and second legs each having inner clamping surface means between the clip hinge and the distal end portions of said first and second legs, the clamping surface means being apposed when the clip is in a fully closed position. A locking means for biasing the legs closed may extend proximal to a transverse axis perpendicular to the longitudinal axis intersecting at a point centered on the clip hinge. The method includes applying an external force to a proximal end portion of the clip or of one of the legs which forms a portion of the locking means, to move a body formed as a first part of said locking means from a first position to a second position to provide an abutment force between said body and a surface formed on a second part of said locking means to bias the clip in a closed position. In the method, an instrument may be used, wherein, in moving the clip through the instrument prior to positioning the clip proximate a vessel, a portion of the instrument opens the clip from a closed position to an open position, such that the legs of the clip open for placement of the clip around a vessel. The locking means may then be applied to the proximal end portion of the clip to move and bias the legs closed and clamp the clip more fully over the vessel.

In FIG. 1, the clamping surfaces appear substantially parallel to each other, oriented, in the clip closed position, substantially or very close to parallel to a plane extending through the longitudinal axis L and lateral pivot axis P. However, in an embodiment of the invention, the inner clamping surfaces 131, 132 may be slightly curved concave when facing said surfaces, such that the surfaces bow away from the longitudinal axis L and straighten slightly when clamping force is applied by action of the locking mechanism of the buttress body 150 acting against jaws 141, 142. This allows for enhanced grasping and occlusion of vessels around which the clip 100 is applied, wherein the clamping force is spread more evenly across the clamping surface.

The living hinge 160 connecting the wedge or buttress body 150 to the second jaw 142 can be integral to the second jaw 142 such that the clip body of second leg 102 proximal to transverse axis T extends as a single unitary structure including the second jaw 142 and entire wedge or buttress body 150. Accordingly, in the wedge or buttress body 150, a lateral beam or curved body 152 connects the living hinge 160 to the rest of the buttress body 150, which beam 152 curves from the living hinge 160 (which is separated by a distance from the longitudinal axis L) towards the longitudinal axis L. As shown in FIG. 1 portions of wedge of buttress body 150 can be oriented on both sides of longitudinal axis L. The pivot axis of living hinge 160 extends in a lateral direction parallel the lateral pivot axis P of the main clip hinge 130.

Figure 12:
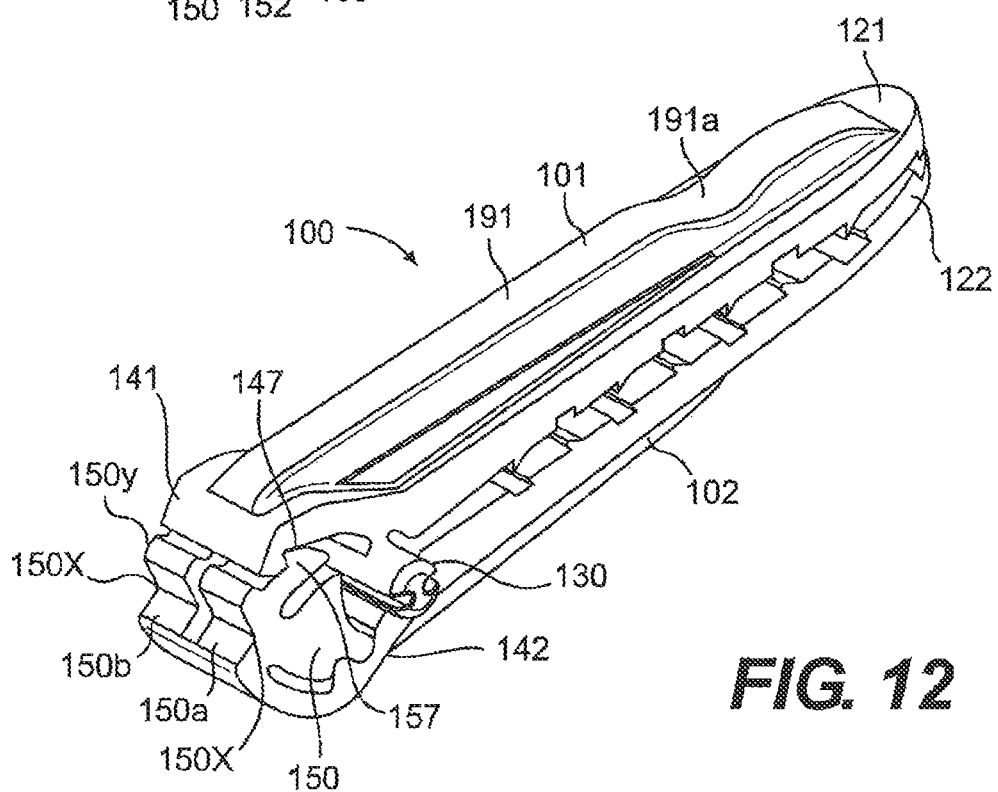
Figure 4:
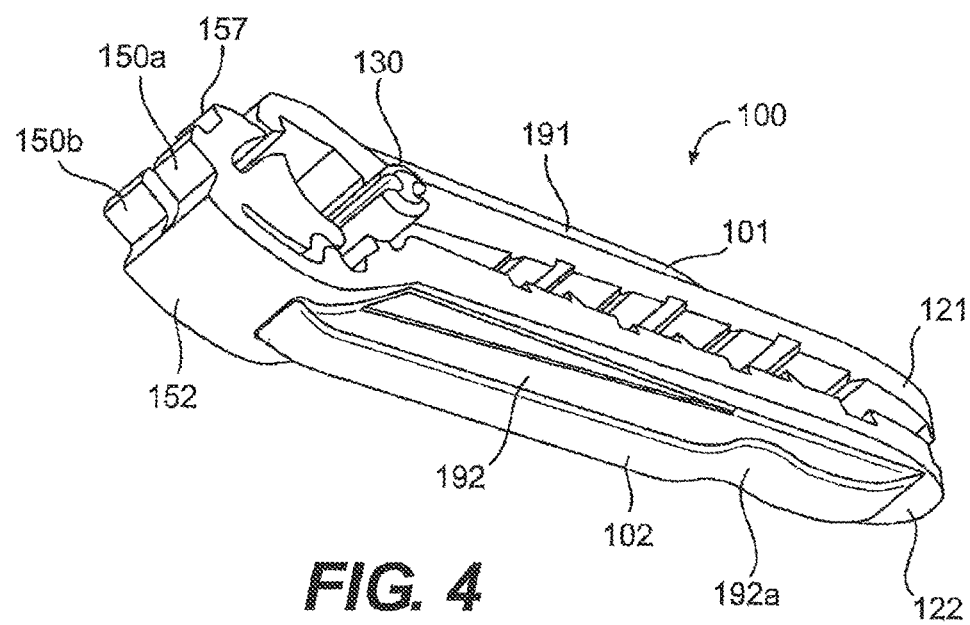
Figure 11A:
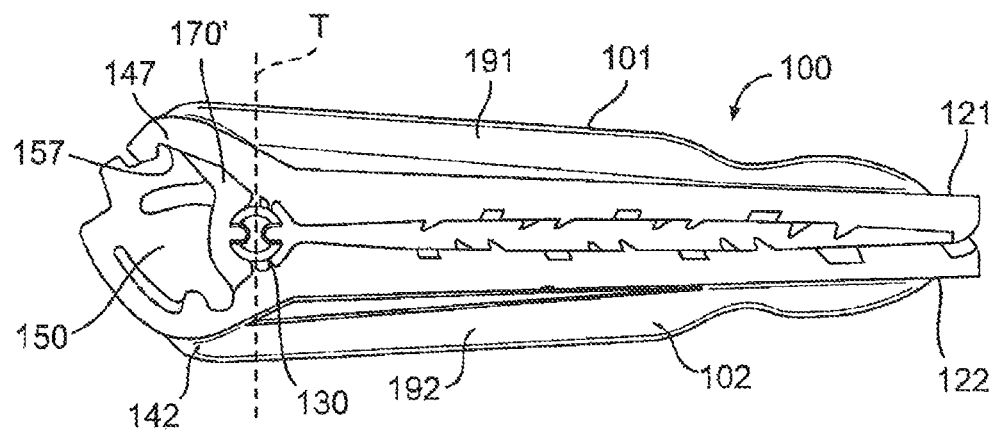
FIGS. 11a, 11b, and 11c show side, top, and bottom views respectively, of the clip shown in FIG. 1, with the proximal locking components in locked position.
Figure 11B:
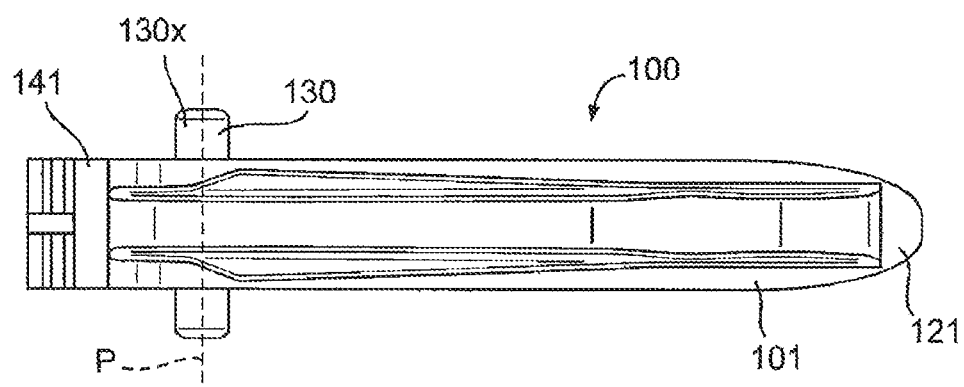
Figure 11C:
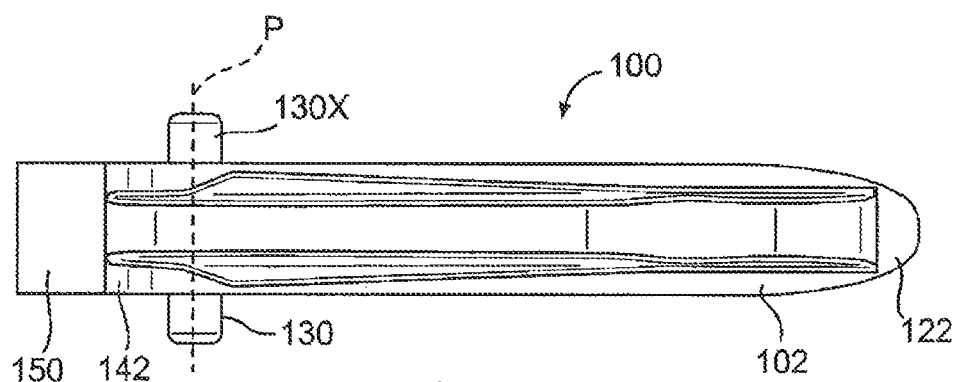
Figure 14:
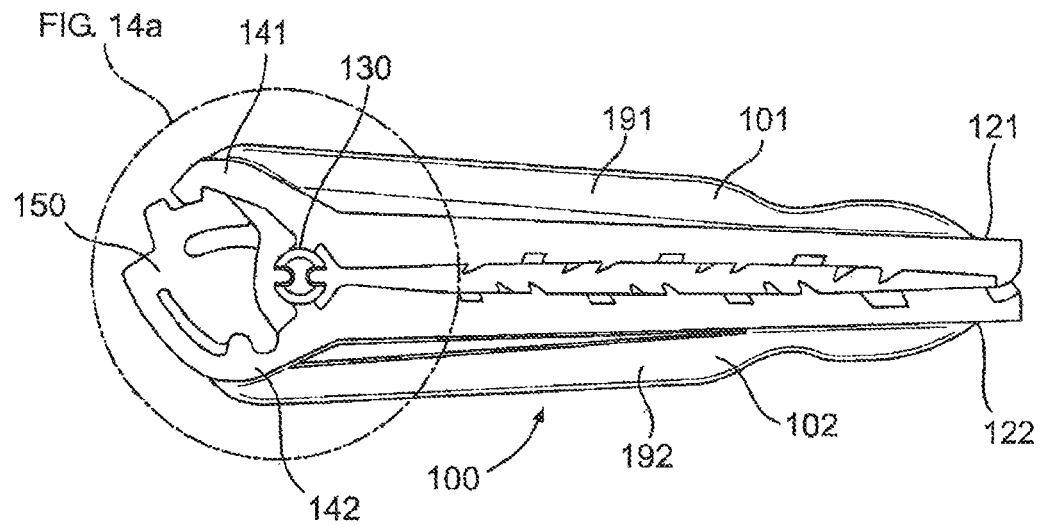
FIG. 14 is a side view of the clip shown in FIG. 11a from the side opposite to that shown in FIG. 13.

The present invention provides, in various embodiments, a locking mechanism cooperating between the buttress body 150 and another portion of the clip. In the clip 100 shown in FIG. 1, the proximal end portion 145 of the curved inner surface 143 of the first jaw structure 141 defines a notch 147 recessed from said curved inner surface 143, and the buttress body 150 defines a detent 157 formed on the outer surface thereof, the detent 157 mating with the notch 147 when the buttress body 150 is pivoted into the locking space 170 to bias the clip in the closed position, as best shown in FIGS. 11a, 12, and 14.

Figure 2A:
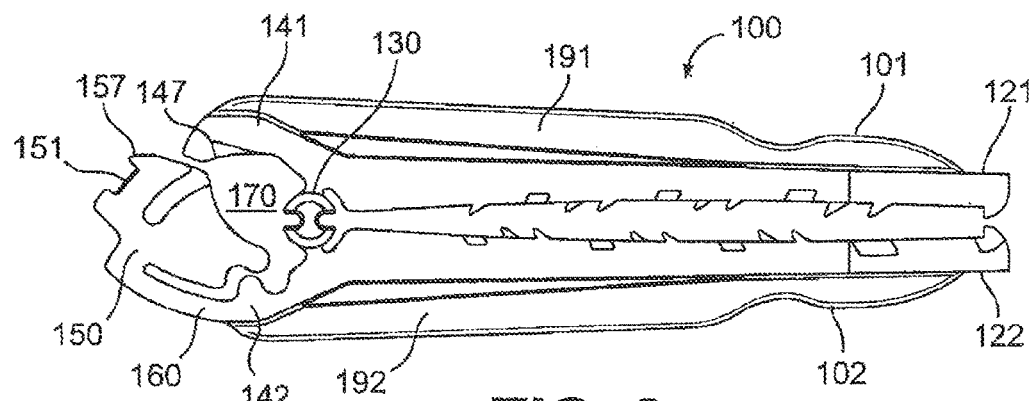
FIGS. 2a, 2b, and 2c show side, top, and bottom views respectively, of the clip shown in FIG. 1.
Figure 2B:
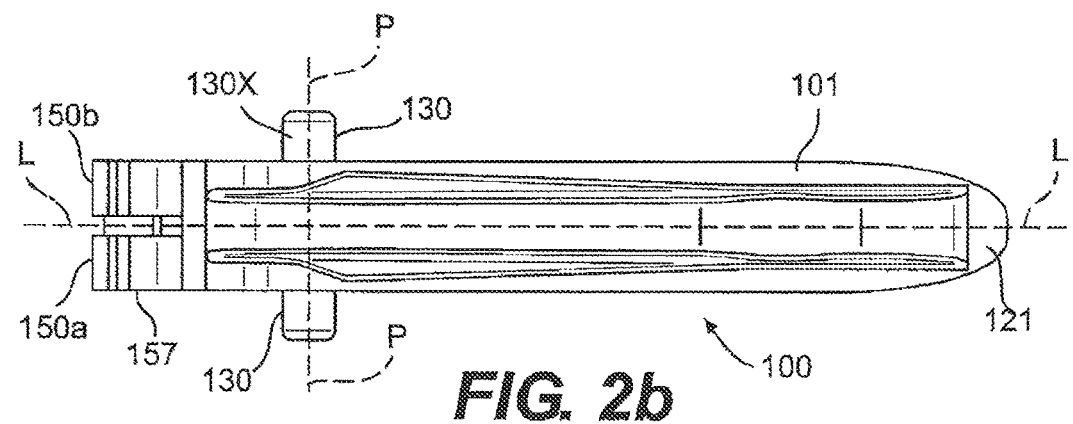
Figure 2C:
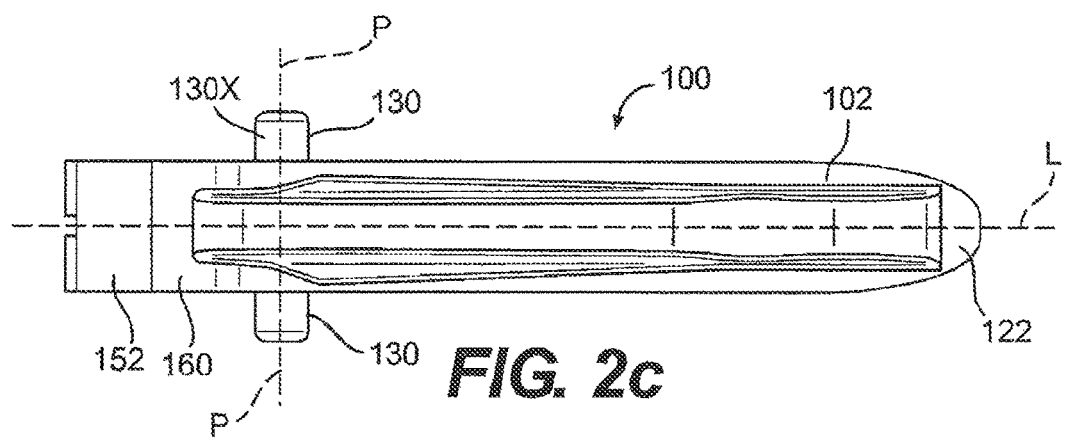
Figure 3:
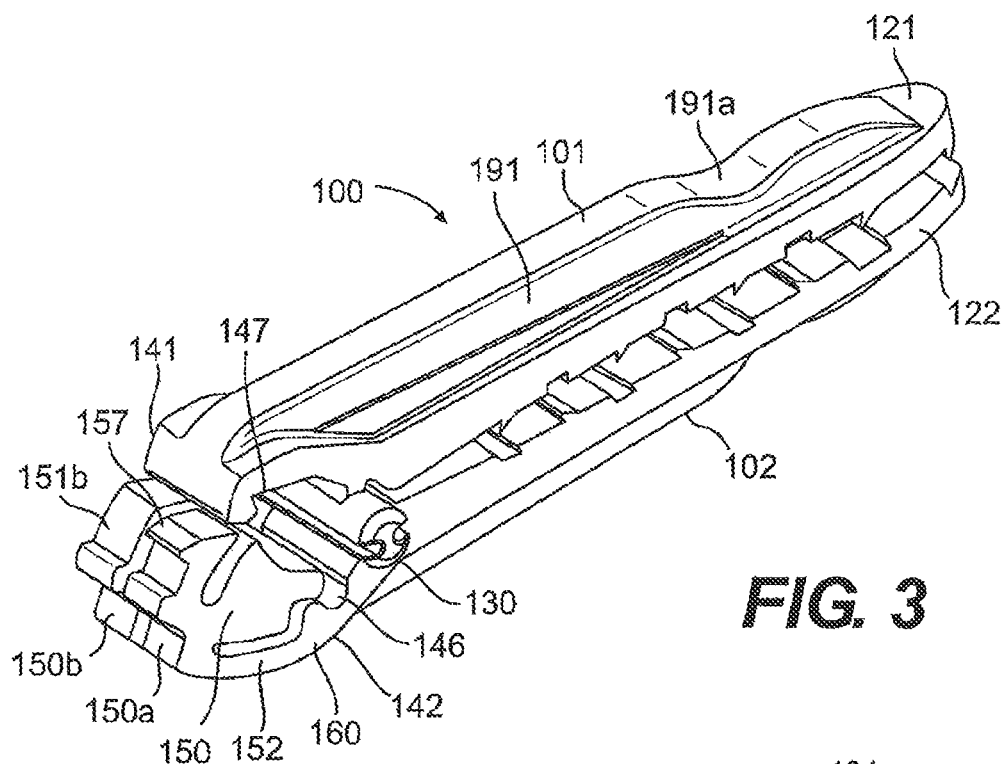
FIGS. 3 and 4 show perspective views of the clip shown in FIG. 1 from a first side.

FIGS. 2a, 2b, and 2c show side, top, and bottom views respectively, of the clip shown in FIG. 1. As shown in FIG.

Figure 7:
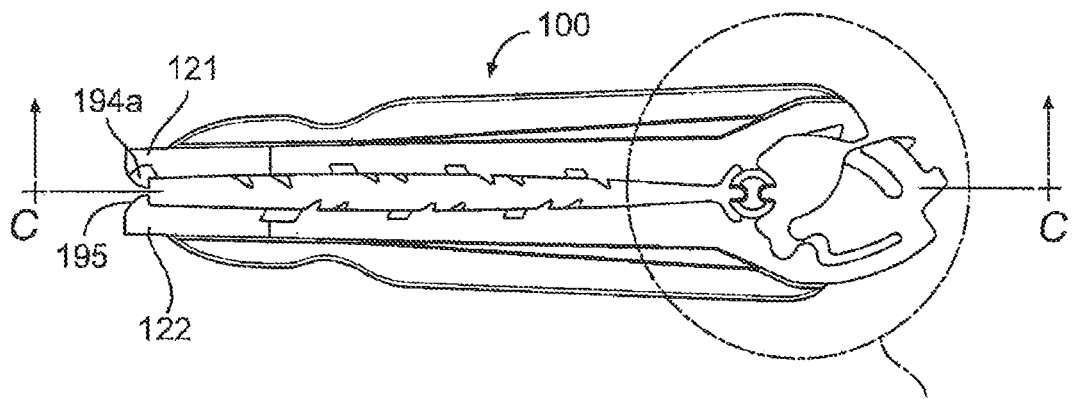
FIG. 7 is another side view of the clip shown in FIG. 1 from the opposite side to that shown in FIG. 6.
Figure 7A:
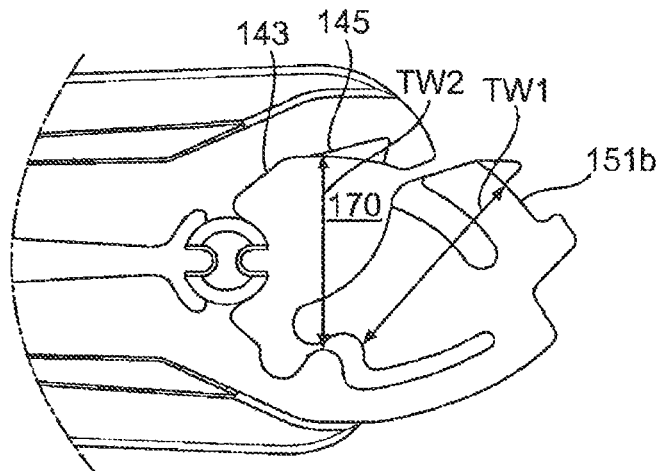
FIG. 7a is a close-up detail view of the portion of the clip shown in FIG. 7 in region "7A" therein.
Figure 7B:
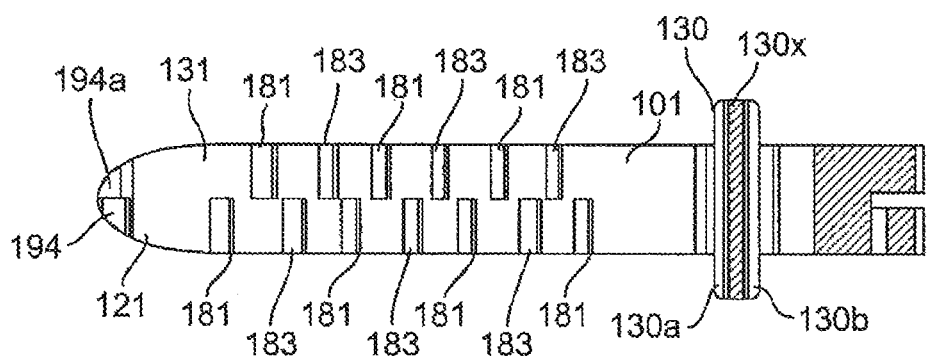
FIG. 7b is a sectional view of the clip shown in FIG. 7 taken along section C-C in the direction shown in FIG. 7.
Figure 8A:
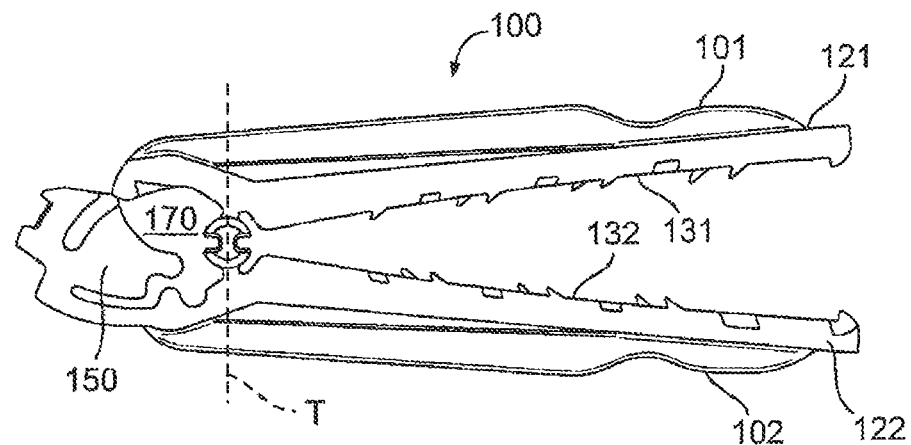
FIGS. 8a, 8b, and 8c, are side, top, and bottom views, respectively, of the clip shown in FIG. 1 in an open position.
Figure 8B:
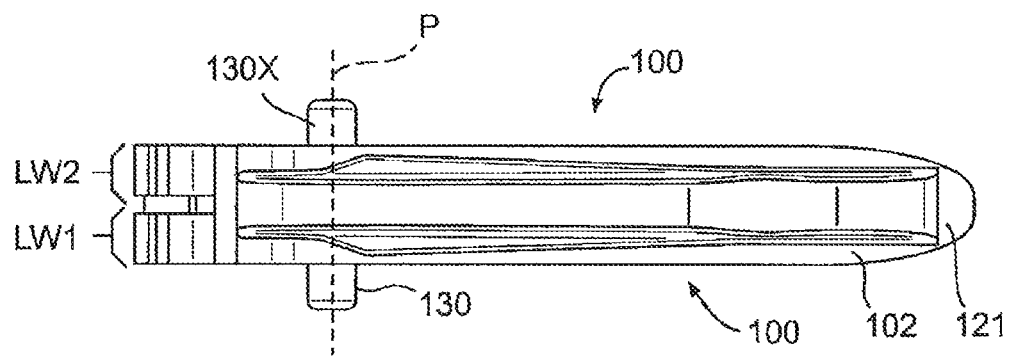
Figure 8C:
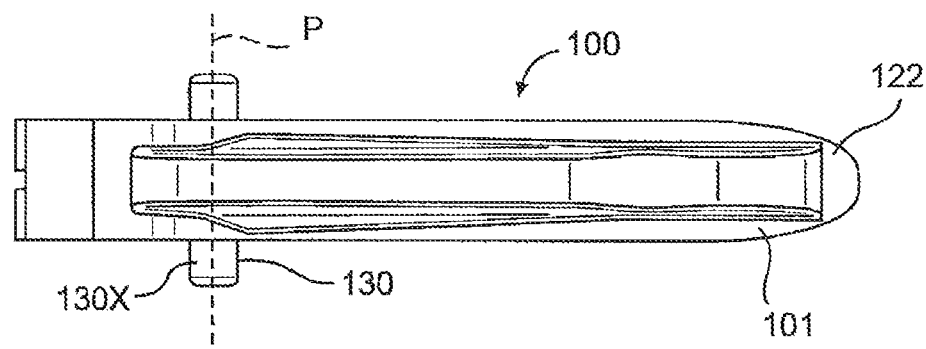
Figure 9:
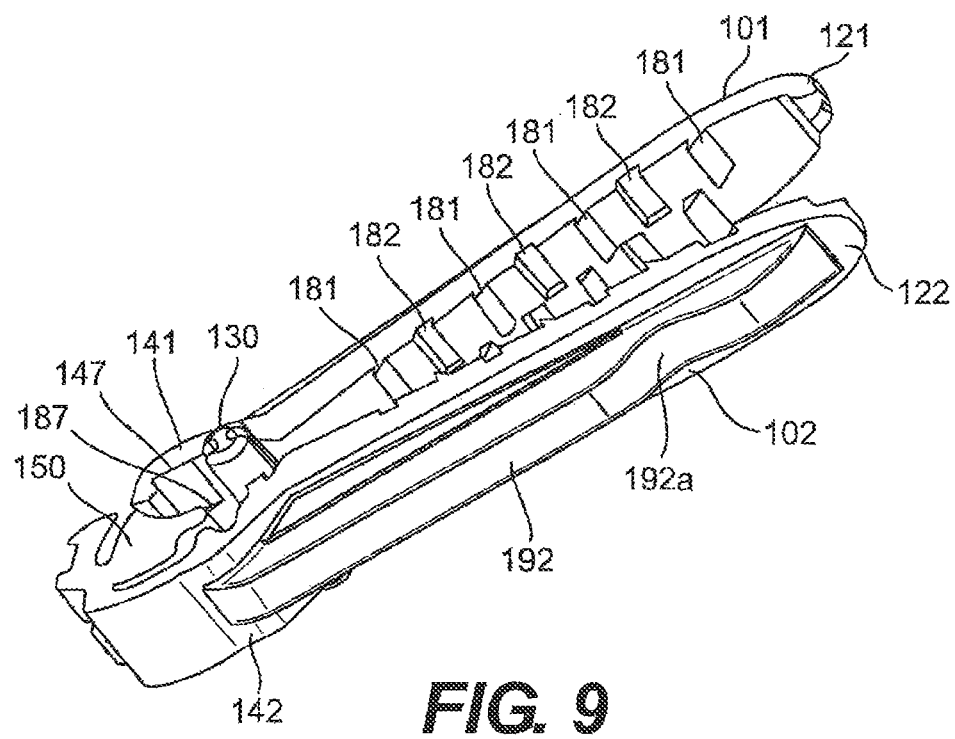
FIG. 9 is a perspective view from the bottom of the clip shown in FIG. 8a in the open position.
Figure 10:
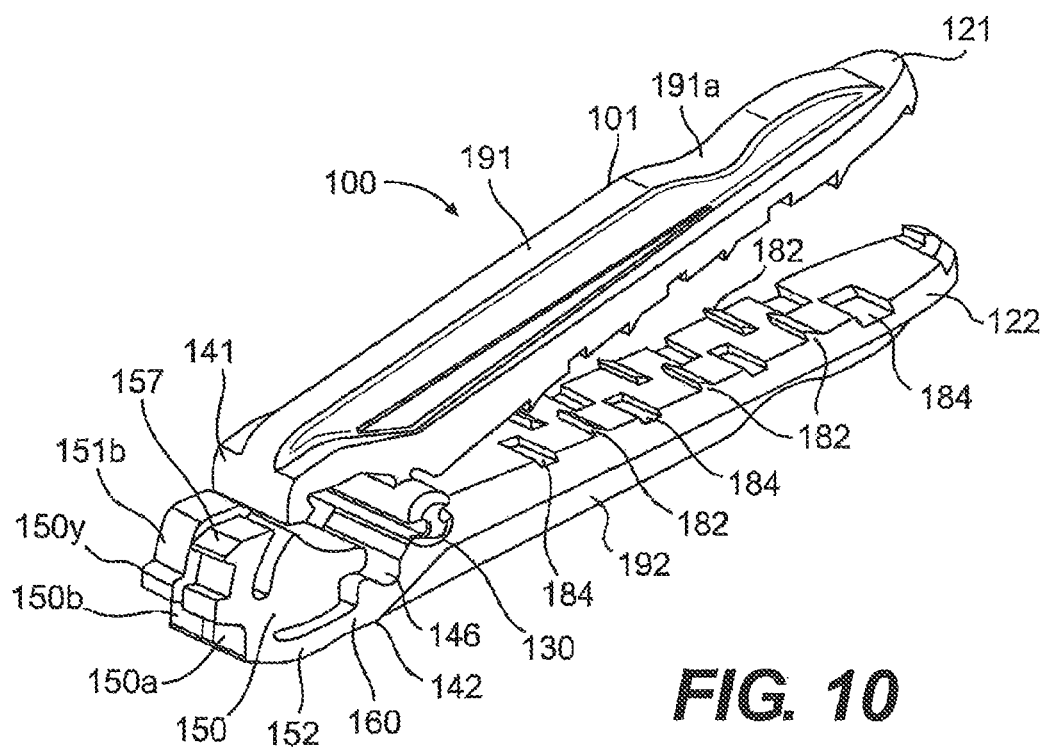
FIG. 10 is a perspective side view from the top of the clip shown in FIG. 8a in the open position.

2*b*, the wedge or buttress body 150 can be divided into two lateral sections or portions 150*a* and 150*b*, each on opposite sides of the longitudinal axis L as shown, and can form approximate lateral halves of the buttress body 150, with a possible space or small channel in-between. Lateral portion 150*b* of the buttress body 150 can have a width in a plane spanning the transverse and longitudinal axes sufficient to exceed a complementary width formed by the locking space 170 to create an interference fit between the proximal end portion 145 of the curved inner surface 143 of the first jaw structure 141 and the outer surfaces 151*a*, 151*b* on the proximal first end portion outer surface 151 of the buttress body 150, to bias the clip in a closed position. An example of the transverse width of said lateral portion 150*b* is shown as distance "TW1" in FIG. 7*a*, with complementary width "TW2" being formed by the locking space 170, it being understood that TW1 is slightly greater than TW2 in order to create the interference fit. In the embodiment as shown in FIGS. 1, 2*b*, and 7*a*, on lateral portion 150*b* there is no detent 157, and said lateral portion 150*b* of the buttress body is formed by a partial lateral width of the buttress body 150. Thus, as shown in FIG. 2*b*, the notch 147 and detent 157 are formed on corresponding partial lateral sections or slices of the buttress body 150 and first jaw structure 141, respectively, this lateral section 150*a* of buttress body 150 being on the opposite side thereof to the lateral section 150*b*. In this manner, the buttress body 150, once locked into place as shown in FIG. 12, is prevented from moving laterally from side to side since the notch 147 and detent 157 interlock only extends laterally partially across the clip, the detent 157 being limited in lateral movement by a shoulder 187 formed by a termination of the notch 147 laterally into the first jaw structure 141, as shown in FIG. 9. As shown in FIG. 8*b*, the lateral slice of buttress body 150 only extends for a lateral width LW1 which includes detent 157, which the lateral slice LW2 of buttress body 150 on the other side of the clip does not include the detent 157. In this manner, the proximal locking mechanism of the clip 100 is more stable in lateral directions, which is also useful for keeping all parts of the clip together in the event the living hinge 160 may break.

Figure 5:
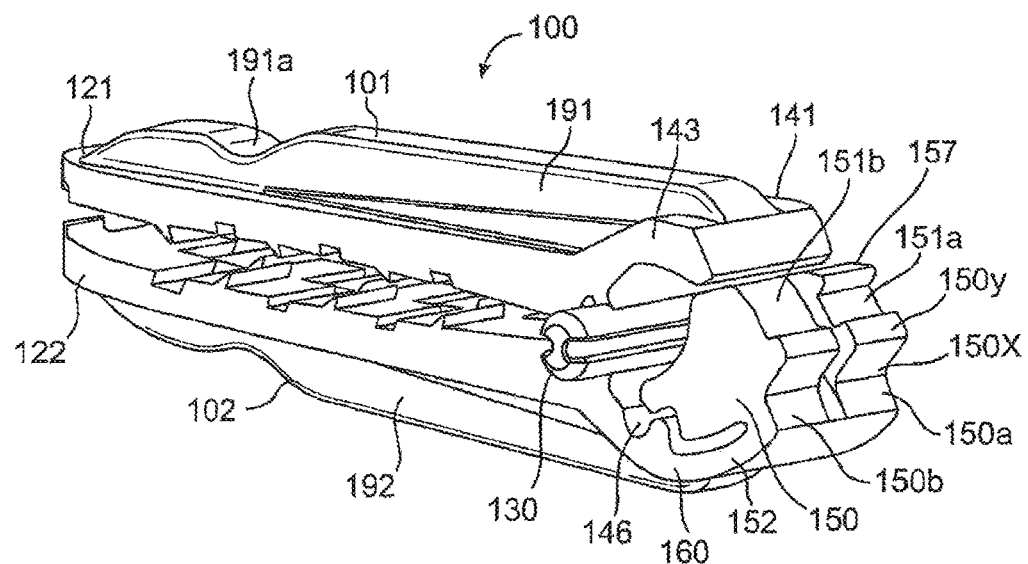
FIG. 5 shows a perspective view of the clip shown in FIG. 1 from the side opposite to that shown in FIGS. 3 and 4.

As best shown on FIG. 5, the outer surface 151 on proximal first end portion of buttress body 150 on a proximal end of the clip 100 defines one or more surfaces which form a curved planar segment abutment portion, which in the embodiment as shown includes curved planar segment abutment portions 151*a* and 151*b*. As used herein, the "curved planar segment abutment portion" formed by a surface may include a single curved surface segment or a series of curved or straight planar surface segments connected to one another which form an overall generally curved surface, each of the surface segments extending as a surface at least laterally. In the embodiment shown in FIG. 5, curved planar segment abutment portion 151*a* included planar and curved surface segments formed by the notch 157 and extends laterally for about one-half of the lateral width of clip 100, curved planar segment abutment portion 151*b* includes planar and curved surface segments which also extend laterally for about one-half of the lateral width of clip 100. Each of the curved planar segment abutment portions 151*a* and 151*b* on outer surface 151 forms a substantial abutment surface that pushes against complementary curved inner surfaces of jaw 141 to provide a stronger and more stable locking mechanism for clip 100. This is provided, at least in part, by the relatively larger and wider surface areas, lateral spans, and segmented surfaces with interlock and abut against each other to provide enhanced holding strength and stability, beyond what has been previously known or practiced in the field of surgical ligation clips.

Figure 6:
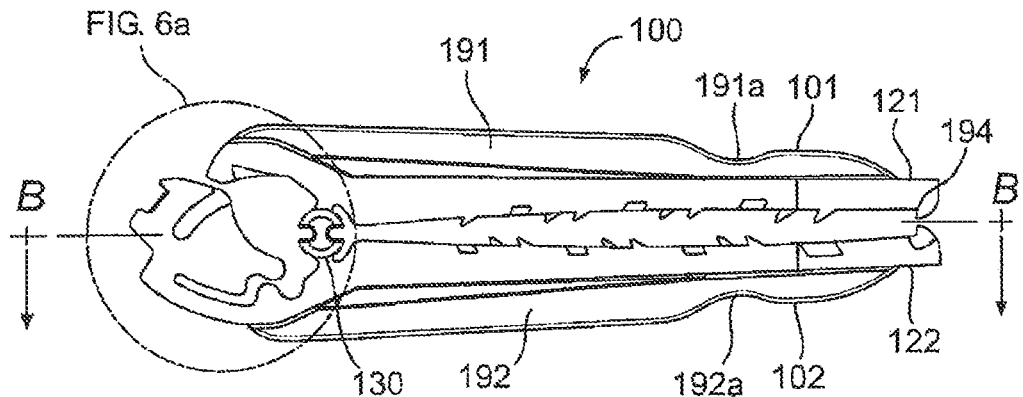
FIG. 6 is another side view of the clip shown in FIG. 1.
Figure 6A:
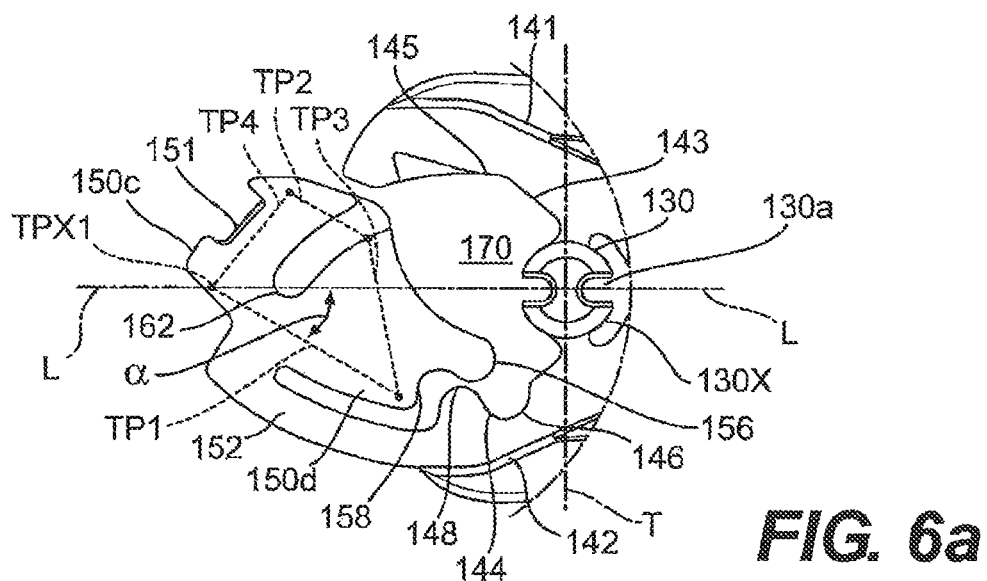
FIG. 6a is a close-up detail view of the portion of the clip shown in FIG. 6 in region "6a" therein.
Figure 6B:
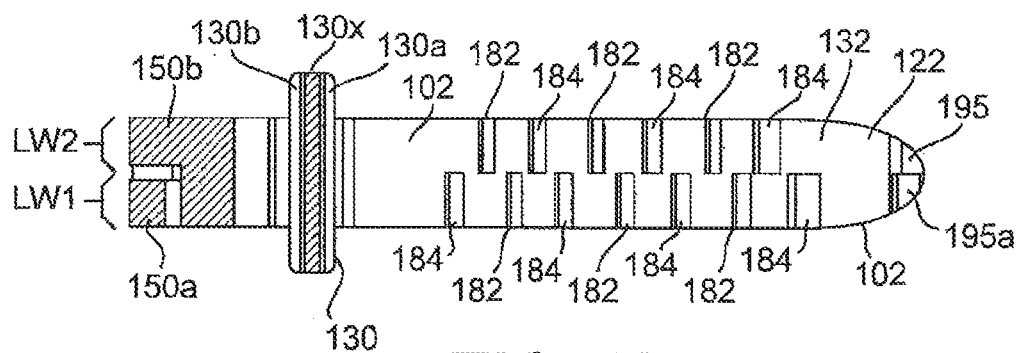
FIG. 6b is a sectional view of the clip shown in FIG. 6 taken along section B-B in the direction shown in FIG. 6.

As best shown in FIG. 6*a*, the second curved inner surface 144 on the second jaw structure 142 forms a first laterally spanning recessed groove 146 separated from the clip hinge 130 and a first laterally spanning ball-shaped or rounded protruding surface 148 proximal to said recessed groove 146, and a distal second end portion of the buttress body 150 forms a second laterally spanning recessed groove 158 and a second laterally spanning ball-shaped or rounded protruding surface 156 distal to said second recessed groove which are shaped complementary to the first rounded surface 148 and first recessed groove 146, respectively, so as to mate in abutment when the buttress body 150 is pivoted into the locking space 170 to further stabilize and bias the clip in a closed position. The first recessed groove 146, first rounded surface 148, second recessed groove 158, and second rounded surface 156 may extend laterally all the way across the lateral width of the buttress body 150, such that the first rounded surface 148 and second rounded surface 156 are not spherically shaped but rather form an extended, laterally-spanning, rounded, semi-cylindrical surface which can mate in corresponding semi-cylindrical shaped grooves formed by first recessed groove 146 and second recessed groove 158.

As shown in FIG. 6*a*, the buttress body 150 can further define a second living hinge 162 extending laterally between the proximal first end portion 150*c* of buttress body 150 and a distal second end portion 150*d*, wherein the proximal first end portion 150*c* including outer surface 151 further pivots about said second living hinge 162 when the buttress body 150 moves into the locking space 170, allowing the outer surface 151 of the proximal first end portion 150*c* of the buttress body to flex towards the longitudinal axis L prior to abutment against the curved inner surface 143 of the first jaw structure 141.

As best shown in FIGS. 5 and 12, the outer surface of the proximal end of the buttress body 150, or clip 100 itself, defines a V- or L-shaped laterally spanning notch 150*x* on the proximal end of the clip 100 and further defines a laterally spanning flange 150*y* extending from said notch 150*x* adjacent to the curved planar segment abutment portions 151*a* and 151*b*. Each of notch 150*x* and flange 150*y* may be divided into two lateral sections or components divided by a small space or channel there between as they are disposed on the lateral sectional halves 150*a* and 150*b* of the buttress body 150. The notch 150*x* provides a receiving space for the tip of an instrument, pushing or actuating rod, or another clip, so as to enable a more stable actuation of the buttress body 150 into locking space 170 to lock the clip 100. The flange 150*y* may act to limit the movement of buttress body 150 once fully inserted into locked position inside space 170, and also further stabilizes the locking mechanism for the clip 100.

Figure 13:
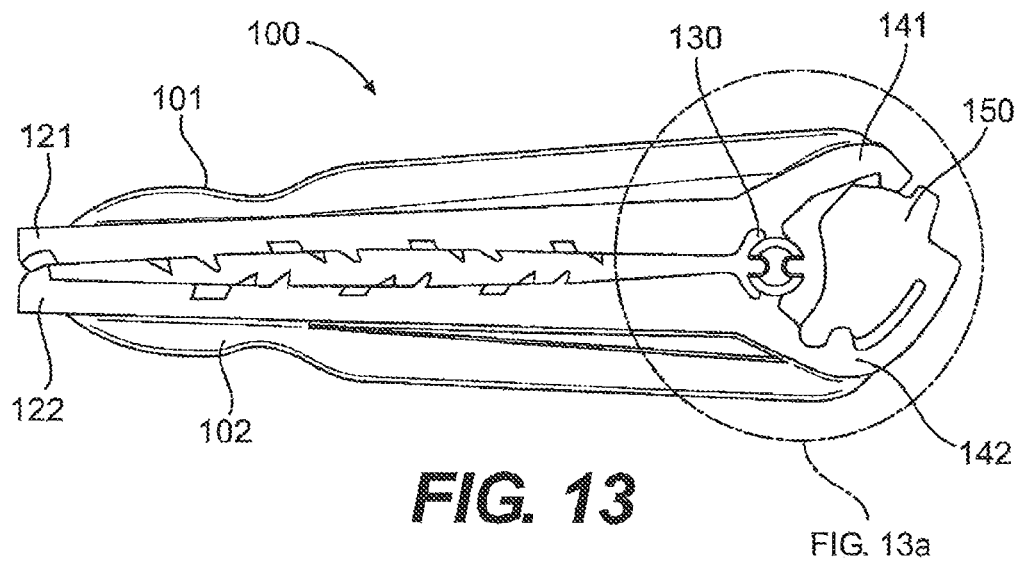
Figure 13A:
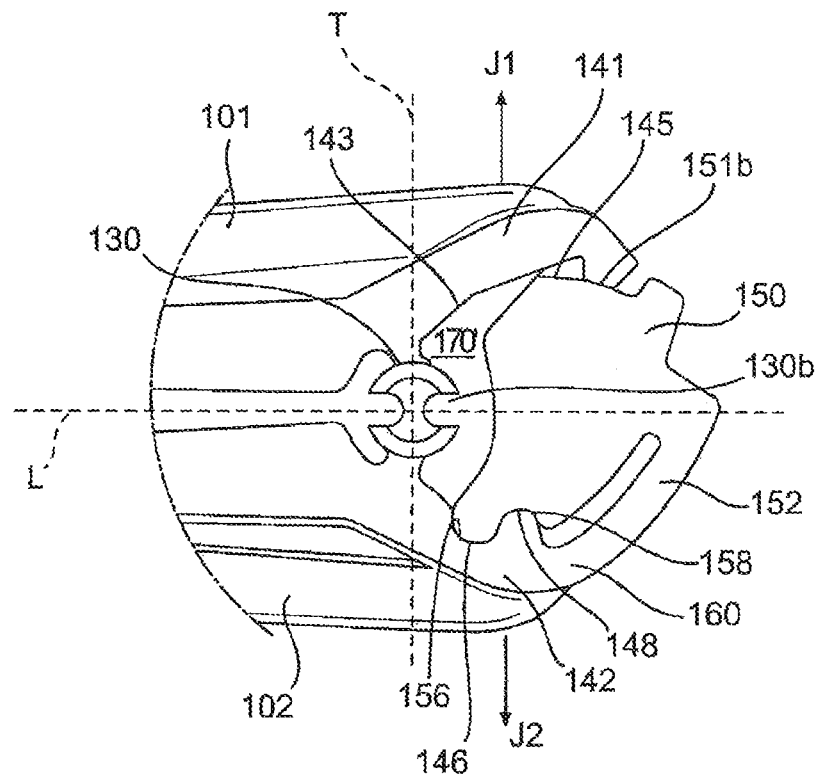
FIG. 13a is a close-up detail view of the portion of the clip shown in FIG. 13 in region "13a" therein.
Figure 14A:
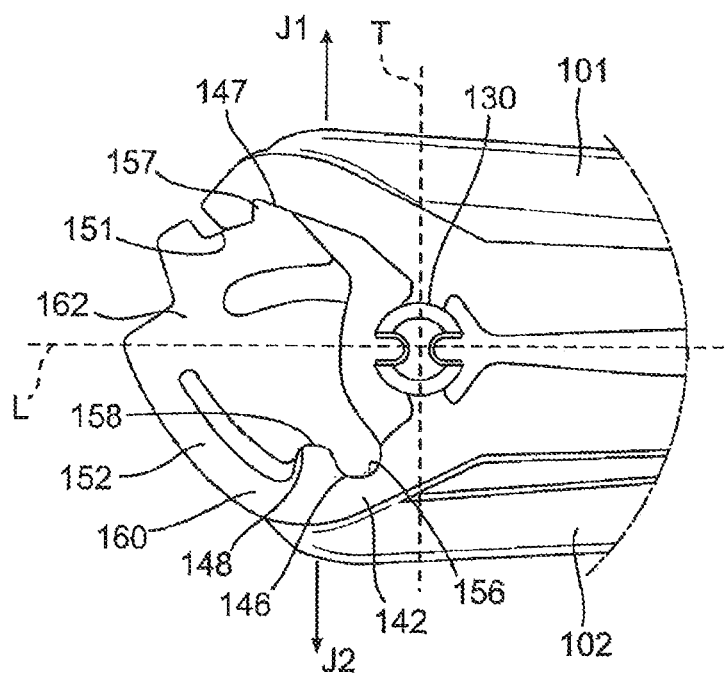
FIG. 14a is a close-up detail view of the portion of the clip shown in FIG. 14 in region "14a" therein.

In the embodiment shown in FIGS. 1-15, the buttress body may occupy a majority of a volume defined by locking space 170 when it is moved into clip locked position so as to bias the legs 101, 102 in a closed position. The volume defined by the locking space is limited by the lateral width of the clip legs 101, 102 near the hinge 130 and the jaws 141 and 142. As shown in FIG. 13*a*, the remaining locking space 170' between jaws 141 and 142, once the clip is locked by movement of the buttress body 150 into space 170, is less than half the volume of the locking space 170 as shown in FIG. 6*a*. The presence of a bulky body like buttress body 150 which occupies the majority of the volume or space between proximal extending jaws 141 and 142 when the clip 100 is in the locked position further provides a greater strength and stability to the locking of said clip.

In the embodiment shown in FIGS. 1-15, and as shown in FIG. 6a, the buttress body 150 can be characterized in one way as having a core mass which has, in a transverse plane spanning the longitudinal and transverse axes, a cross-section which approximately spans a trapezoidal shape, having rounded curved sides extending from the sides TP1, TP2, TP3, TP4 of the trapezoid. Side TP1 defines the longest side and one of the parallel sides of the trapezoid, while side TP2 defines the shorter parallel side. Side TP3 defines the longer and more distal of the non-parallel sides, while side TP4 defines the shorter and more proximal non-parallel side. Side TP1 is therefore connected to sides TP3 and TP4. When the clip is in the unlocked position as shown in FIG. 6a, and the buttress body 150 is fully extended away from the clip hinge 130 out in the most proximal position, the vertex TPX1 of sides TP1 and TP4 lies approximately on or near the longitudinal axis L, and side TP1 makes an angle α below the longitudinal axis, towards proximal jaw 142, such angle α being, in one embodiment, approximately 30 degrees. As shown in FIG. 6a, the rounded laterally-spanning protuberance 156 extends substantially from side TP3.

The clip hinge 130 can also be a resilient hinge providing additional biasing force to maintain the inner clamping surfaces 131, 132 of the legs towards a closed position. A span of each leg extending from the clip hinge 130 to its respective distal tip 123, 124, can be, in one embodiment of the present invention, at least 75% to 80% of an overall length of the clip. As shown in FIGS. 2b and 2c, the clip hinge 130 can define lateral bosses which extend laterally from the side surfaces of the clip legs, defining a bossed width or span which is greater than the clip width.

In the embodiment shown in FIGS. 1-15, the clip hinge 130 is formed as a laterally extending bar 130x integrally formed with the first and second legs 101, 102, each leg being resiliently coupled to first and second transverse sides of said bar, the bar 130x further defining laterally spanning grooves 130a and 130b on longitudinally distal and proximal sides of the bar, respectively. These grooves 130a and 130b further enable the clip 100 to flex as pivoting about the lateral axis of hinge 130, and further provide a resilient pivoting moment or force about said hinge.

Furthermore, in the embodiment shown in FIGS. 1-15, flanges 191 and 192 extend longitudinally across respective outer surfaces of each of the first and second legs 101, 102 which are on opposite sides to the inner clamping surfaces 131, 132 of each respective leg, the flange 191 of the first leg 101 extending from the first jaw structure 141 to the distal end portion 121 of the first leg 101, the flange 192 of the second leg 102 extending from the second jaw structure 142 to the distal end portion 122 of the second leg 102. Each of the flanges 191, 192 defines a transverse indentation 191a, 192a proximate the distal end portions 121, 122 of the legs 101, 102. The flanges 191 and 192 provide a rigidity to legs 101 and 102, respectively, such that said legs do not easily bend. Transverse indentations 191a and 192a provide a means for a clip applier to better actuate or grip the legs 101, 102.

Figure 19:
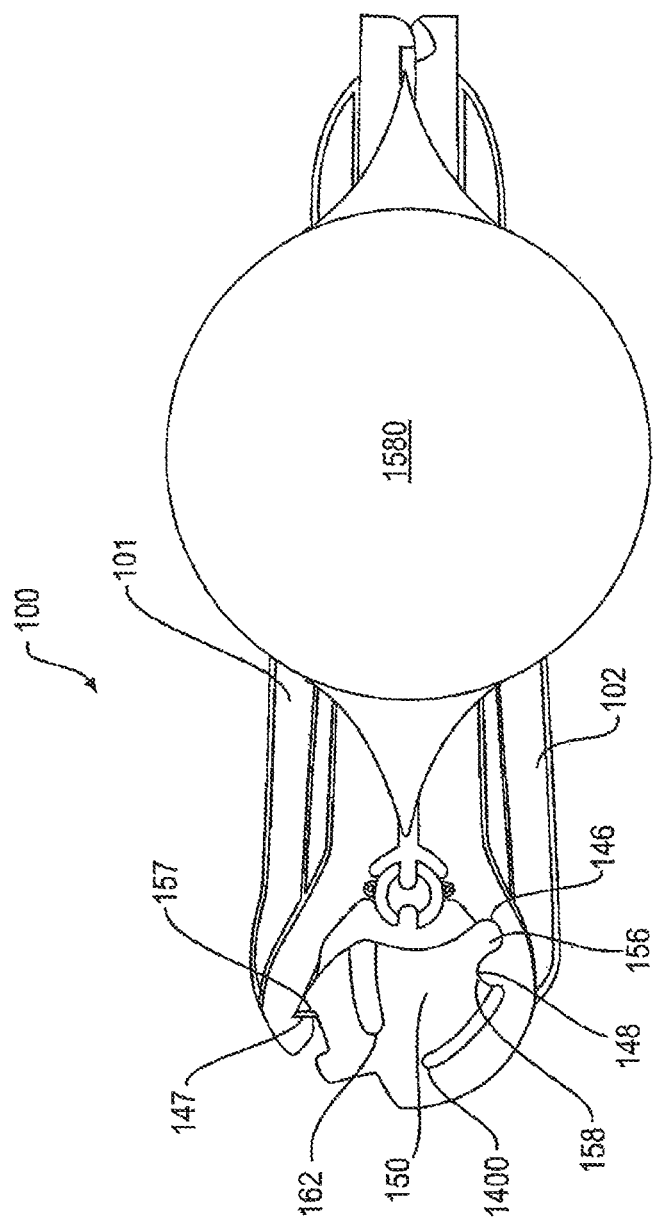
FIG. 19 shows a clip latched on vessel.
Figure 20:
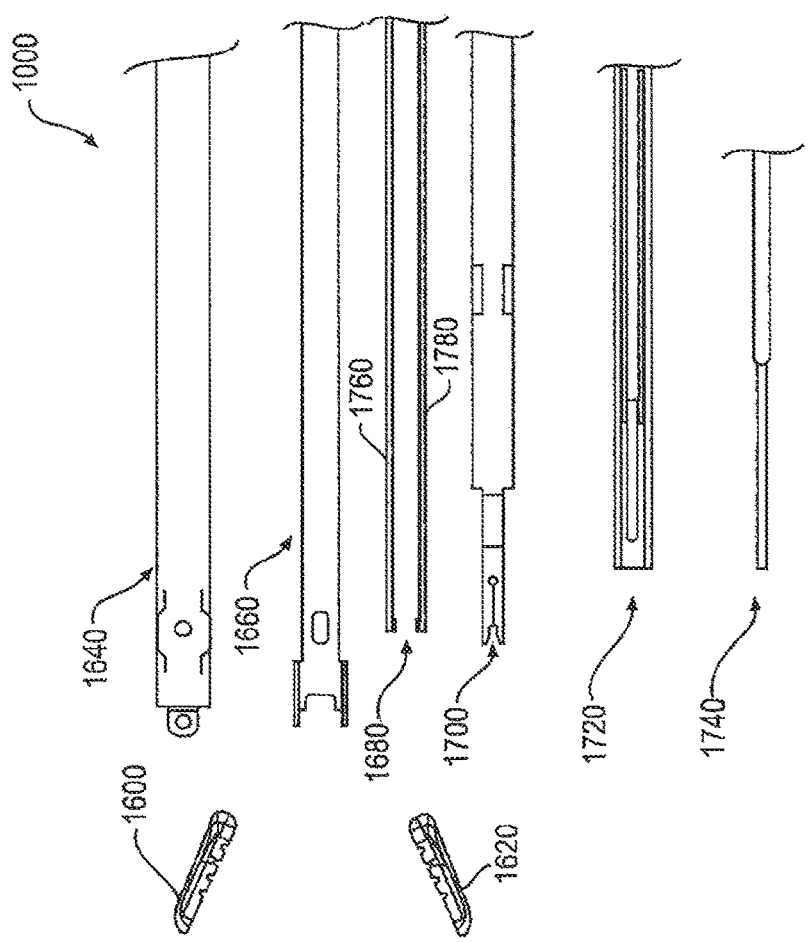
FIG. 20 shows an exploded view of applier parts.

The clip 100 further includes serrations, ridges, or teeth 181, 182 on the inner clamping surfaces 131 and 132, respectively, as shown in FIGS. 6b and 7b, and 9, 10, and 15a. The teeth or ridges 181, 182 provide additional grasping means to better attach and clamp the clip 100 onto a vessel when closed. The teeth or ridges 181, 182 are disposed to fit into complementarily arranged grooves 183 and 184 on the clamping surfaces 131 and 132, respectively. The teeth 181, 182 may have a slanted orientation, extending proximally, so as to better grip tissue. As best shown in FIGS. 6-6a and 7-7a, a pair of distal hook elements 194 and 195 may be disposed on the absolute distal tips of legs 101 and 102, respectively, each hook 194 and 195 offset laterally with respect to each other to form a scissor-like configuration, such that each hook 194 and 195 fit into corresponding recesses 195a and 194a, respectively, on the distal tips of legs 102 and 101, respectively. This mechanism provides means to further grip and contain tissue with the space between the clamping surfaces 131, 132 when the clip 100 is applied to body vessel, as illustrated in FIGS. 19 and 20.

Figure 15:
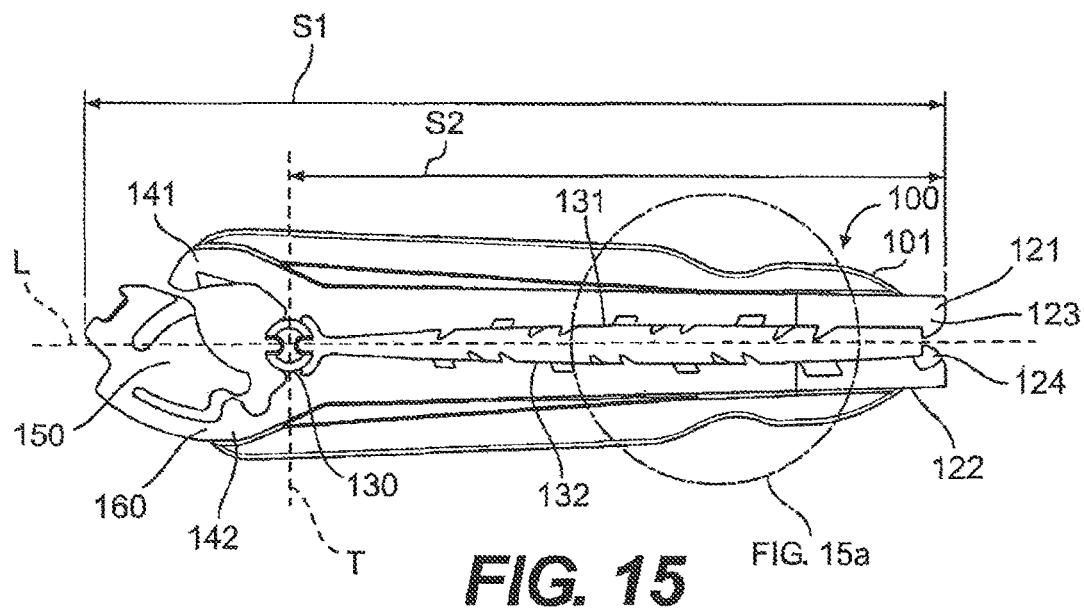
FIG. 15 is a view of the clip shown in FIG. 1.
Figure 15A:
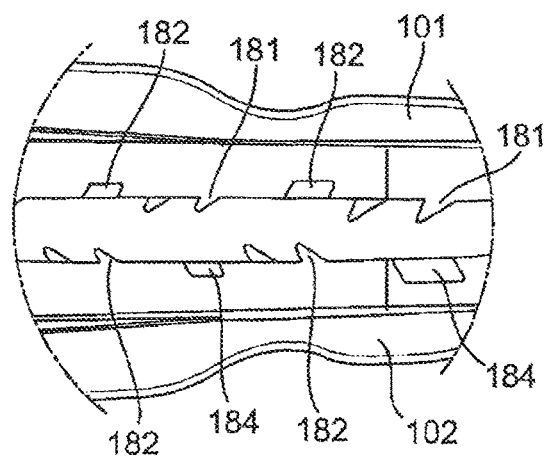
FIG. 15a is a close-up detail view of the portion of the clip shown in FIG. 15 in region "15a" therein.

The clip 100 may be in a range of sizes. As shown in FIG. 15, an overall length "S1" of the clip 100 may be approximately 0.50 inches; the length "S2", between the intersection of transverse axis T and longitudinal axis L centered at clip hinge 130 and the distal tip of the clip, may be approximately 0.40 inches, and the radius of curvature of the inner mating or clamping surfaces 131, 132 of the legs 101, 102 may be approximately 3.0 inches. Such sizes and dimensions are given as an example, and it is understood that the clip may, in one or more embodiments of the invention, vary in size ranging from approximately 0.15 to 0.80 inches in overall longitudinal length, and from approximately 0.03 to 0.15 inches in lateral width. As one embodiment of the invention, the illustration of clip 100 in FIG. 15 is shown as a scaled magnification of actual size, and shows all the parts of the clip 100 in actual proportion to each other.

The instrumentation used to deploy the clips discussed herein may include a manually loaded device that can apply a single clip at a time, or an automatically fed, multiclip applier. Both appliers can be endoscopic instruments suitable for use in laparoscopic surgery applications. In both cases the applier will clamp over the vessel to flatten the section to be ligated. The clip will then be opened, positioned over the vessel and closed. Once closed, a mechanism will engage the locking feature on the proximal end of the clips disclosed herein, to maintain the clamping pressure of the clip. A manual applier will load/apply a single clip at a time. An automatic applier will be able to load/apply multiple clips before the instrument has to be removed from the surgical site. The sequence of clip application is as follows:

1. The clip is presented in the partially closed condition.
2. A device, such as a set of applier jaws clamps down on the vessel or tissue to be ligated or clamped. The applier jaws have a channel down the center that is just large enough to allow the clip to fit in the channel.
3. The clip is opened by pressing the proximal legs together lightly.
4. The clip is advanced over the vessel or tissue that is clamped within the jaws of the applier (the clip traveling in the channel area of the applier jaws).
5. Once fully advanced, the proximal legs are released and the clip springs back to the partially closed condition.
6. The proximal locking mechanisms discussed for the clip embodiments disclosed herein are actuated or pressed, causing the legs or 'clamping section' of the clips to close tightly on the vessel or tissue.

The various embodiments of the clips disclosed herein therefore can start in an as-molded state; can be opened further to better encapsulate the vessel; and can then be closed further (into a third state). This process of opening and closing the clip can be repeated as needed, prior to locking. When closed and locked, the clip provides an active clamping force which can also squeeze the vessel, which is beneficial if the vessel necroses and/or shrinks over time.

The various embodiments of the surgical clips of the present invention are preferably made of one or more polymer materials, such as, by example, acetyl homopolymer, but could also be made of a variety of other materials, including one or more metals, or a combination of metal and polymer or plastic. In selecting the material(s) used, the radiopacity of the clip can be "tuned" to a desirable level, or can be tuned to be radiopaque.

The various embodiments of surgical clips of the present invention are an improvement over the known polymeric surgical ligation clips, as well as standard metal clips. Among the resulting advantages of the surgical clip of the invention as disclosed herein are: the ability to deliver a larger clip through a smaller endoscopic instrument; the ability to place a clip on a vessel just like a prior art malleable and deformable metal clip, with no need for added dissection or cleaning around the vessel, but with greater retention force than metal clips, which results in a reduced risk of clips slipping off the vessels. The greater clip locking stability and clip retention force is accomplished by the locking feature applying an active biasing or clamping force as discussed above, versus the passive clamping action created by plastic deformation of malleable metal clips. A brief discussion with reference to the FIGS. will now be discussed with a more detailed discussion referencing the FIGS. and referencing reference characters will follow.

The distal portion of the applier would be attached to a proximal handle with components that achieve the proper sequence to successfully apply a ligation clip.

Figure 30:
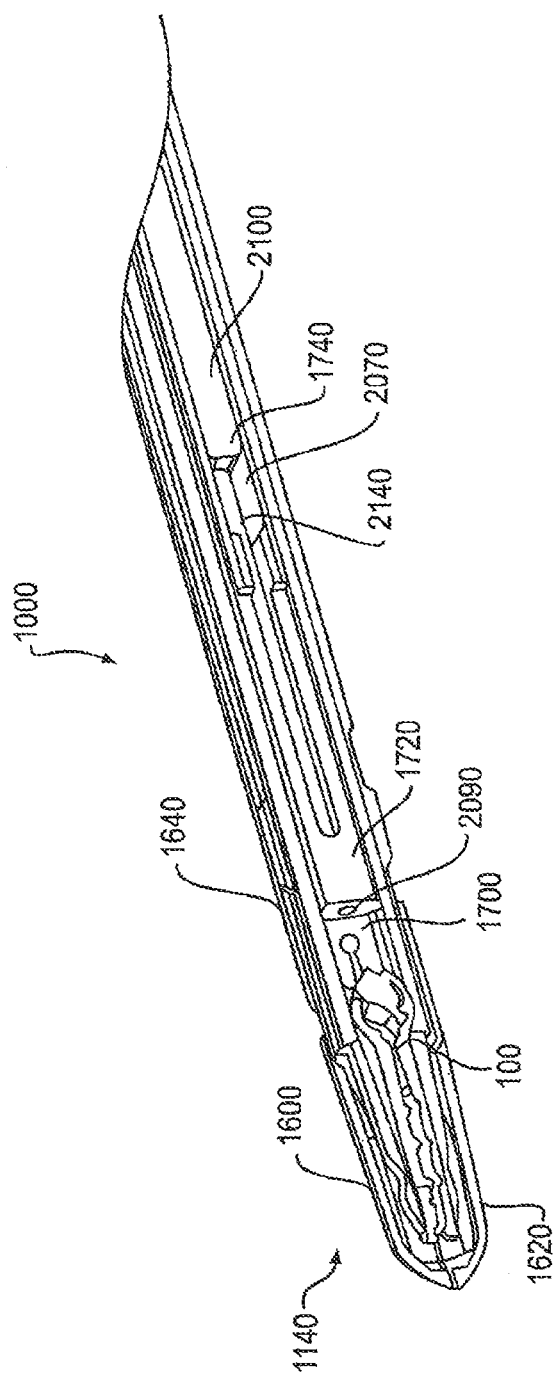
FIG. 30 shows an applier shaft distal end.
Figure 31:
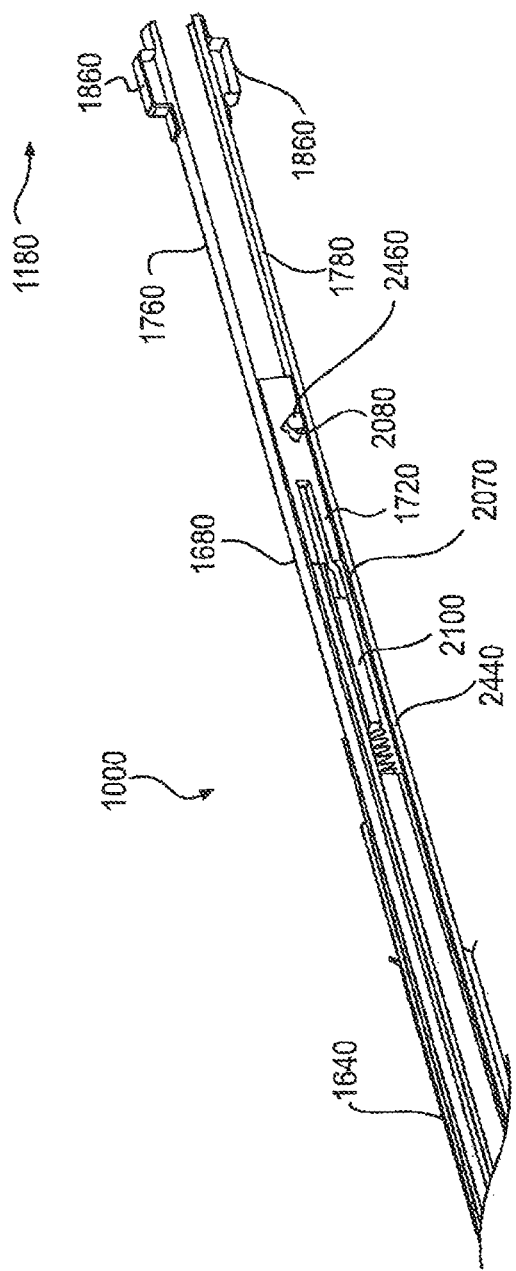
FIG. 31 shows an applier shaft proximal end.

One particular embodiment, of the distal portion of the invention, consists of nine parts which make up the distal end, or shaft of the applier, parts are shown and labeled in FIG. 20. There are two identical wedges used, shown in FIG. 21, one catch, shown in FIG. 22, one punch, shown in FIG. 23, one clip indicator, shown in FIG. 24, one inner tube, shown in FIG. 25, two jaws, shown in FIG. 28 and one outer tube, shown in FIG. 29. Each of these parts are put together to form the applier shaft. FIG. 30 shows the distal end of the shaft assembly and FIG. 31 shows the proximal end of the shaft assembly. There is a varied length between the distal and proximal portions of the shaft which is a function of standard endoscopic instrumentation suitable for use in laparoscopic surgery applications.

The manual applier has a clip loaded into the applier before it can apply a clip. The clips may be loaded into the applier with, but are not limited to, the use of a clip cartridge where clips are presented to the applier in a particular orientation. A version of a clip cartridge, for illustration purposes only, is shown in FIG. 32-36.

Figure 37:
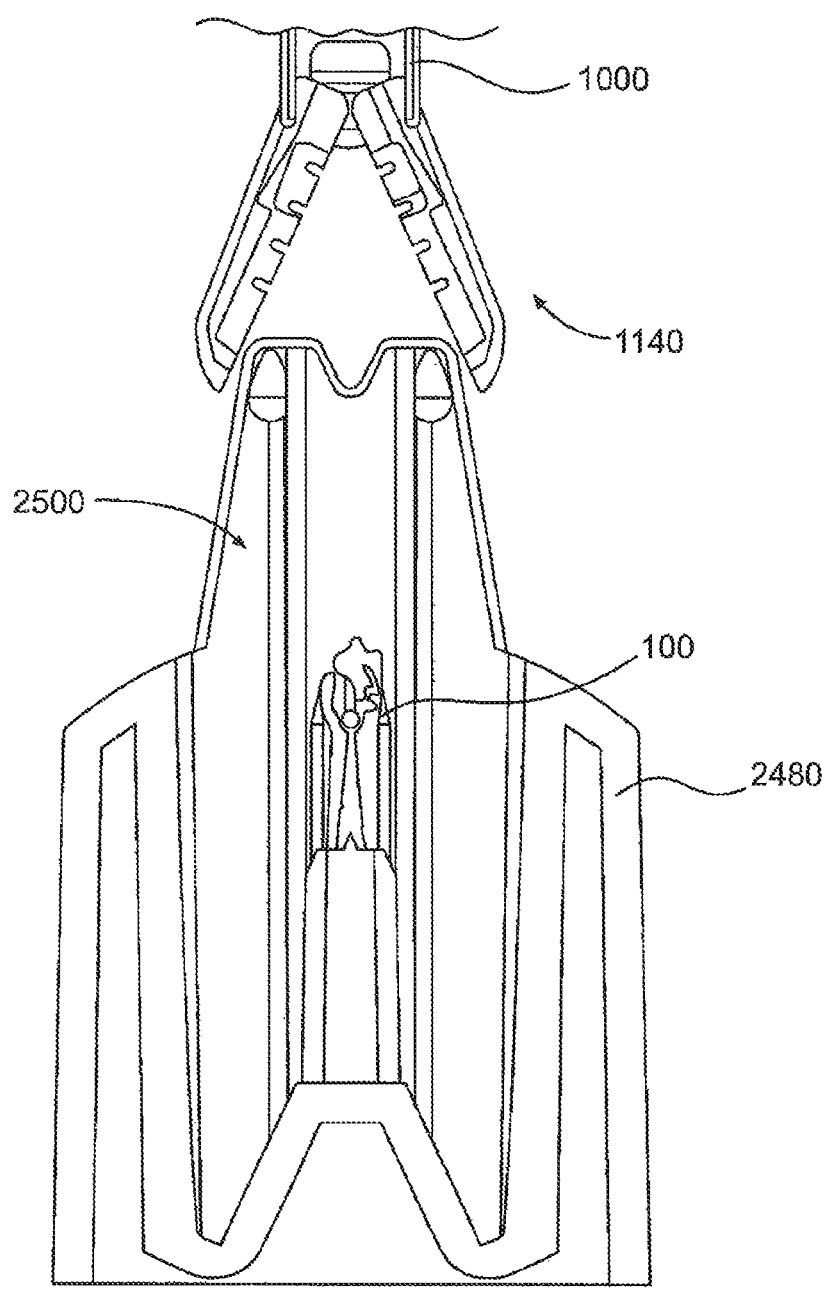
FIG. 37 shows an approach to cartridge for clip load.
Figure 38:
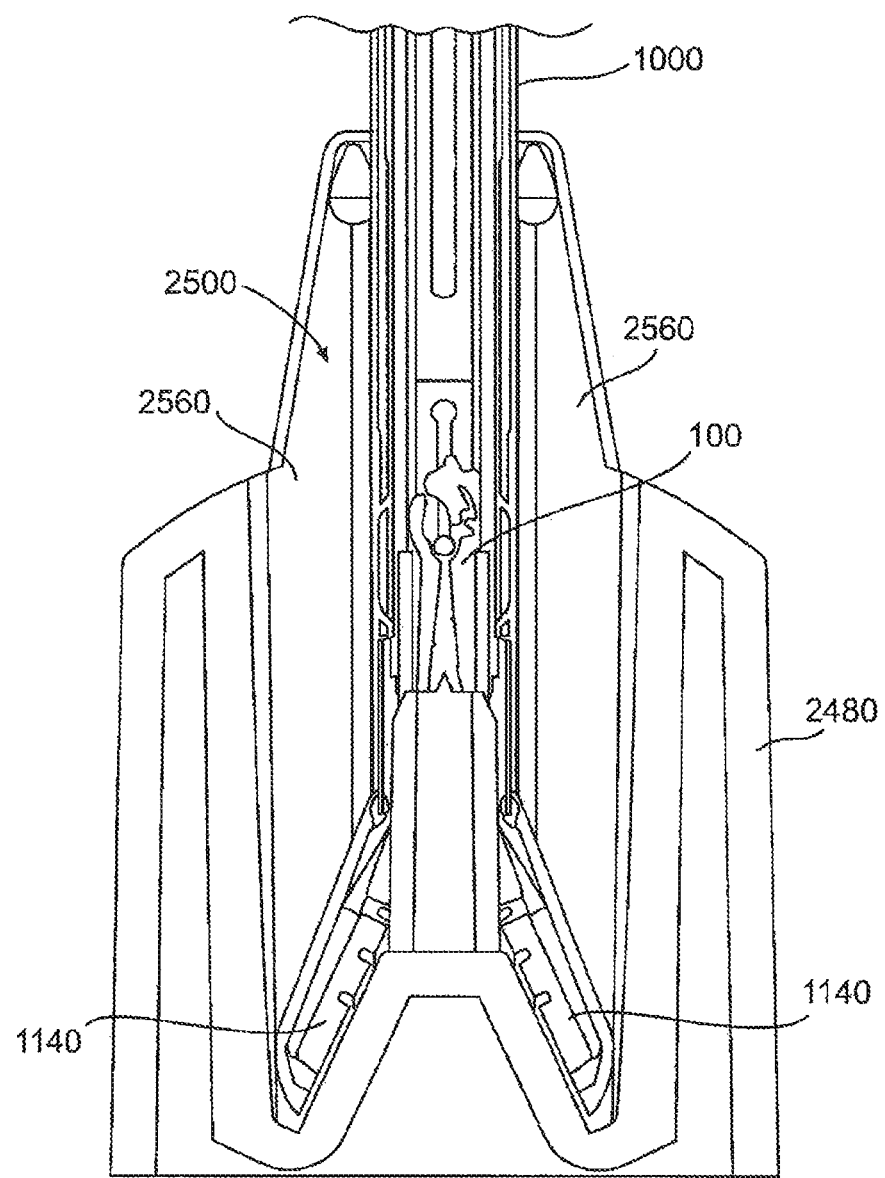
FIG. 38 shows a clip load.

FIG. 37 shows the distal end of the applier on approach to the cartridge and FIG. 38 shows the distal end of the shaft in the clip load position. Following images will exclude the Clip cartridge so that the specific actuation of the individual parts can be seen.

Figure 39:
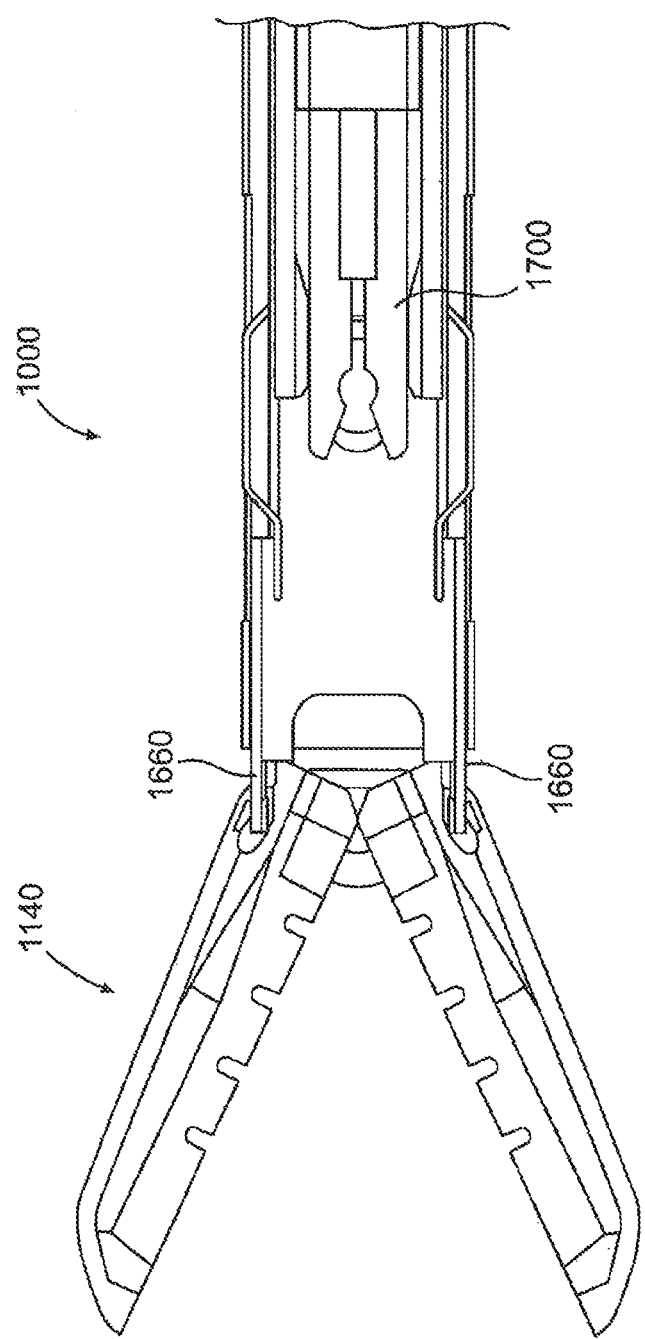
FIG. 39 shows an approach to clip cartridge (cartridge and clip not shown).

FIG. 39 shows the applier in a free state which is the same state the applier will be in on approach to the clip cartridge. Note the location of the parts in the assembly as this will be used as a reference location of the parts during actuation of the applier (images not to scale).

The outer tube remains stationary and is the base for the shaft components. On the distal end of the outer tube there are spring fingers that force the wedges together as they move within the assembly. The end of the outer tube has two tabs with holes that the jaws mount into.

Figure 29:
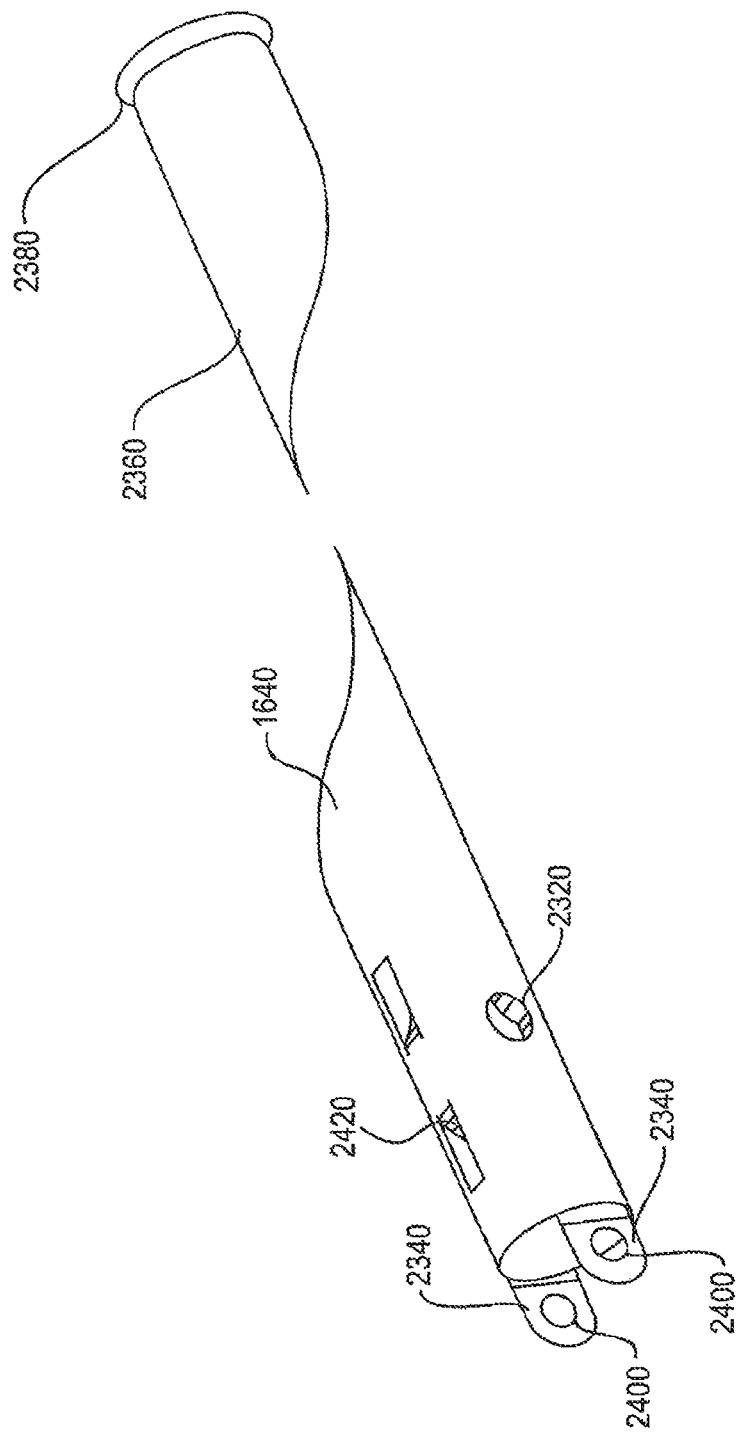
FIG. 29 shows an outer tube.

The inner tube is inserted into the outer tube and controls the actuation of the jaws, which are assembled to the distal end of the outer tube in the tabs on the end; see FIG. 29 for tab location. The jaws use the hole in the tab of the outer tube as a bearing surface in which they rotate. As the inner tube is slid toward the proximal end of the shaft the jaws are cammed open and when the inner tube is slid distally the jaws are cammed closed, see FIGS. 26 & 27. The actuation of the inner tube and jaws are independent of all other parts in the applier shaft. This allows the jaws to be used in grasping and dissecting with or without a clip in the load position. During the loading of the clip the jaws are fully open.

The clip is loaded into the distal end of the applier shaft by pressing the clip bosses into the clip catch. The catch is inserted into the outer and inner tubes. There are two sets of legs cut into the distal end of the catch, see FIG. 22. The legs on each side of the catch spread apart when the clip bosses are pressed into them. Once the clip bosses reach the circular cutout, on the distal end of the catch, the legs spring back together and capture the clip bosses. The catch also has tabs that orient the wedges.

Figure 21:
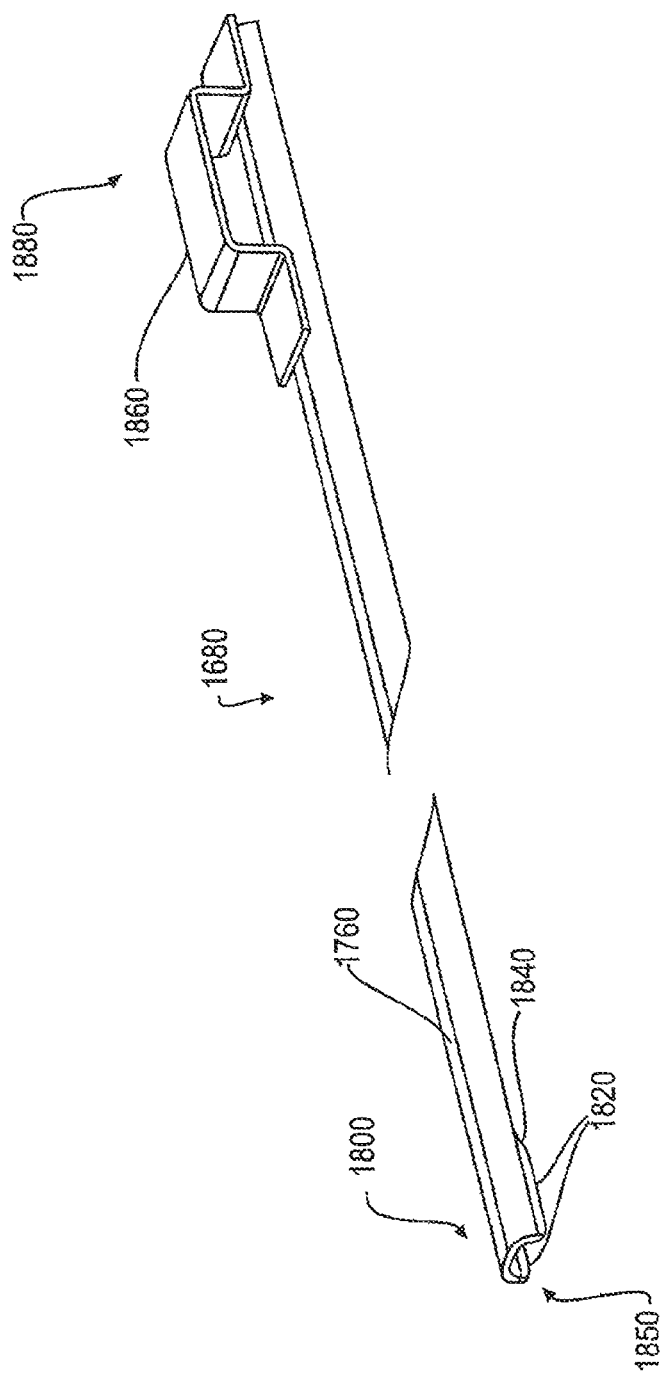
FIG. 21 shows a wedge.

During loading the clip is forced open by the fingers on the distal ends of the wedges, see FIG. 21. The wedges are inserted into the catch and orientated by the tabs on the catch to capture the upper and lower halves of the clip. The distal ends of the wedges are forced together by the spring fingers on the outer tube; this is where the force to open the clip comes from. The wedges capture and orient the punch, which in turn biases the wedges into the tabs of the catch, see FIG. 56.

Figure 57:
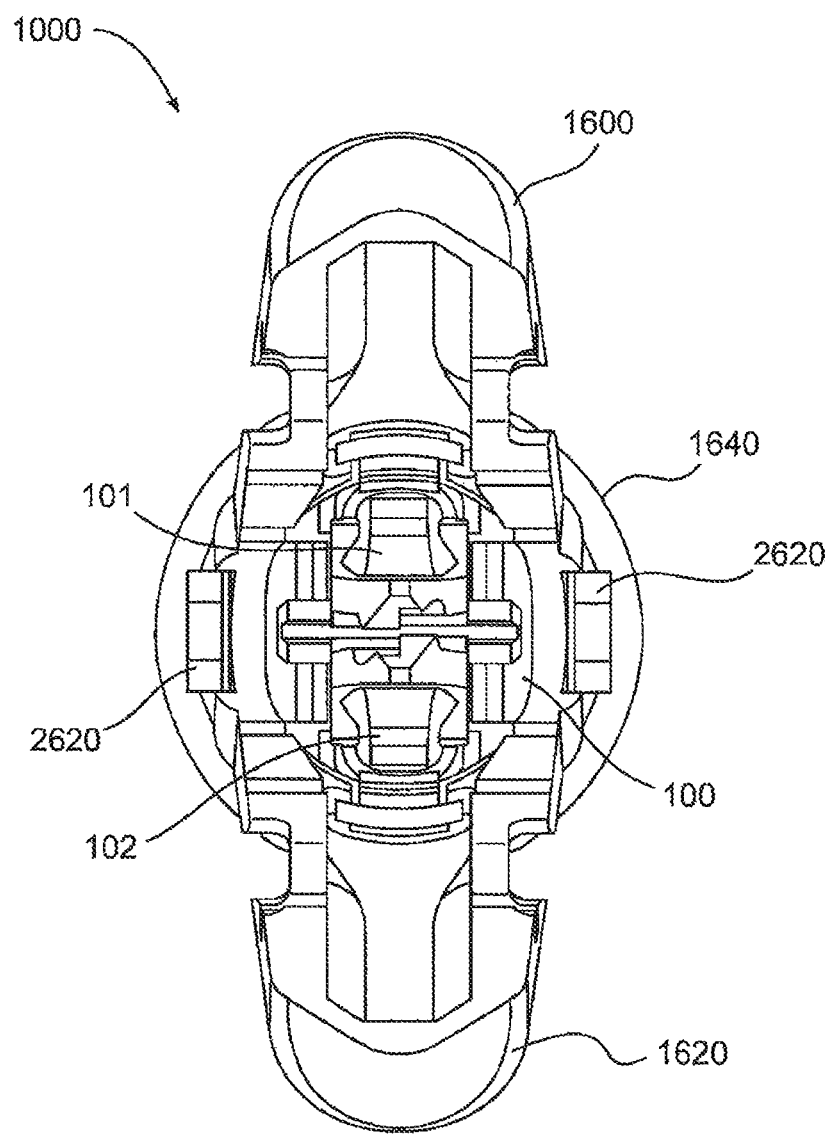
FIG. 57 shows an end view of applier with jaws open and clip loaded.
Figure 59:
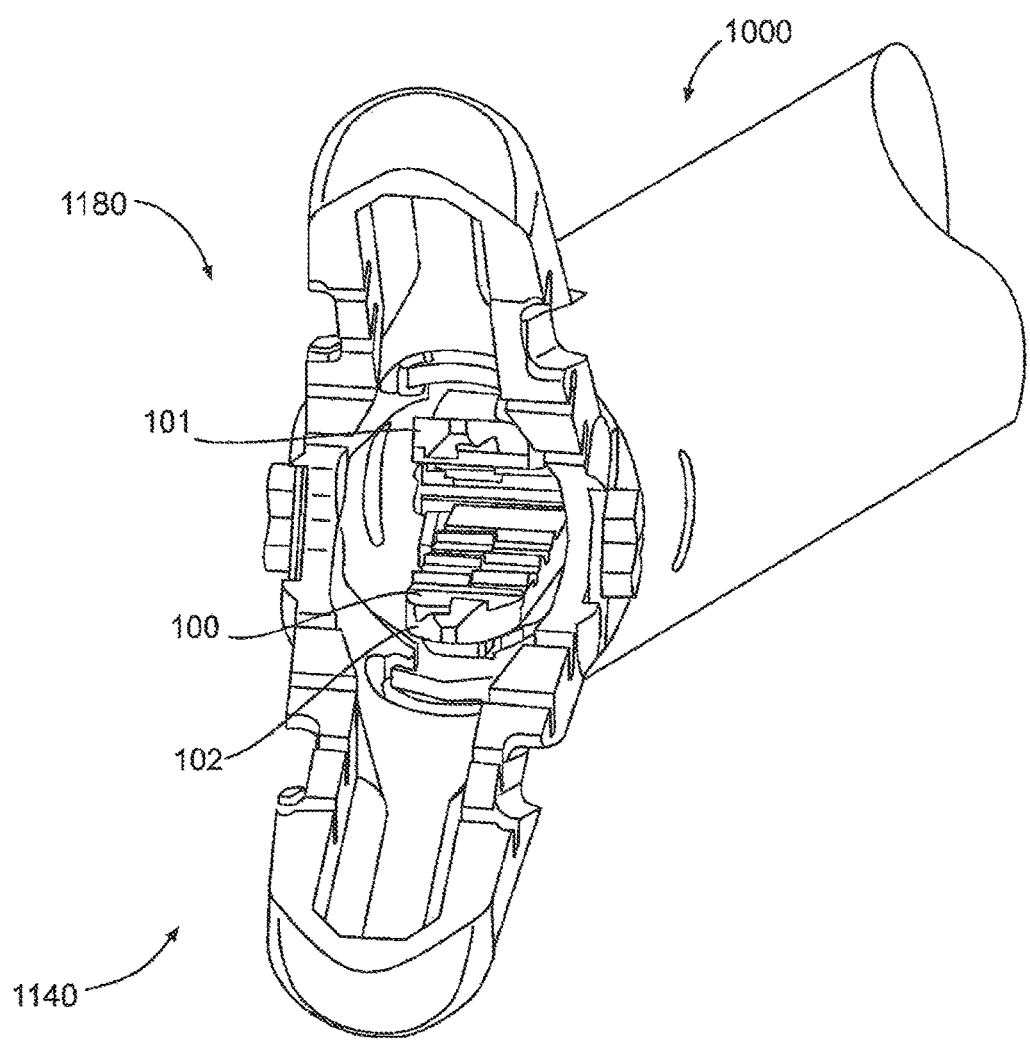
FIG. 59 shows a isometric view of distal end of applier shaft with clip loaded.

FIG. 57 and FIG. 59 show different views of a loaded clip in the applier with the jaws open. On the side of the outer tube there may be a view port cut into the shaft to allow a visual of a loaded clip. This would allow the presence of a clip to be confirmed through the use of a camera during a laparoscopic surgery without having to remove the applier to confirm. The view port is located to view the boss of a clip from either side of the applier and is position so the boss can only be viewed in the loaded position, see FIG. 60.

Figure 41:
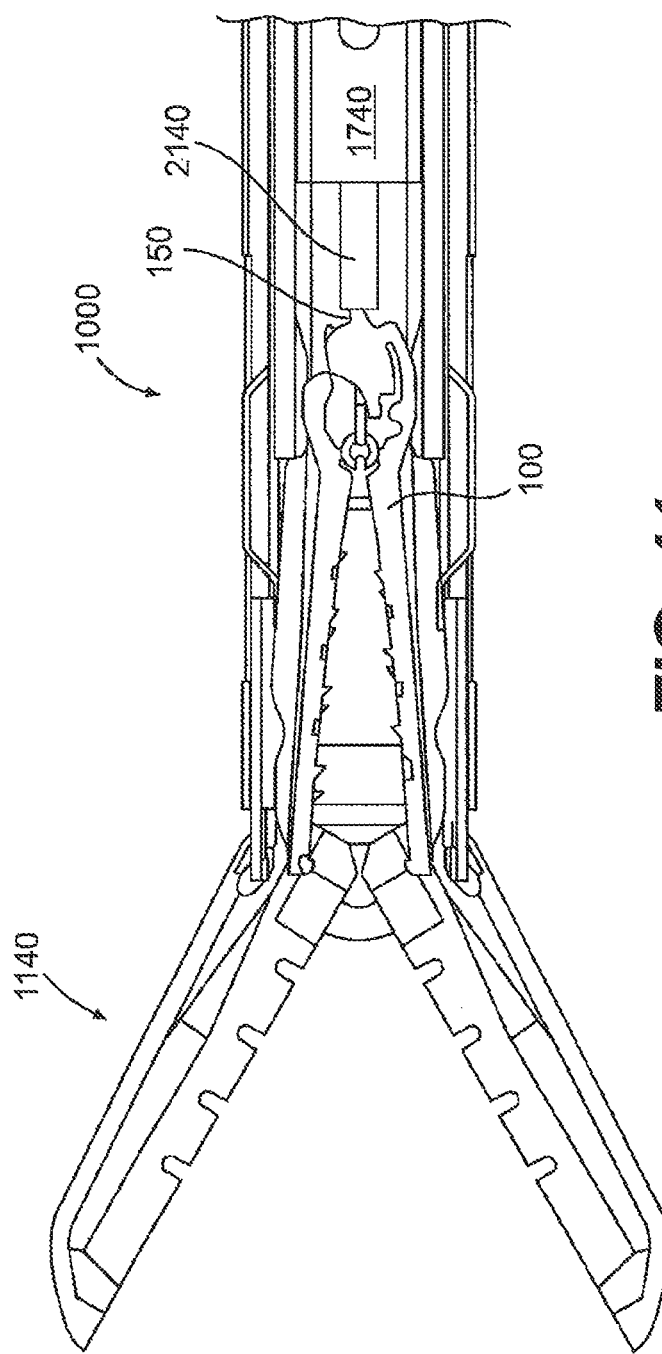
FIG. 41 shows a clip loaded.

As the clip is loaded it presses against the clip indicator which is mounted inside the punch, see FIG. 41. The clip indicator is spring loaded so that the distal end is always biased toward the distal end of the applier until it is pushed against by the clip. When the clip is loaded a flag on the proximal end of the clip indicator signals the operator visually that the clip is present.

Figure 42:
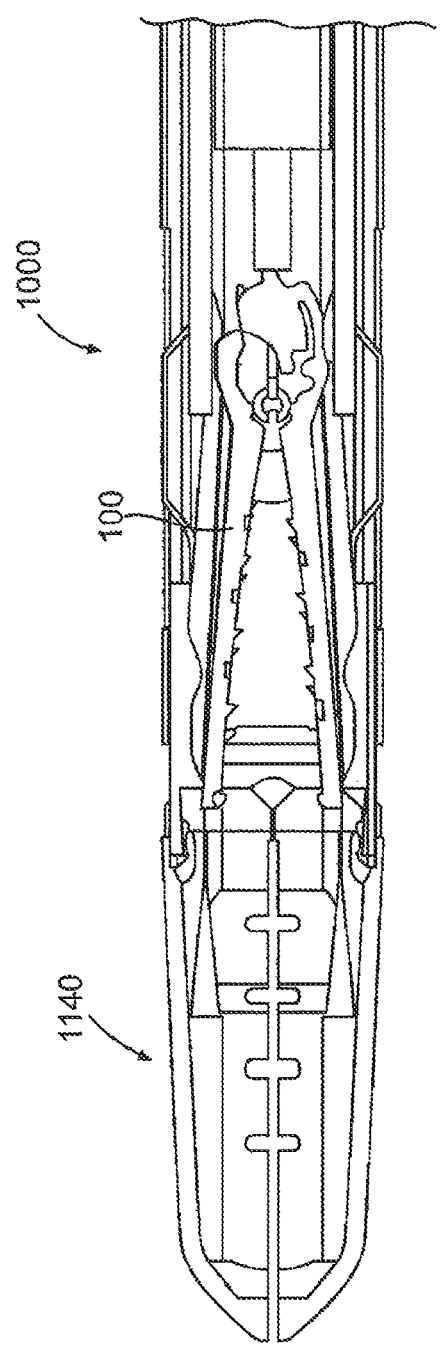
FIG. 42 shows jaws closed.

At this point the clip is loaded and the jaws can move freely without disturbing the clip, see FIG. 41 and FIG. 42. The jaws are then used to grab the vessel intended to be ligated. The jaws flatten out and hold the vessel so that the loaded clip can be advanced over the vessel, closed, and locked. The compression of the vessel allows for a thinner cross-section for the clip to advance over and holds the vessel in place while the clip is being closed to ensure that the clip is fully seated on the vessel before it is locked. The jaws have half circle cutouts to allow fluid to flow out of the vessel when the clip is closed. This keeps the vessel from forming a "bubble" in the jaw cavity.

Once the jaws are closed on the vessel the clip is advanced into the jaws from the load location. The catch, wedges, and punch move toward the distal end of the shaft in unison, see FIG. 43. The legs of the clip are stopped by the inner end surface of the jaws. The catch then remains stationary as the wedges advance over the clip legs forcing the clip to close. At the same time the wedges are advancing the punch is advancing up to the buttress of the clip, see FIG. 47. Once the wedges have advance to their furthest point toward the distal end of the jaws the punch continues forward forcing the locking mechanism on the clip to rotate into the clip's locked position, see FIG. 48-50.

Figure 51:
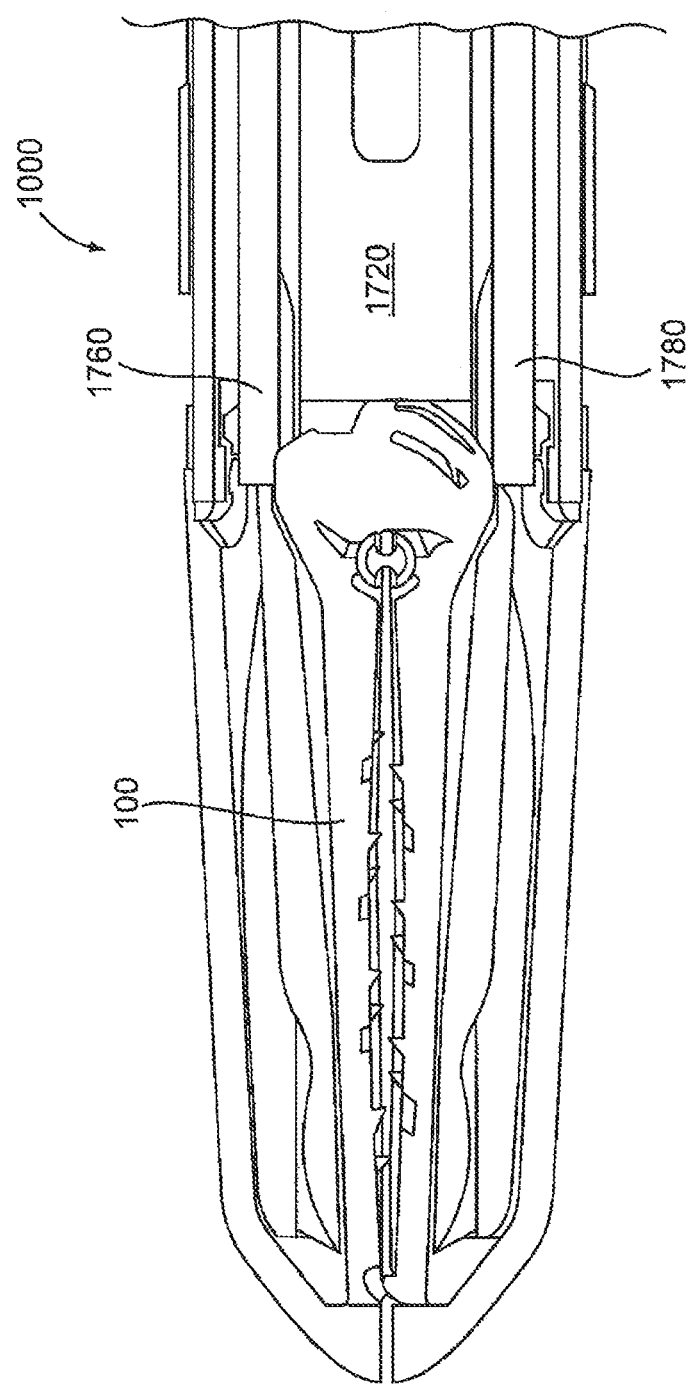
FIG. 51 shows wedges retract.

Once the clip is locked the wedges and catch begin to retract toward the proximal end of the applier shaft, see FIG. 51. Once they are fully retracted, see FIG. 52, the punch begins to retract toward the proximal end of the applier shaft, see FIG. 53. At this point the jaws can be opened and the clip is now free from the applier, see FIG. 54. At the same time the punch is quickly returned to its start position. The punch may be, but is not limited to being, spring loaded for the quick return. At this point, the punch is fully retracted and all parts are returned to their start positions, see FIG. 55.

In a second embodiment of the invention the wedges and catches are separate pieces attached to a catch tube, see FIGS. 60-63, and have the same forward actuation sequence as the first embodiment to lock the clip but does not require a dwell on the punch when the punch returns to the start position. In this embodiment the wedge and catch assembly stop just short of the clip stopping on the inner end surface of the jaws. The punch is then pushed forward to engage with the locking feature of the clip. The clip is first pushed out of the catch and wedges until the legs of the clip stop on the inner end surface of the jaws. The punch continues forward forcing the locking mechanism on the clip to rotate into the clip's locked position. During the rotation of the locking mechanism of the clip the legs are clamped together with the locking mechanism instead of the wedges as previously described. This embodiment also has internal leaf springs attached to the inner tube that bias the ends of the wedges together to open the clip during advance.

The proximal end of the applier, or applier handle, is made up of many parts that provide a user interface portion of the applier. Each of the distal end actuations are accomplished through the use of the proximal handle.

The handle has a two piece outer shell which stages the internal actuating components and provides a bearing surface for a multi stage transmission to allow 360° continuous rotation of the distal end. There is a two piece rotation knob clamped onto the distal portion of the multi stage transmission which is shaped to facilitate the 360° continuous rotation of the distal end.

Figure 65:
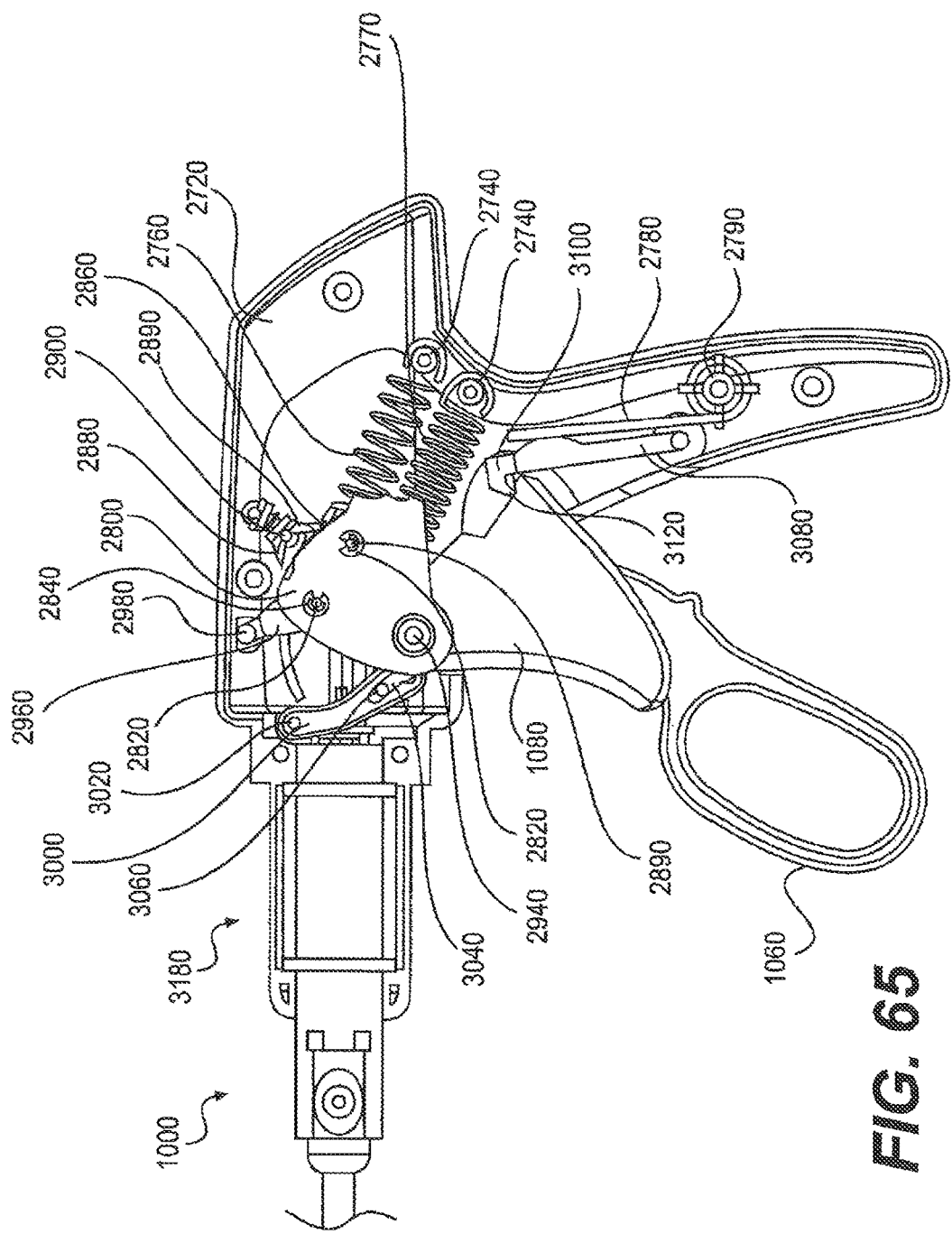
FIG. 65 shows a handle configuration (outer shell hidden).
Figure 66:
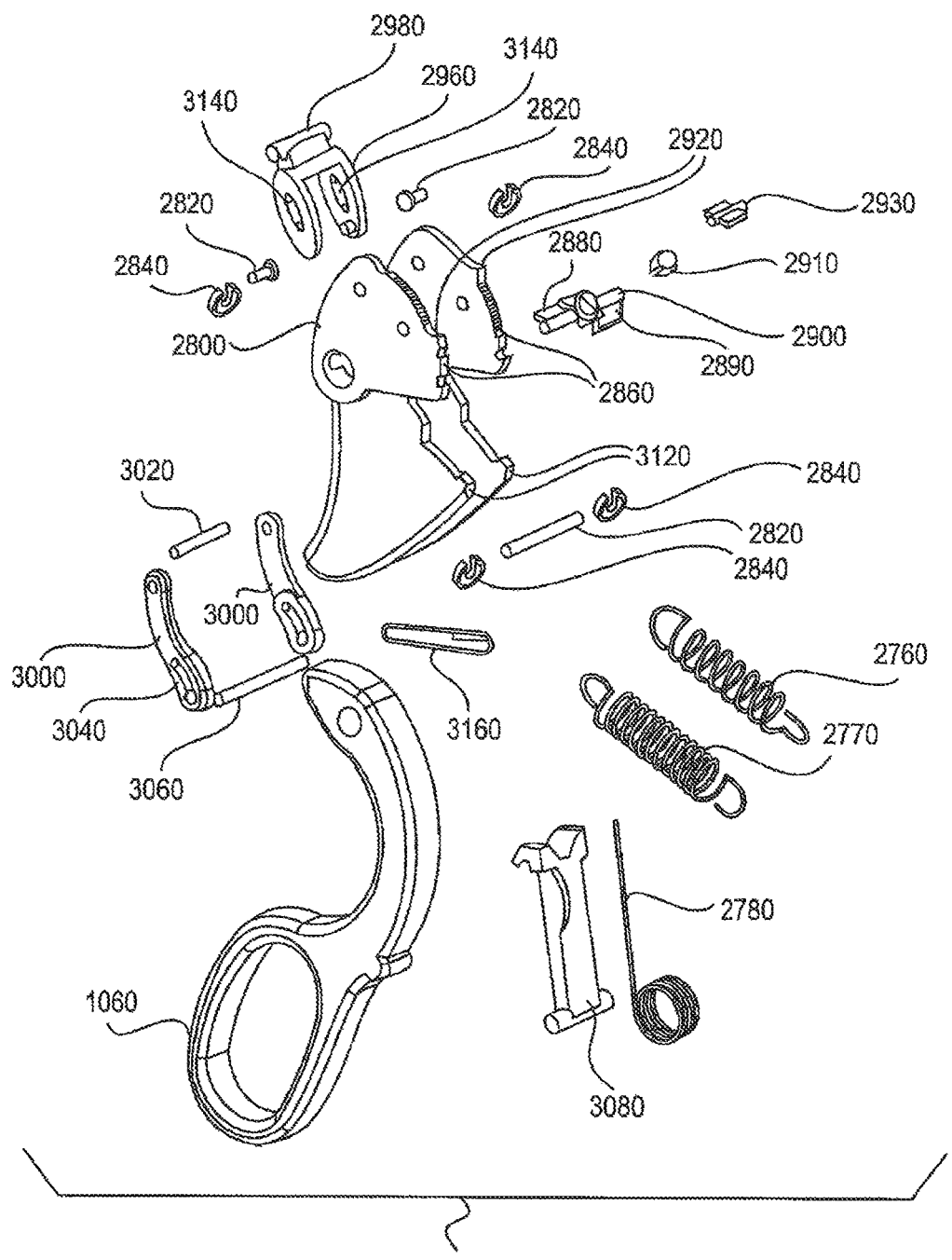
FIG. 66 shows trigger components.
Figure 67:
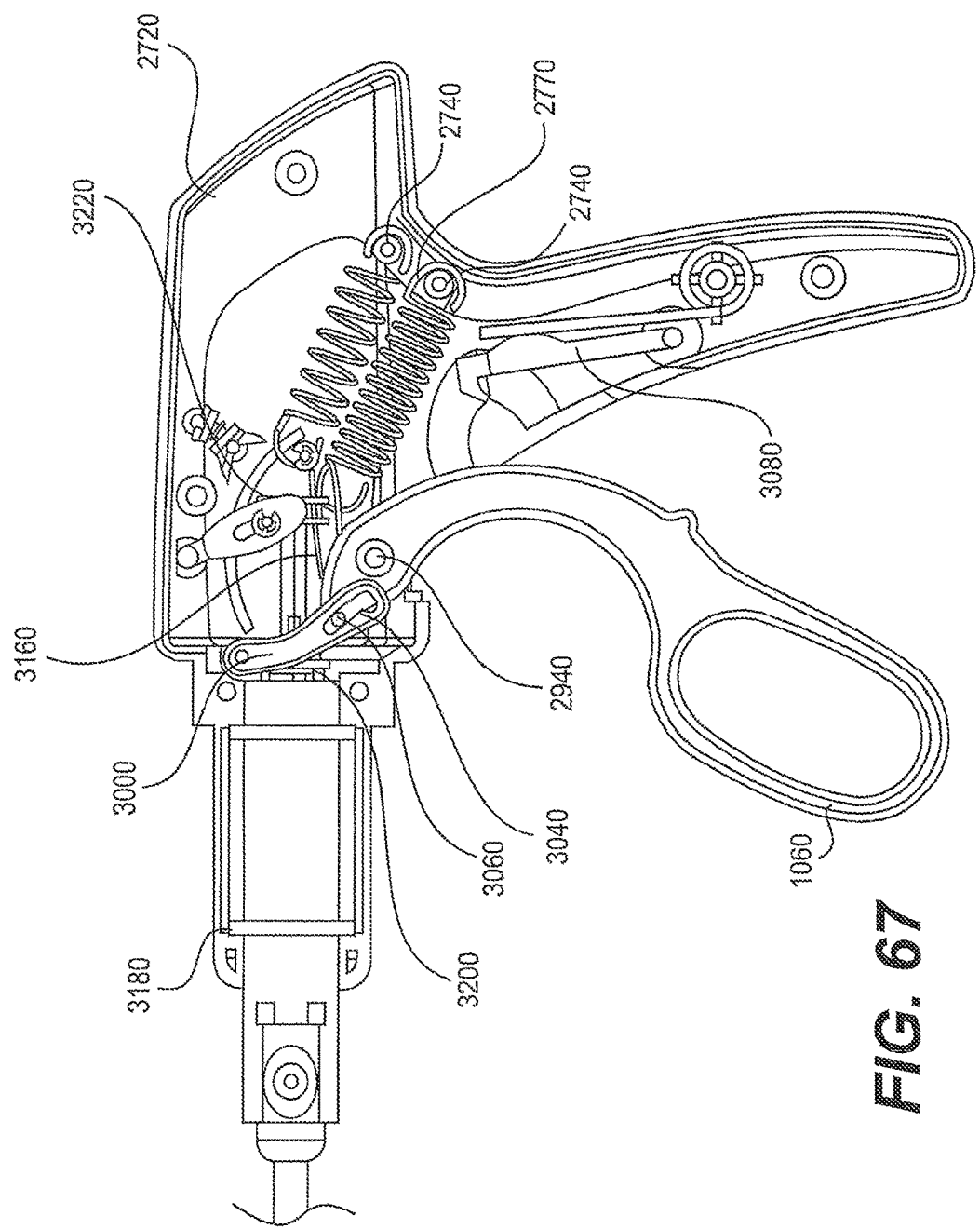
FIG. 67 shows a handle configuration (upper trigger hidden).

In one embodiment of the handle there are two triggers, both triggers rotate around the same centroid, see FIGS. 65-67. The lower trigger actuates the jaws and the upper trigger actuates the clip delivery sequence. The lower trigger is attached to the multistage transmission through two mirrored linkages which have features that allow the trigger to lock down when the jaws are closed. This feature is an over center cam. The linkages also have an inner profile which allows them to drive the section of the multistage transmission that actuates the jaws while allowing the 360° continuous rotation. The return stroke of the lower trigger is accomplished through a return spring attached to a cable that wraps around the front of the trigger and based on a pin at the proximal side of the handle. There is a interlock on the upper trigger that locks the upper trigger until the lower trigger is pulled and locked down to ensure a clip is not prematurely delivered. The upper trigger is attached to the multistage transmission through a linkage which has and inner profile that drives the section of the multistage transmission that actuates the clip delivery mechanisms and also allows the 360° continuous rotation. The return stoke of the upper trigger is accomplished through a return spring attached to the back side of the trigger and based on a pin at the proximal side of the handle. For both the actuation and return strokes there is a one way pawl that limits the direction of the upper trigger until a full stroke is completed, see FIGS. 65-68 for trigger and actuating components.

In a second embodiment of the handle, the trigger functions are reversed so that the upper trigger actuates the jaws and the lower trigger actuates the clip delivery mechanisms.

The distal portion of the applier is connected to the handle through the multi stage transmission, see FIGS. 65-68. One embodiment of the transmission is made up of a two piece outer shell which acts as the bearing to allow the rotation of the distal end. Internal to the shell are features that guide the internal components during the actuation sequences of the applier. There are two jaw links that connect to the inner tube of the distal end and provide the grove for the inner features of the lower trigger linkages. The jaw links snap together and ride on the internal surface of the transmission shell. The area between the jaw links is open to allow for additional transmission parts. There are two center spindles that snap together and attach to the wedges, the interior surface of the center spindles provide a guide for the spring loaded punch and the outer surfaces provide a guide for the catch pusher latch and the punch interlock. The catch pusher latch and the punch interlock move over the center spindles and are guided in slots on the outer shell of the transmission. Small pins move in and out of groves in the two pieces and the outer shell to achieve the appropriate timing for the clip delivery mechanisms in the shaft, see FIGS. 69-76 for the transmission assembly and FIGS. 77-86 for actuation sequence.

In a second embodiment of the transmission there is no punch latch interlock or return spring on the punch. The reduced movement of the wedges does not require a two stage pull back of the punch after the clip is locked. There is no requirement for the punch to dwell until the rest is pulled back because the clip is pushed out of the catch and wedges and released from the applier when the jaws are opened, see FIGS. 87-88 for a view of the second embodiment of the transmission and FIGS. 89-92 for the actuation sequence. A more detailed description of the apparatus shown in FIGS. 16-97 will follow with reference to reference characters and FIGS.

Figure 16:
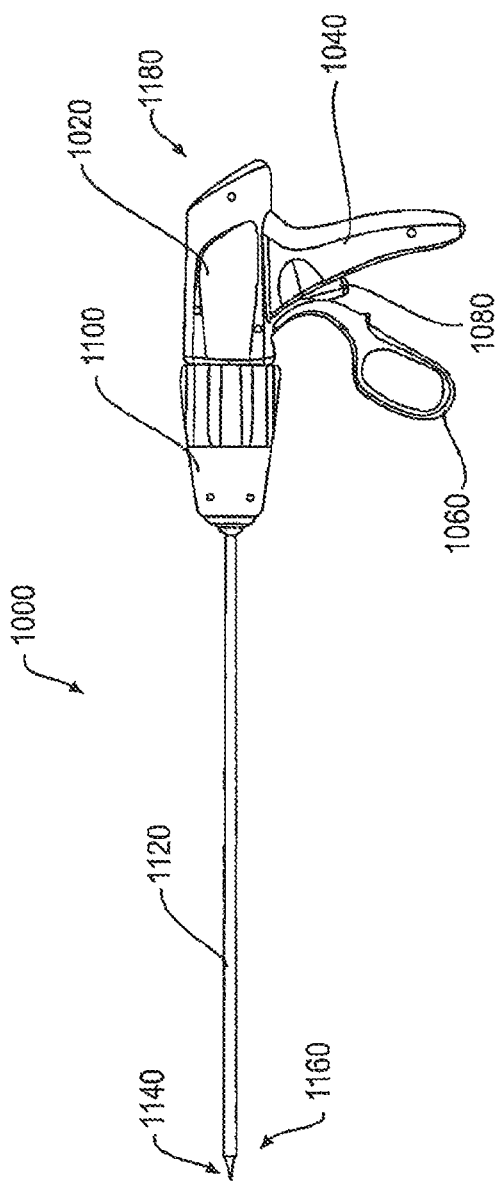
FIG. 16 shows a side view of an applier.

FIG. 16 is a side view of an applier 1000 in accordance with an embodiment of the invention. The applier 1000 has a clam shell housing 1020, a handle 1040, a jaw trigger 1060, and a ligate trigger 1080. A jaw trigger 1060 and ligate trigger 1080 are actuated by pulling the triggers 1060 and 1080 toward the handle 1040. Applier 1000 also includes a shaft 1120 which carries the jaws 1140 on the distal end 1160, which is opposite from the proximal end 1180.

Figure 17:
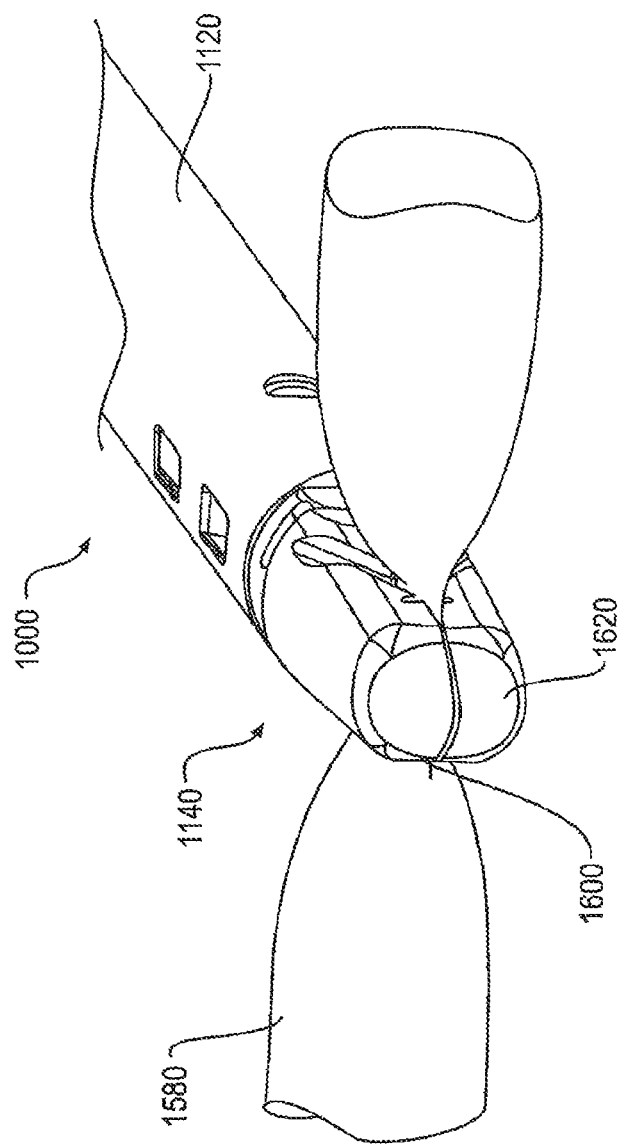
FIG. 17 shows an applier clamped on vessel.

FIG. 17 is a partial isometric view of the applier 1000 clamped onto a blood vessel 1580 or other tissue 1580. The jaws 1140 have clamped onto and deformed the vessel 1580. The portion of the shaft 1120 is also shown carrying the top jaw 1600 and the lower jaw 1620 which together comprise the jaws 1140.

Figure 18:
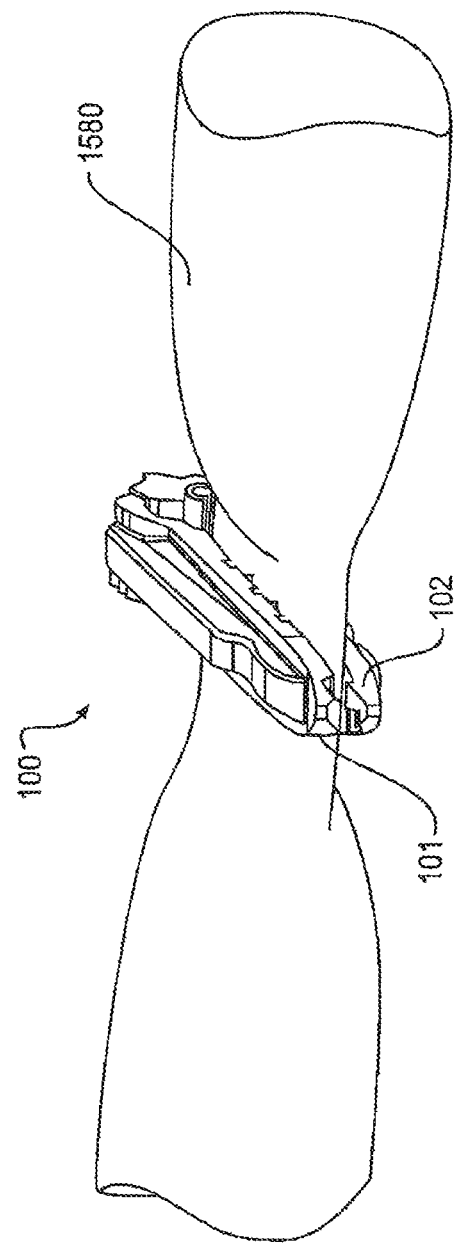
FIG. 18 shows an isometric view of clip latched on vessel.

FIG. 18 is an isometric view of a clip 100 clamped onto a blood vessel 1580 or tissue 1580. The clip 100 is in a clamping position and is attached to the vessel/tissue 1580. The top leg or first leg 101 is shown above the second or bottom leg 102.

FIG. 19 is a side view of a clip 100 clamped onto a vessel 1580 or tissue 1580. The clamp 100 includes a top first leg 101 above the bottom or second leg 102. The locked locks the first leg 101 and the second 102 is accomplished by locking the buttress body 150. The buttress body 150 has moved to a position where the first rounded surface 148 is fit into a first recess groove 158. Further, the protruding surface 156 is fit within the second recessed groove 146. The first living hinge 1400 is deformed to allow a first rounded surface 148 and second protruding surface 156 to fit into the first recess groove 158 and second recess groove 146 respectively. The second living hinge 162 is deflected to permit the detent 157 to fit within the notch 147 as shown in a locking manner, thereby keeping the first leg 101 clamped and nearly in contact with the second leg 102.

FIG. 20 is a side view of several of the parts used in the clamp applier 1000. These parts are for the most part only partially shown and shown in a disassembled state. A top jaw 1600 and the bottom jaw 1620 are shown. The outer tube 1640 and the inner tube 1660 are also shown. The wedges 1680 including the top the wedge 1760 and bottom wedge 1780 are also shown. The catch 1700 is shown as well as the punch 1720. At the bottom of FIG. 20, the clip indicator 1740 is shown.

FIG. 21 is a partial isometric view of the wedges 1680, specifically the top wedge 1760. In many embodiments in accordance with the invention, the top wedge 1760 is a mirror image of the bottom wedge 1780 and that the bottom wedge 1780 may be similar to the top wedge 1760 only placed in an in inverted position as shown in FIG. 20. Turning to FIG. 21, the top wedge 1760 includes a thicker portion 1820, thicker portion 1820 may include a slanted surface 1840 which provides a transition between a thicker portion 1820 and the standard portion of the top wedge 1760. In some embodiments of the invention and as shown FIG. 21 the wedges 1680 may have a U-shaped cross-section resulting in a channel 1850. At the proximal end 1880 of the wedge 1760 a bracket 1860 may be attached. The purpose of the bracket 1860 will be discussed in more detail later below.

Figure 22:
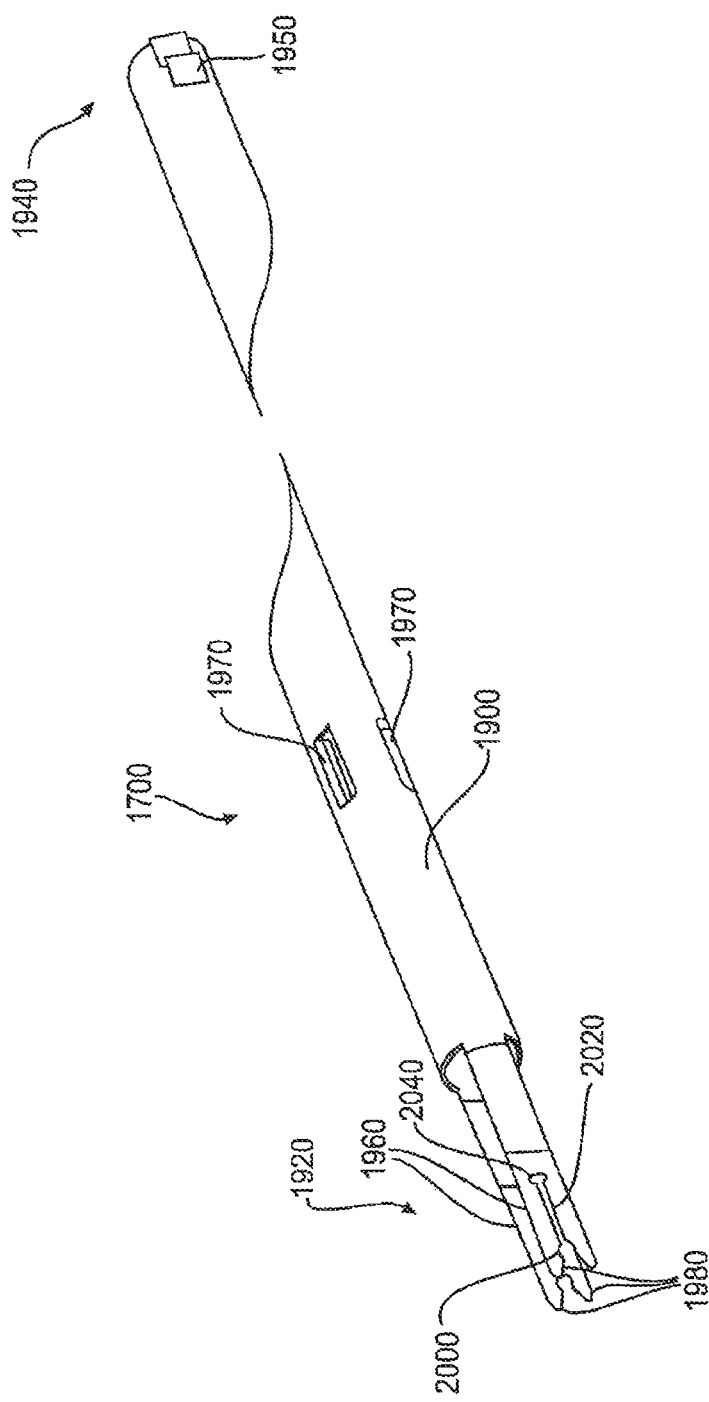
FIG. 22 shows a catch.

FIG. 22 is a partial isometric view of catch 1700 in accordance with some embodiments of the invention. The catch 1700 may include a shaft portion 1900. At the distal end 1920 of the catch 1700 there may be forked ends 1960 of the catch 1700. The fork end 1960 may include a slot 2020. The slot 2020 may start with a rounded cut out portion 2000 and terminate with a second cut out portion 2040. The forked work end 1960 may start with slanted surfaces 1980, but the proximal end 1940 of the catch 1700 there may be an attached bracket 1950 which will be shown in additional figures and discussed in more detail later below. The catch 1700 may also include guides 1970.

Figure 23:
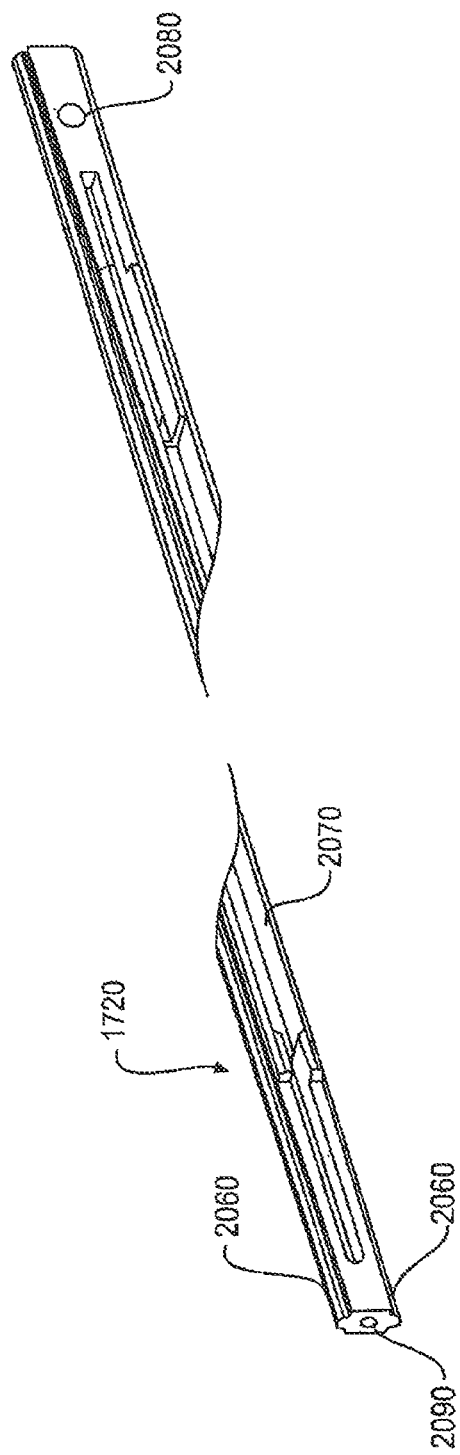
FIG. 23 shows a punch.

FIG. 23 is a partial isometric view of the punch 1720. The punch 1720 may include projections 2060 which project up from the punch 1720 at the top and bottom. As shown in FIG. 23, the punch 1720 may also have a longitudinal hole 2090 at the end as shown. The punch 1720 may also include a slot 2070 and a hole 2080 located at the opposite end of the punch 1720 and the longitudinal hole 2090.

Figure 24:
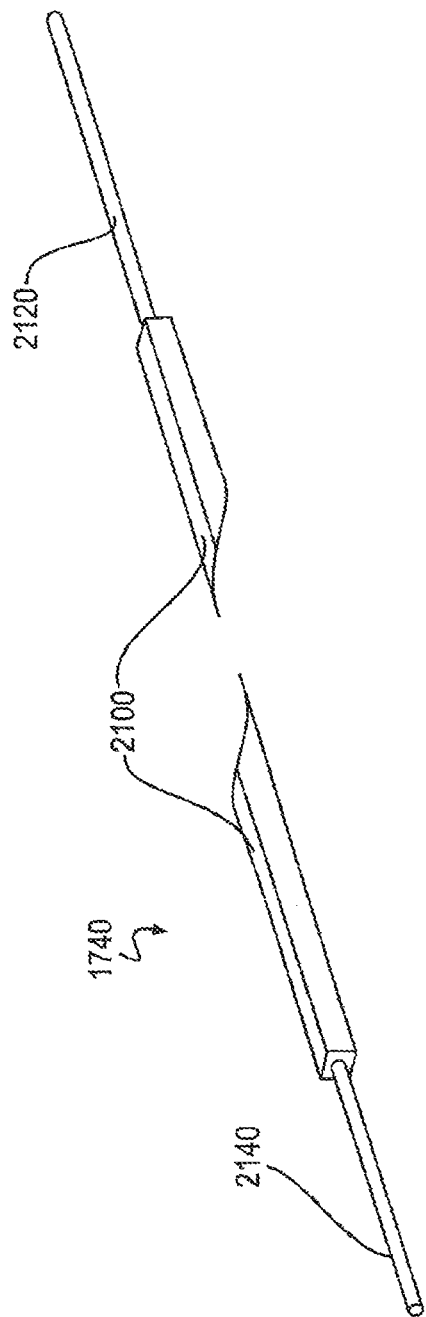
FIG. 24 shows a clip indicator.

FIG. 24 is a partial isometric view of a clip indicator 1740. The clip indicator 1740 may include a rectangular portion 2100 and a distal cylindrical portion 2140 and a proximal cylindrical portion 2120 located on the opposite side of the rectangular portion 2100.

FIG. 25 is a partial isometric view of an inner tube 1660 in accordance with some of the embodiments of the invention. The inner tube 1660 may include a viewing port or a pair of viewing ports 2180. The inner tube 1660 at the front end as oriented in FIG. 25 may include a T-shaped structure 2200 located on both the top and the bottom as oriented in FIG. 25 of the inner tube 1660 and U-shaped grooves 2220 on both the right and left side is oriented in FIG. 25 of the inner tube 1660. The inner tube 1660 may also include a longitudinal running slit 2230. On the opposite end of the inner tube 1660 and the T-shape structures 2200 may be a bracket 2160 located on the approximate end of the inner tubes 1660. The bracket 2160 may be shown in later figures and discussed in additional details later below.

FIG. 26 is a side view of the jaws 1140. Atop jaw 1600 is located above the bottom jaw 1620 as shown in FIG. 26. Both the top 1600 and bottom 1620 jaws may include grooves 2240. The jaws 1140 may include T-shape structure holes 2250 configured to accommodate and have T-shaped structure 2200 as shown and described in FIG. 25, as shown also in FIG. 26. FIG. 26 also shows the first portion of the inner tube 1660 in the U-shaped groves 2220 as described with respect to the inner tube 1660 in FIG. 25.

FIG. 27 is a partial close up view of a portion of FIG. 26. In FIG. 27, the top jaw 1600 is shown with the T-shape structure 2200 of the inner tube 1660. The T-shape structure 2200 is shown in the T-shape structure hole 2250. The T-shape structure hole 2250 has a geometry that allows the jaws 1140 to open and close while the T-shape structure 2200 remains within the T-shape structure holes 2250. The top jaw 1600 also has a caming surface 2280 that cams against a caming surface 2260 of the inner tubes 1660 as the jaws 1140 opens and closes. While only a partial close-up view of the top jaw 1600 is shown, one of ordinary skill in the art will understand that the bottom jaw 1520 is similarly configured in a mirror type image fashion. The top jaw 1600 also engages a bottom jaw 1620 at a push point 2300 when the jaws 1140 open and close.

FIGS. 28*a*, 28*b* and 28*c* are isometric top and bottom views of the top jaw 1600. The top jaw 1600 includes the T-shape structure hole 2250, hinge pin 2620 and hinge pin cap 2630 as shown in the various views. In some instances, in the FIGS. the hinge pin cap 2630 has been removed to expose the hinge pin 2620.

FIG. 29 is a partial isometric view of the outer tube 1640. The outer tube 1640 may include a viewing port 2320, spring legs 2420 which in some embodiments bias the wedges 1680 to a radially inward position. The outer tube 1640 may also include eye brackets 2340 having holes 2400. The eye brackets 2340 and holes 2400 may be used for attaching the jaws 1140. Inner tube 1640 also includes a shaft portion 2360 and a rim 2380 located at the end of the shaft 2360.

FIG. 30 is a partial isometric view of the applier 1000 in a partially assembled state. As shown in FIG. 30, an outer tube 1640 with the jaws 1140 comprising of the top jaw 1600, the lower jaw 1620. The jaws 1140 contain the clip 100. The catch 1700 is located behind the clip 100. The punch 1720 is shown along with the hole 2090 in the end of the punch 1720. The distal cylindrical portion 2140 of the clip indicator 1740 is shown, located in the slot 2070.

FIG. 31 is a partial isometric view of the applier 1000 where some of the outer portions removed so the inner portions can be shown. The applier 1000 includes the outer tubes 1640, the wedges 1680 are shown inside the outer tubes 1640. Within the wedges 1680, the punch 1720 is shown, the slot 2070 is shown with the rectangular portion 2100 fit into the slot 2070 from the punch 1720. A spring 2440 is located forward of the rectangular portion 2100. A hole 2080 in the punch 1720 is shown with a pin 2460 located in the hole 2080. The top wedge 1760 and bottom wedge 1780 are also shown along the brackets 1860 attached to the top wedge 1760 and bottom wedge 1780.

Figure 32:
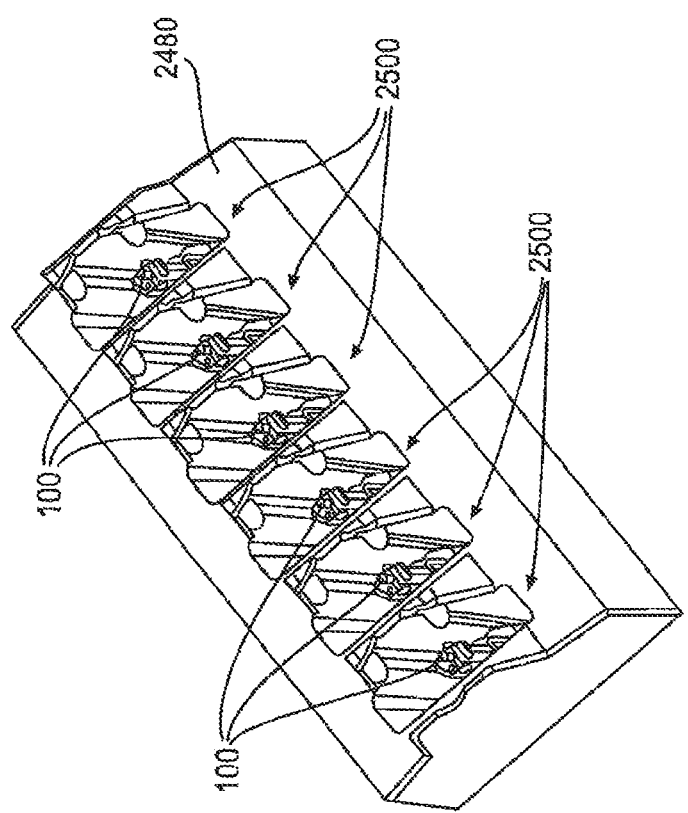
FIG. 32 shows loaded clips in cartridge.

The manual applier 1000 attains the clip 100 from a cartridge 2480 as shown in FIG. 32. The clips 100 are removed from the cartridge ports 2500 and the cartridge 2480 and placed into the applier 1000. The loading process will be illustrated in FIGS. 33-38.

Figure 33:
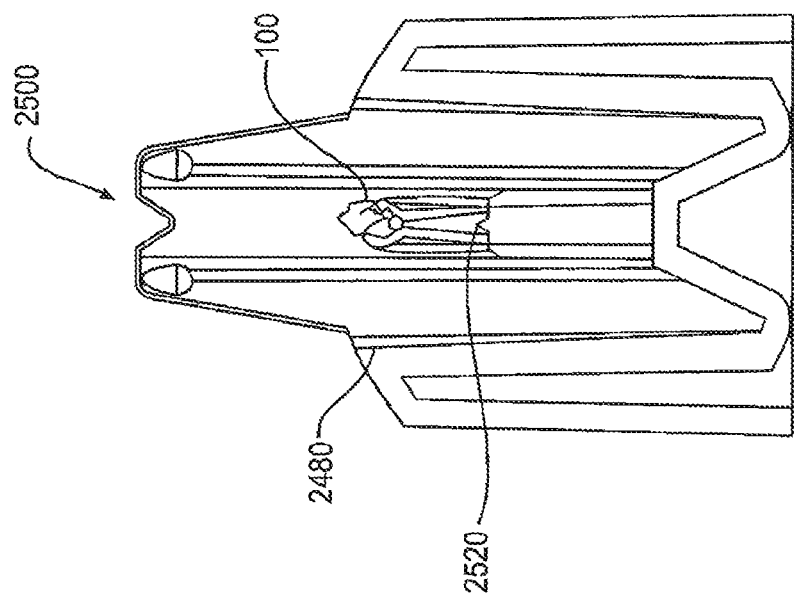
FIG. 33 shows a cross section view of loaded clip.

In FIG. 33 a cross-sectional view of the cartridge 2480 is shown. The cartridge ports 2500 is shown having a clip 100 inside the cartridge port 2500. A detent 2520 holds the cartridge 100 within the cartridge port 2500.

Figure 34:
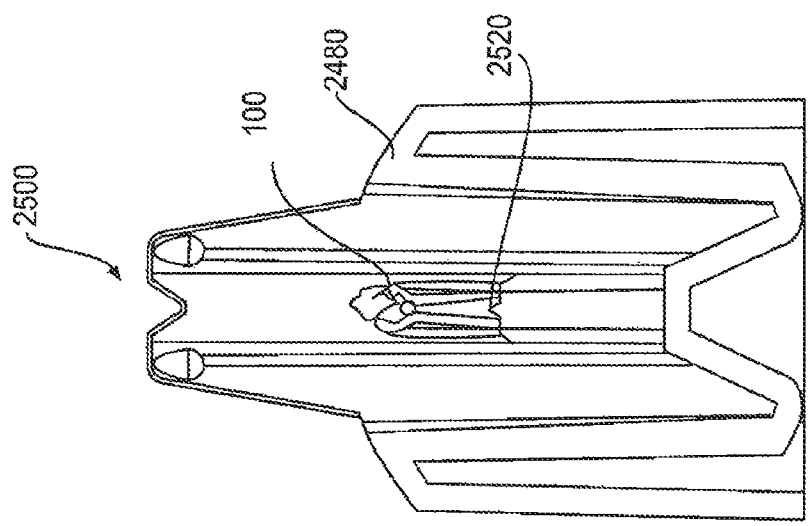
FIG. 34 shows clip legs held by detents in cartridge.

FIG. 34 is a cross-sectional view of the cartridge 2480 showing the detent 2520 securing the cartridge 100 within the cartridge port 2500.

Figure 35:
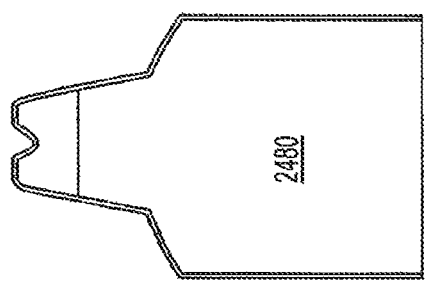

FIG. 35 is an end view of the cartridge 2480.

Figure 36:
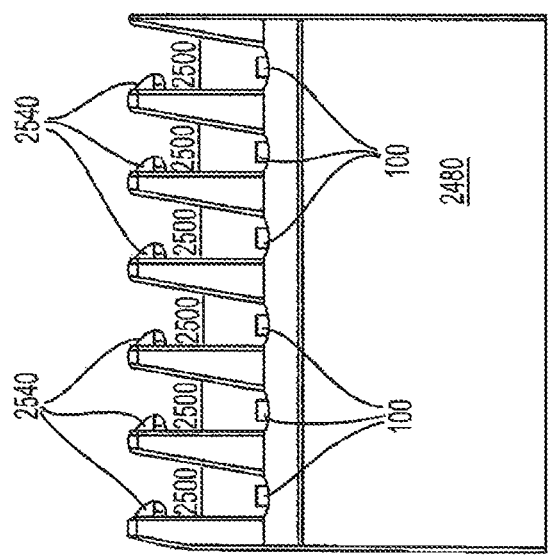
FIGS. 35 and 36 shows a clip cartridge.

FIG. 36 is a side view of the cartridge 2480 showing the cartridges 100 located in the cartridge port 2500. Protrusions 2540 are also shown on the cartridge 2480.

FIG. 37 is a partial cross-sectional view of cartridge 2480, showing the applier 1000 approaching the cartridge 2480 in order to obtain clip 100 from the cartridge 2480. The jaws 1140 of the applier 1000 are open and approaches the cartridge port 2500 in order to obtain a cartridge 100.

FIG. 38 is a cross-sectional view of a cartridge 2480 where the applier 1000 as entered the cartridge port 2500 in order to obtain a clip 100. The applier 1000 has moved into the cartridge port 2500. The jaws 1140 have entered the jaw channels 2560 and the clip 100 is now inside the applier 1000.

FIG. 39 is a partial cross-sectional view of the applier 1000 as it approaches the clip cartridge 2480. The jaws 1140 are in an open position. The inner tube 1660 has moved to a forward position causing jaws 1140 to open. The catch 1700 is in a position ready to receive the clip 100 (not shown in FIG. 39).

Figure 40:
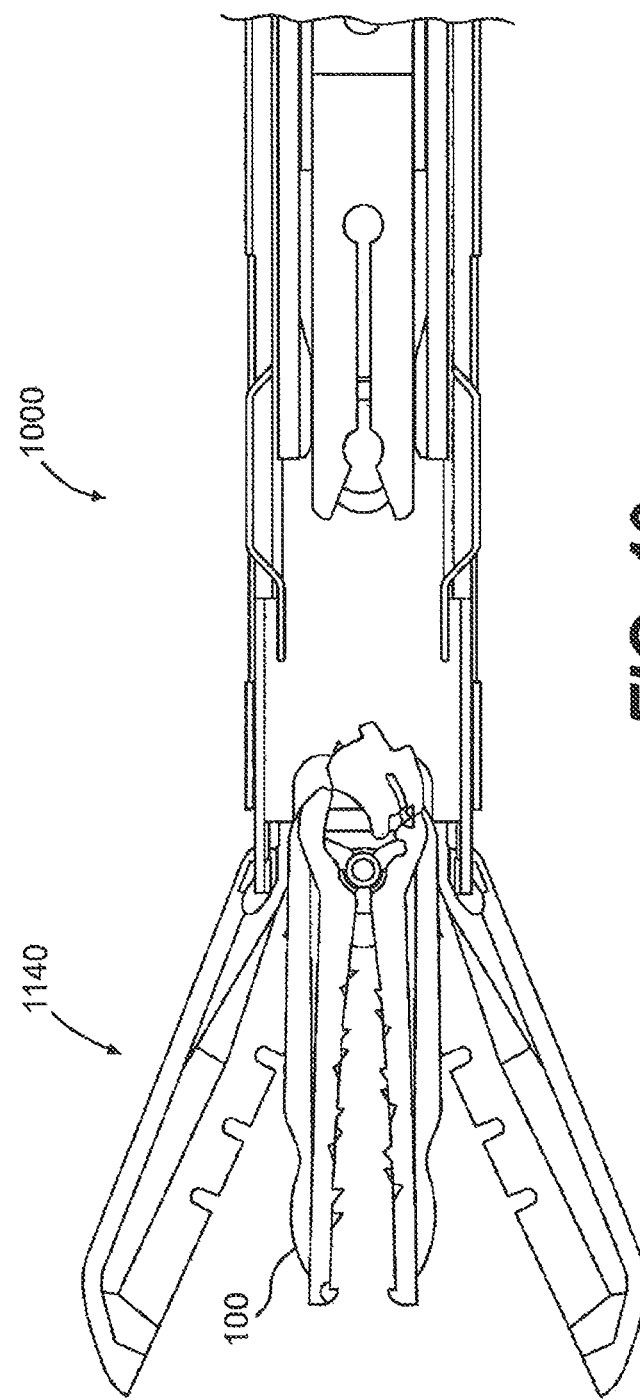
FIG. 40 shows a clip load (cartridge not shown).

FIG. 40 is a partial cross-sectional view of the applier 1000 as it loads the clip 100. The cartridge has not been shown for clarity. The jaws 1140 are in an open position. While the clip 100 is shown in a closed position, in reality the standard position for some clip in accordance with the invention and as should be shown in FIG. 40 is in a slightly open position, not fully opened and not fully closed. In other embodiments of the invention, the clip 100 may be in other positions.

FIG. 41 is a partial cross-sectional view of the applier 1000 with a clip 100 lowered inside. The distal cylindrical portion 2140 of the clip indicator 1740 is in contact with the buttress body 150 of the clip 100.

FIG. 42 is a partial cross-sectional side view of the applier 1000, showing the clip inside the applier 1000 and the jaws 1140 closed.

Figure 43:
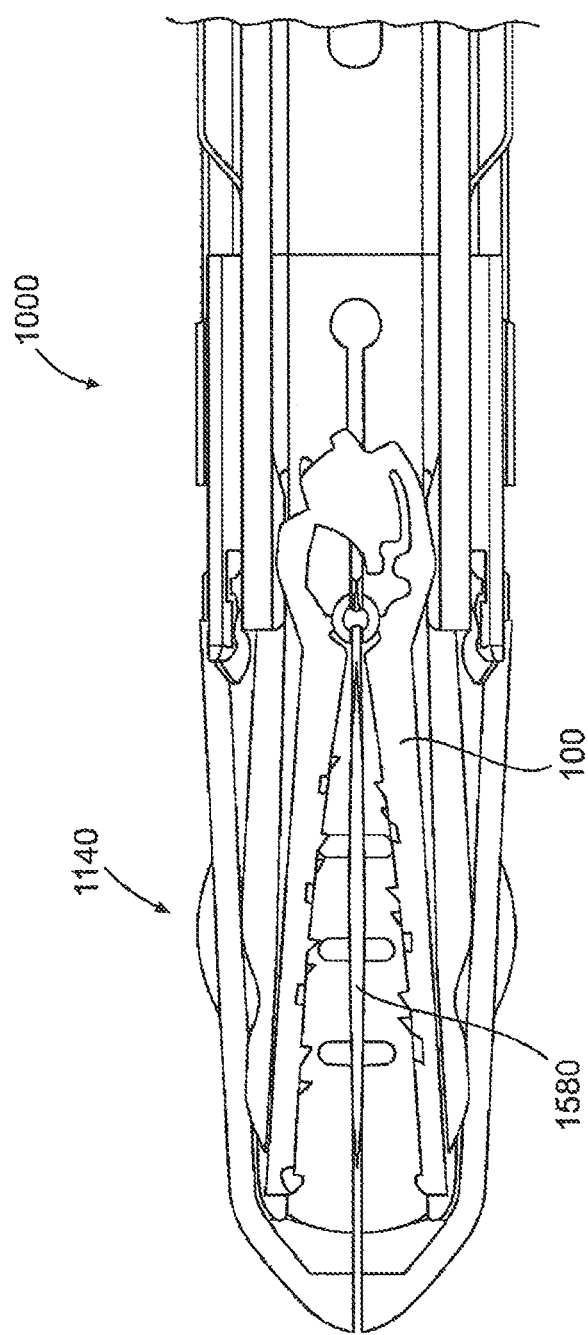
FIG. 43 shows a clip advance into jaw over vessel.

FIG. 43 is a close up view of the jaws 1140 of the applier 1000, showing that the jaws 1140 have closed over a vessel or tissue 1580. The clip 100 is starting to advance into the jaws 1140.

Figure 44:
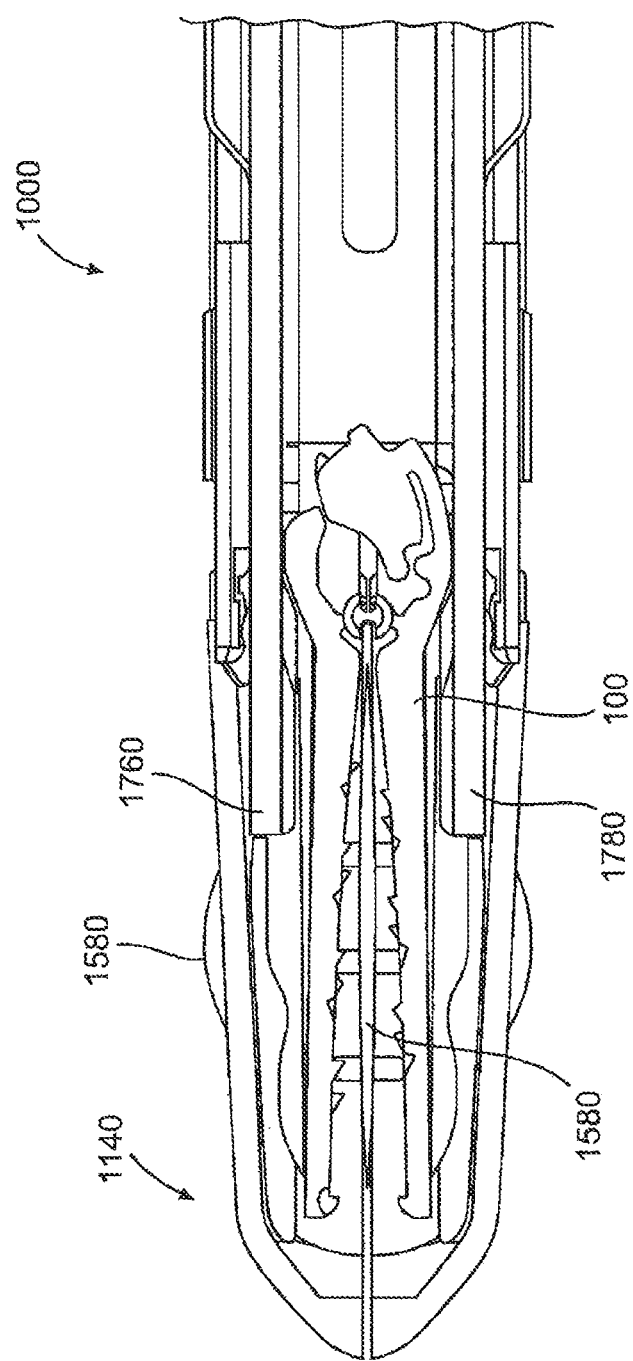
FIG. 44 shows a clip advanced over vessel wedges begin to advance.

FIG. 44 is a close up cross-sectional partial view of the applier 1000 showing the jaws 1140 clamped or a vessel or tissue 1580. The clip 100 has advanced into the jaws 1140 and the wedges 1760 and 1780 have started to move into the jaws 1140.

Figure 45:
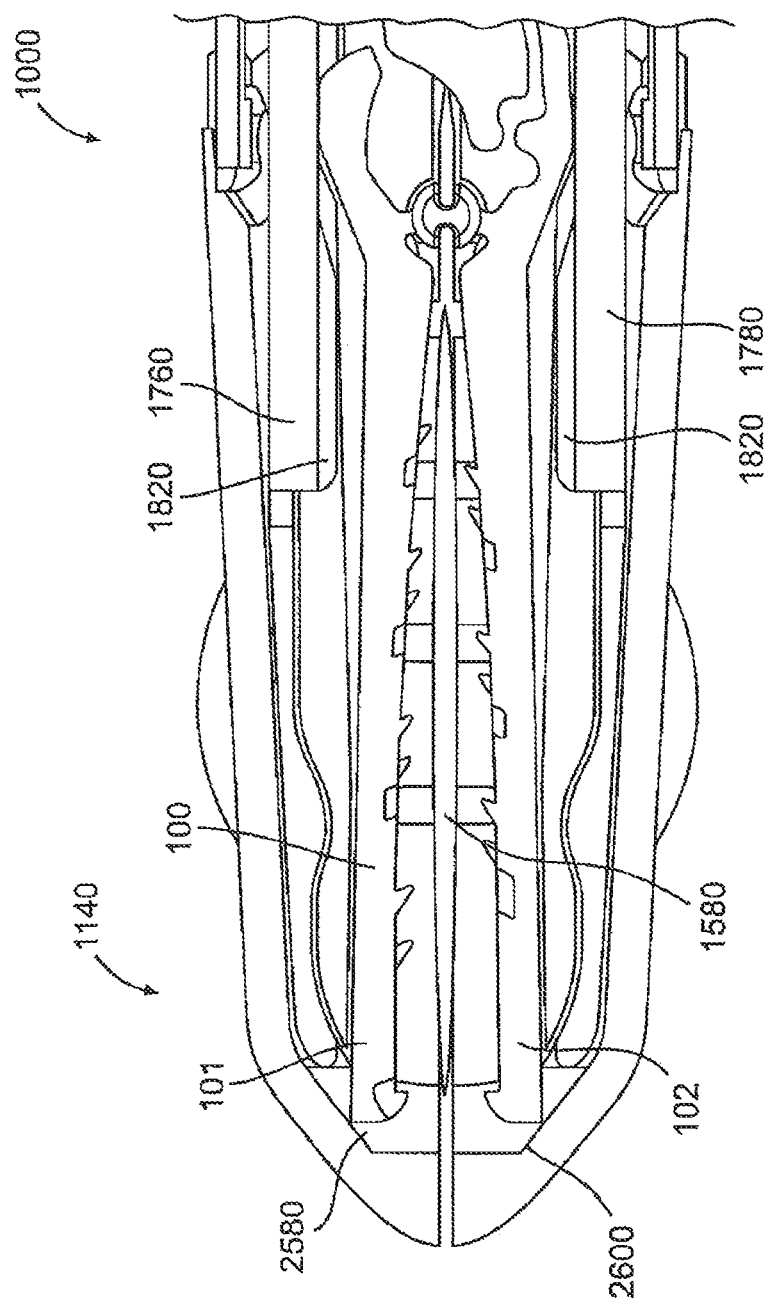
FIG. 45 shows wedges advance to close clip.

FIG. 45 is a partial cross-sectional view of the jaws 1140 of the applier 1000 showing the clip 100 has advanced into jaws 1140. The vessel or tissue 1580 is currently being clamped by the jaws 1140 but not the clip 100. The upper leg 101 of the jaw 100 is contacting the inner slanted surface 2580 and the lower leg 102 is contacting the inner slanted surface 2600 of the jaws 1140. The wedges 1760 and 1780 continue to advance to close the clip 100, the thick portions 1820 have moved into the jaws 1140 sufficient so that as the punch continues to urge on the clip 100, the thick portions 1820 will not be in the way of the legs 101 and 102 of the clip 100 from shutting.

Figure 46:
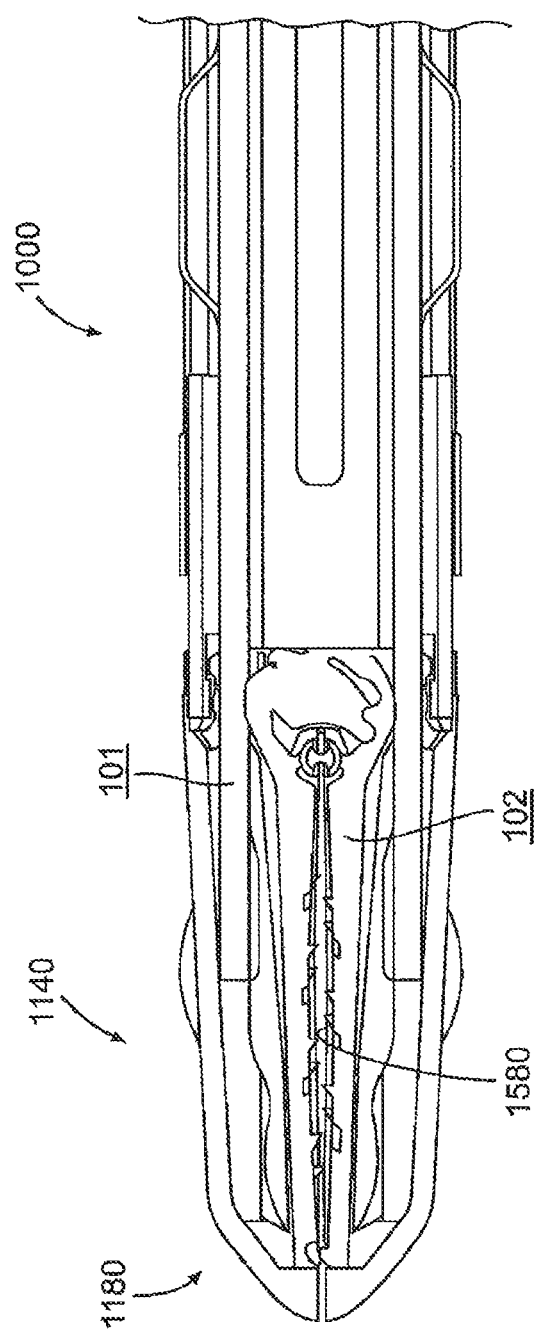
FIG. 46 shows a punch latches clip on vessel.

FIG. 46 is a partial cut away of the applier 1000 and the jaws 1140, where the leg 101, the lower leg 102 have closed to clamp onto the vessel or tissue 1580.

Figure 47:
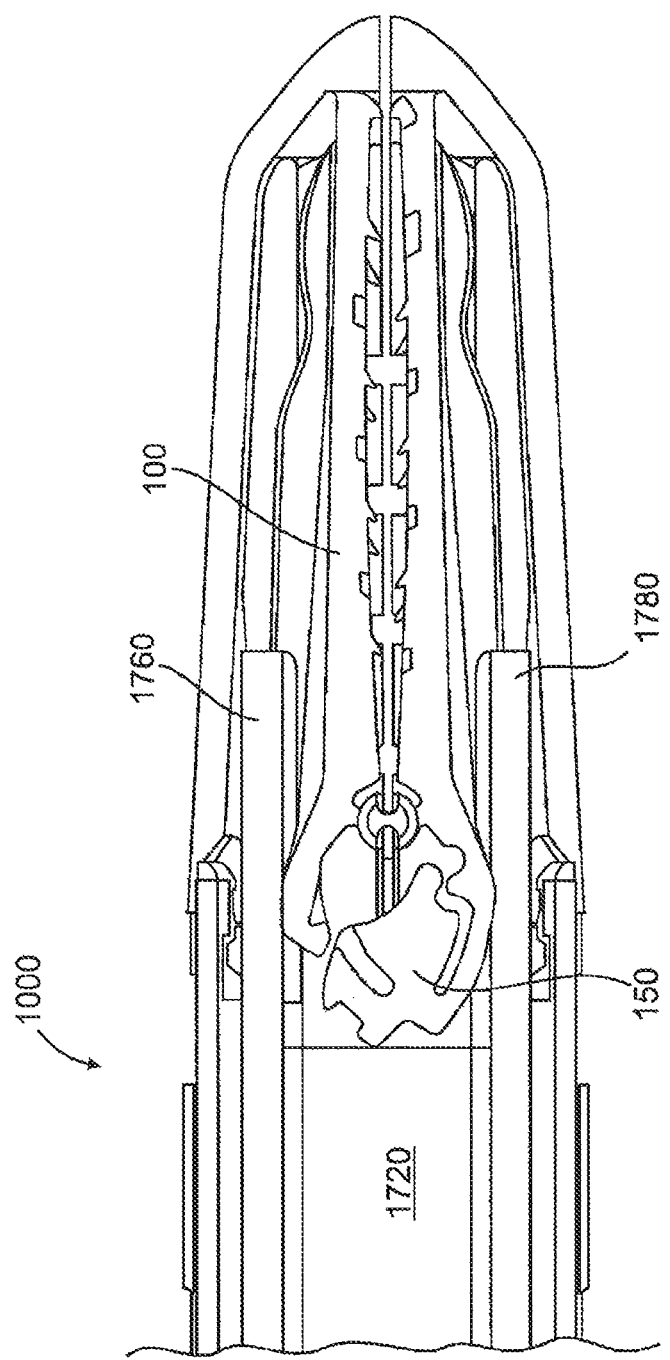
FIG. 47 shows a punch moves up to buttress.

As best shown in FIG. 47, the punch 1720 pushes the clip 100 forward and continues to push against the buttress body 150 to cause the clip 100 to lock in a clamping position. As shown in FIG. 47, the wedges 1760 and 1780 have advanced far enough to not prevent the clip 100 from locking.

Figure 48:
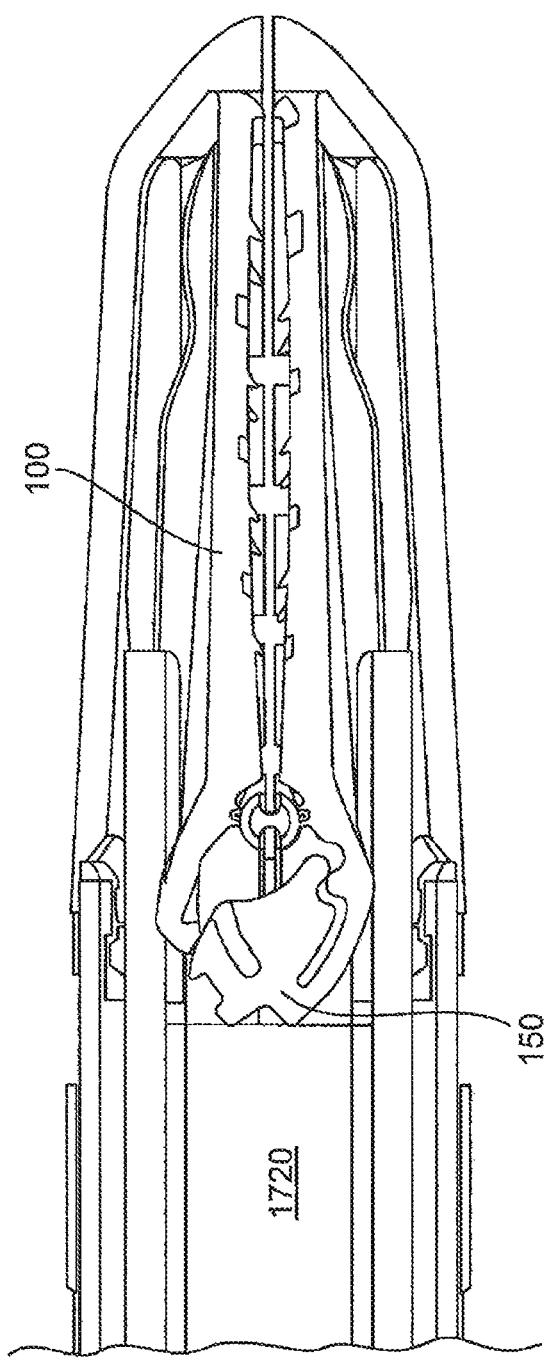
FIG. 48 shows a buttress rotating as the punch moves forward.

FIG. 48 illustrates punch 1720 continuing to move the buttress body 150 toward a latching position on the clip 100.

Figure 49:
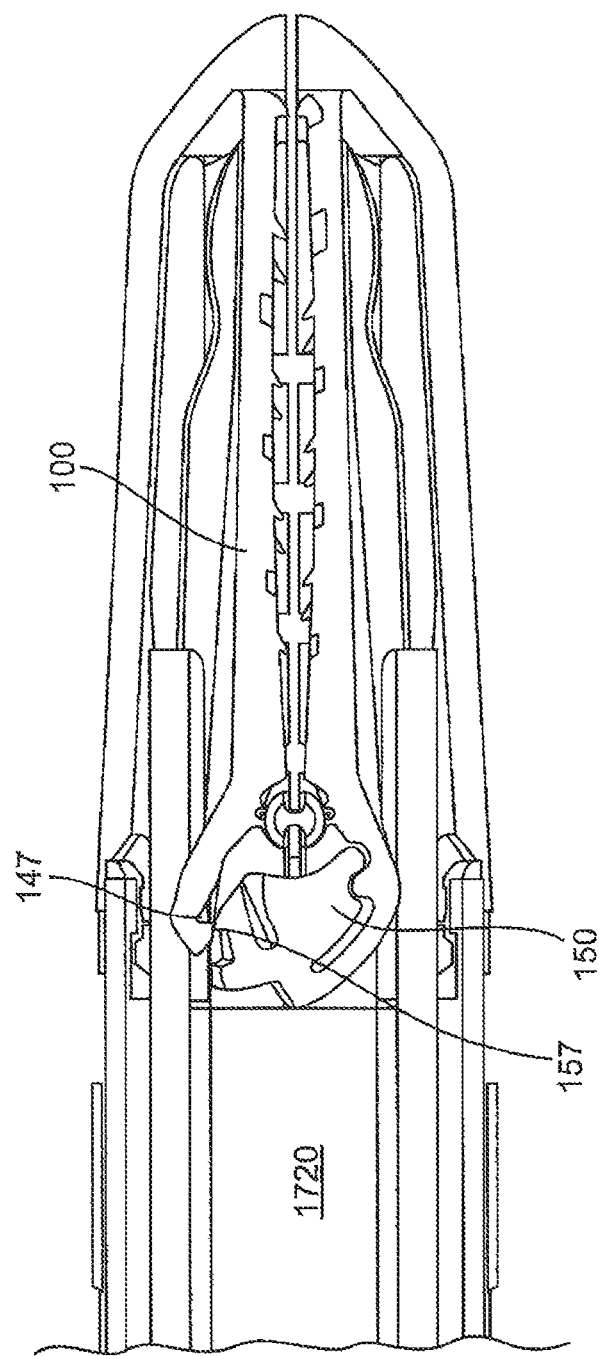
FIG. 49 shows a clip just before latch.

FIG. 49 shows the punch 1720 continuing to move the buttress body 150 so that the detent 157 moves towards the notch 147 and the clip.

Figure 50:
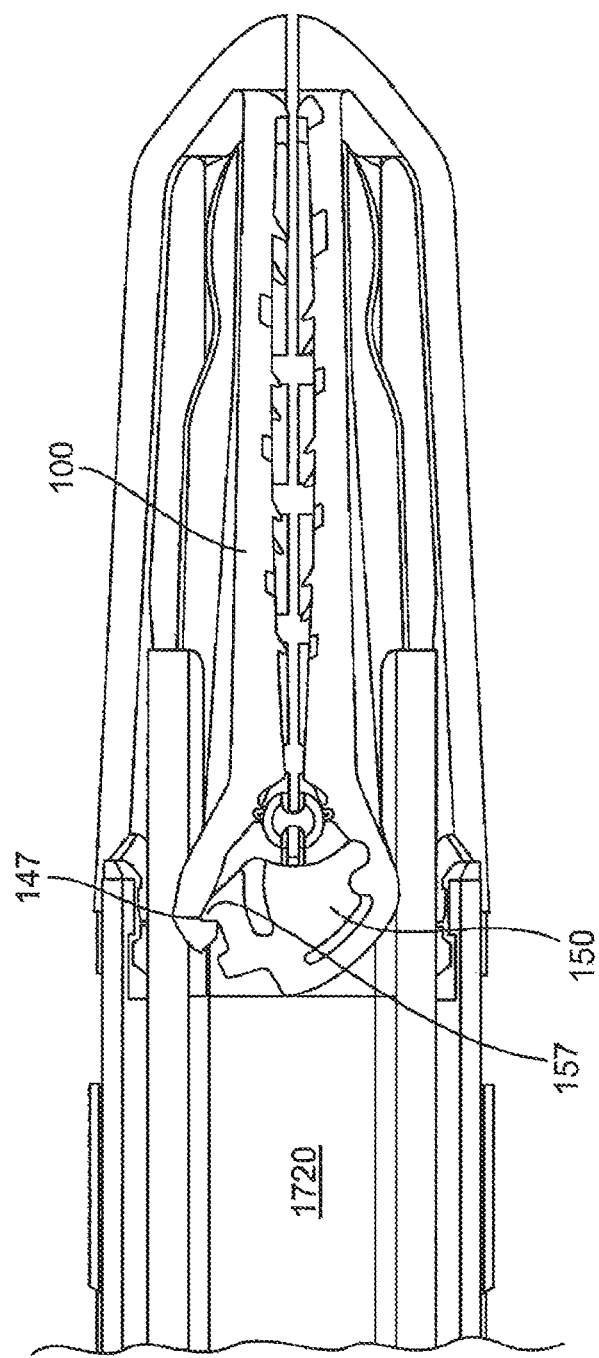
FIG. 50 shows a clip locked.

FIG. 50 shows the punch 1720 moving the buttress body 150 sufficiently forward such that the detent 157 is locked into the notch 147, thereby locking the clip 100 in a closed position.

FIG. 51 shows the wedges 1760 and 1780 retracting into the applier 1000 leaving the clip 100 in place.

Figure 52:
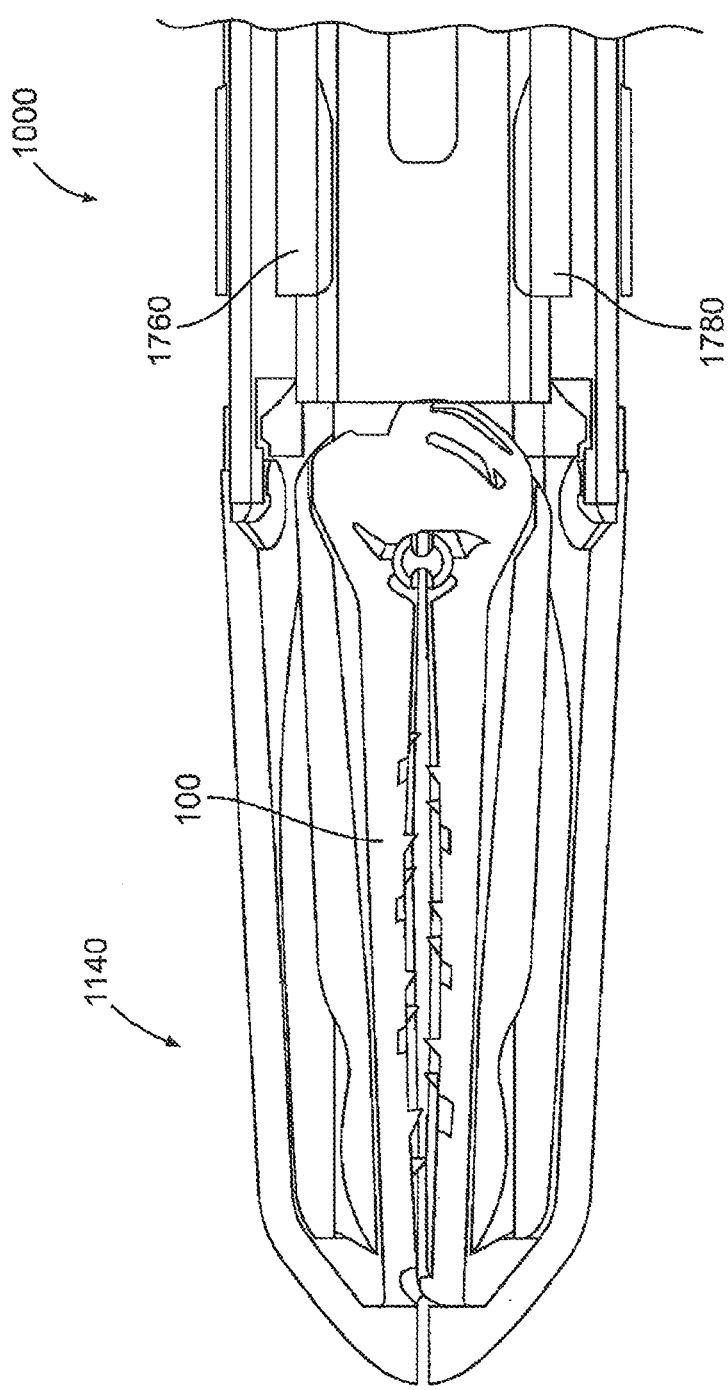
FIG. 52 shows wedges fully retracted.

FIG. 52 shows the wedges 1760 and 1780 in a fully retracted position within the applier 1000 and the clip 100 in place in the jaws 1140.

Figure 53:
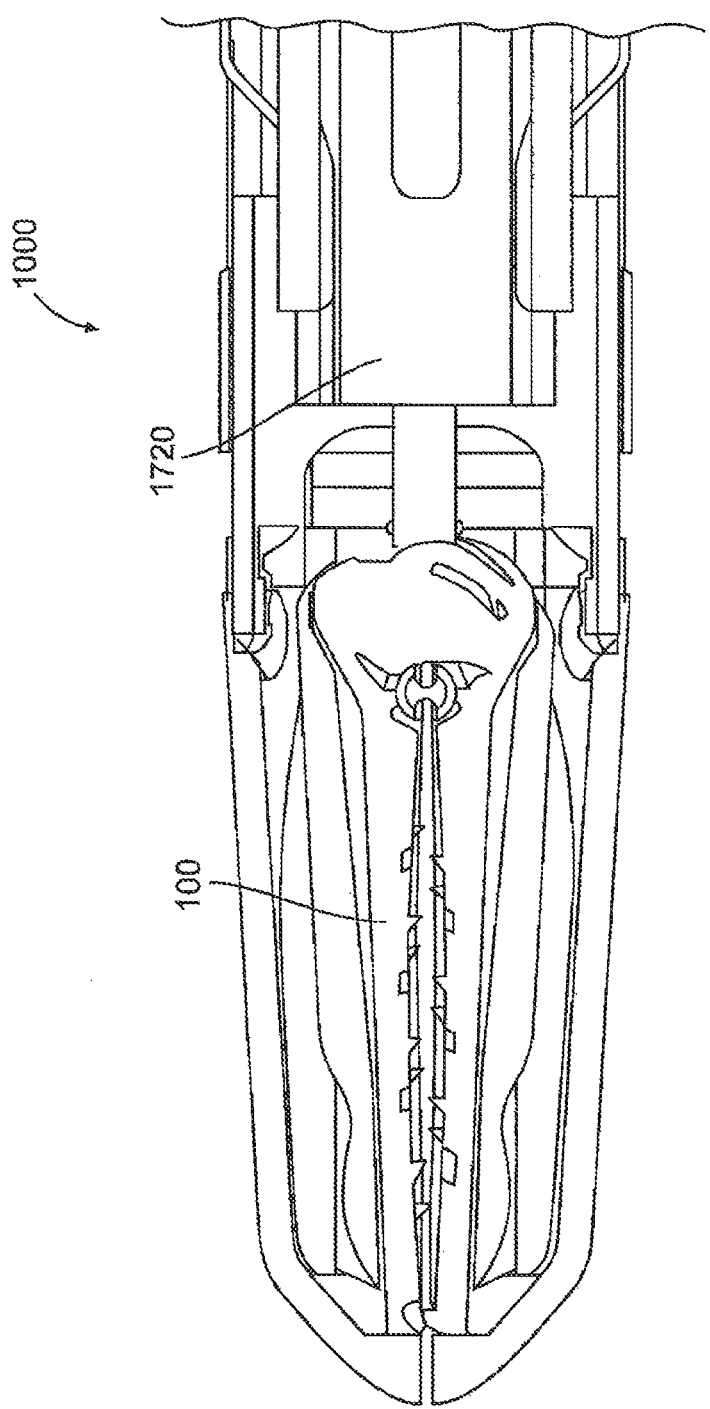
FIG. 53 shows a punch retracting.

FIG. 53 shows the punch 1720 retreating away from the clip 100 into the applier 1000.

Figure 54:
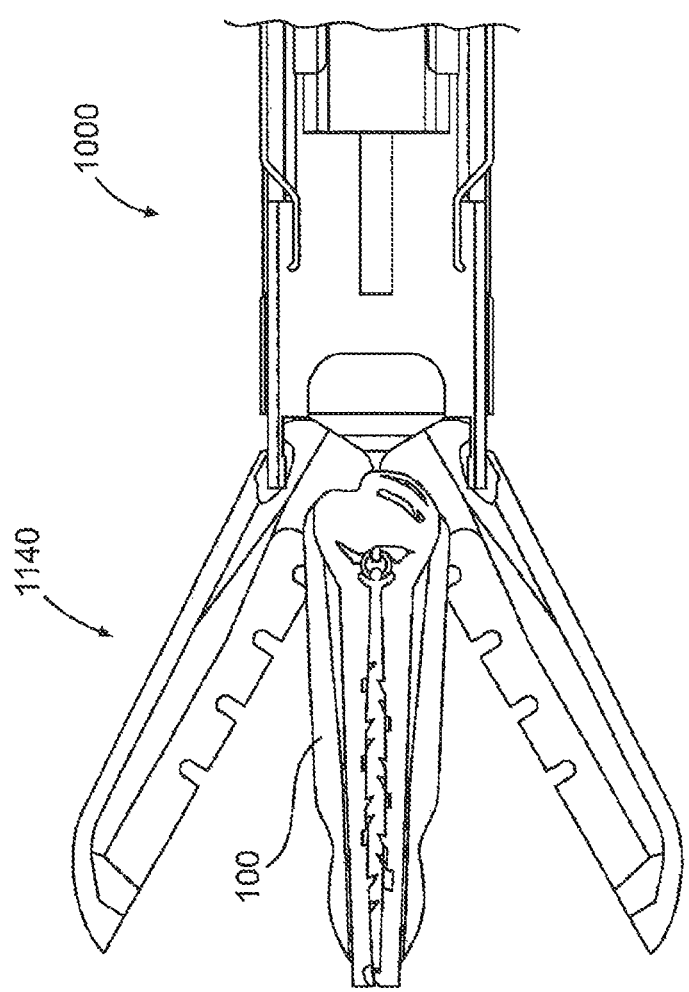
FIG. 54 shows a clip free/jaws open.

FIG. 54 illustrates the jaws 1140 on the applier 1000 opening exposing the clip 100. Removal of the applier 1000 to the right as shown in FIG. 54 will leave the clip 100 in place and it will be able to exit the applier 1000.

Figure 55:
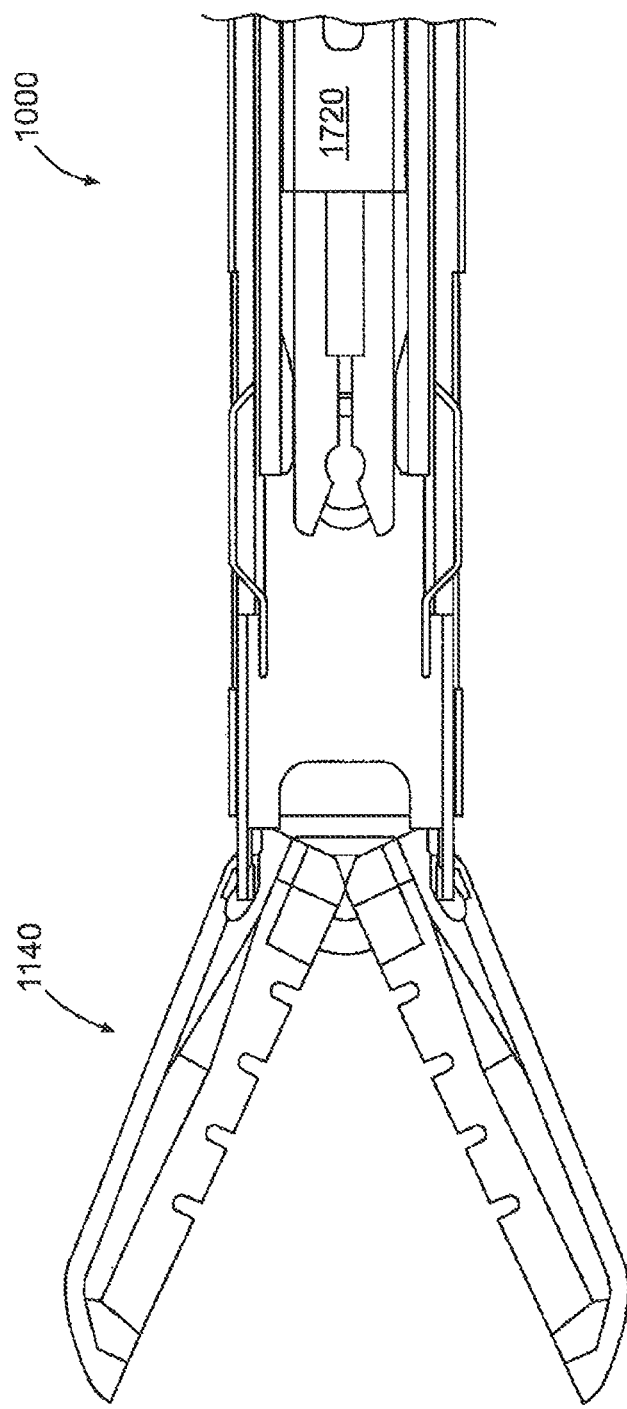
FIG. 55 shows a punch fully retracted.

FIG. 55 shows the jaws 1140 in an open position, the punch 1720 is fully retreated into the applier 1000.

Figure 56:
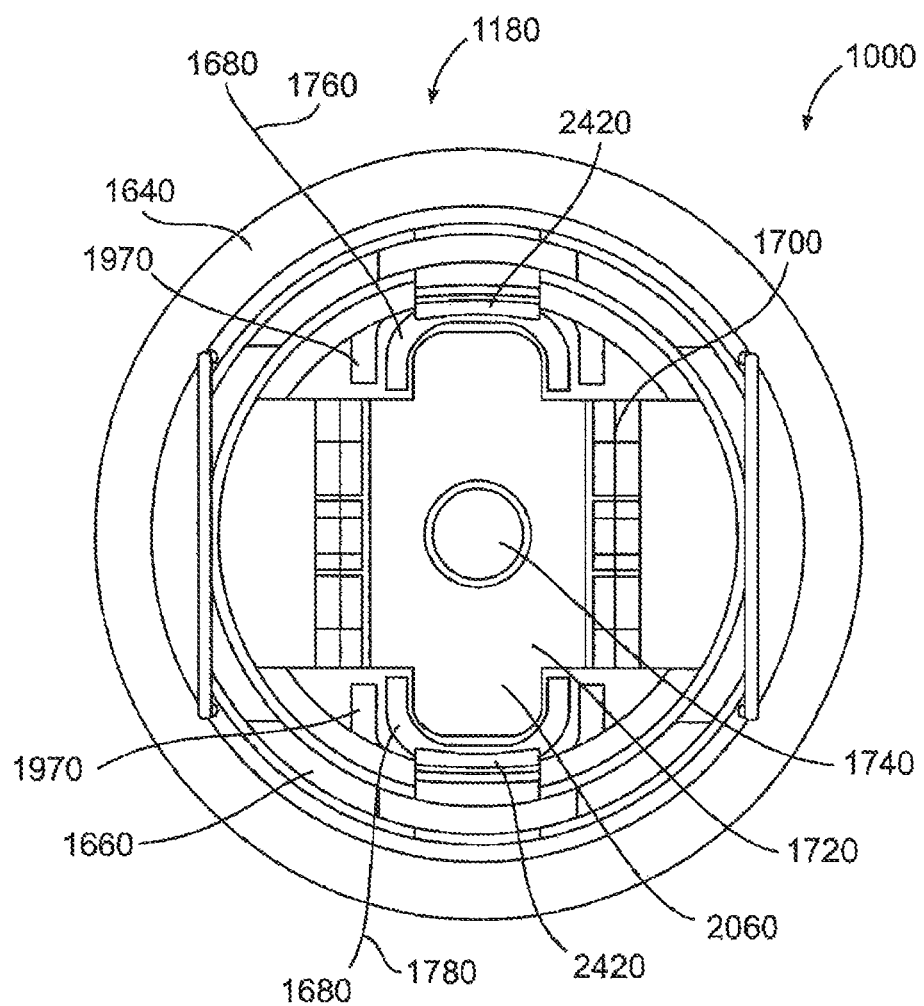
FIG. 56 shows an internal end view of an applier shaft.

FIG. 56 is a front view of the applier 1000 showing various portions of the applier 1000, for example the outer tube 1640 is shown. The catch 1700 is also shown as well as the spring legs 2420 of the outer tube 1640. The punch 1720 can also be seen. Projections 2060 are shown to be riding in the wedges 1760 and 1780. The wedge guides 1970 can also be shown as part of the wedges 1680. Inner tube 1660 is also illustrated.

FIG. 57 is an end-view of the applier 1000, the jaws 1600 and 1620 are open and the clip 100 is within the applier 1000. The top jaw 1600 and bottom jaw 1620 are in an open position. The outer tube 1640 is shown. The hinge pin 2620 of the jaws 1600 and 1620 are shown. The hinge pin 2620 connects the upper jaw 1600 and the lower jaw 1620 to the eye brackets 2340 on the outer tube 1640. The clip 100 as shown the upper leg 101 and the lower 102 in the spread part, open position.

Figure 58:
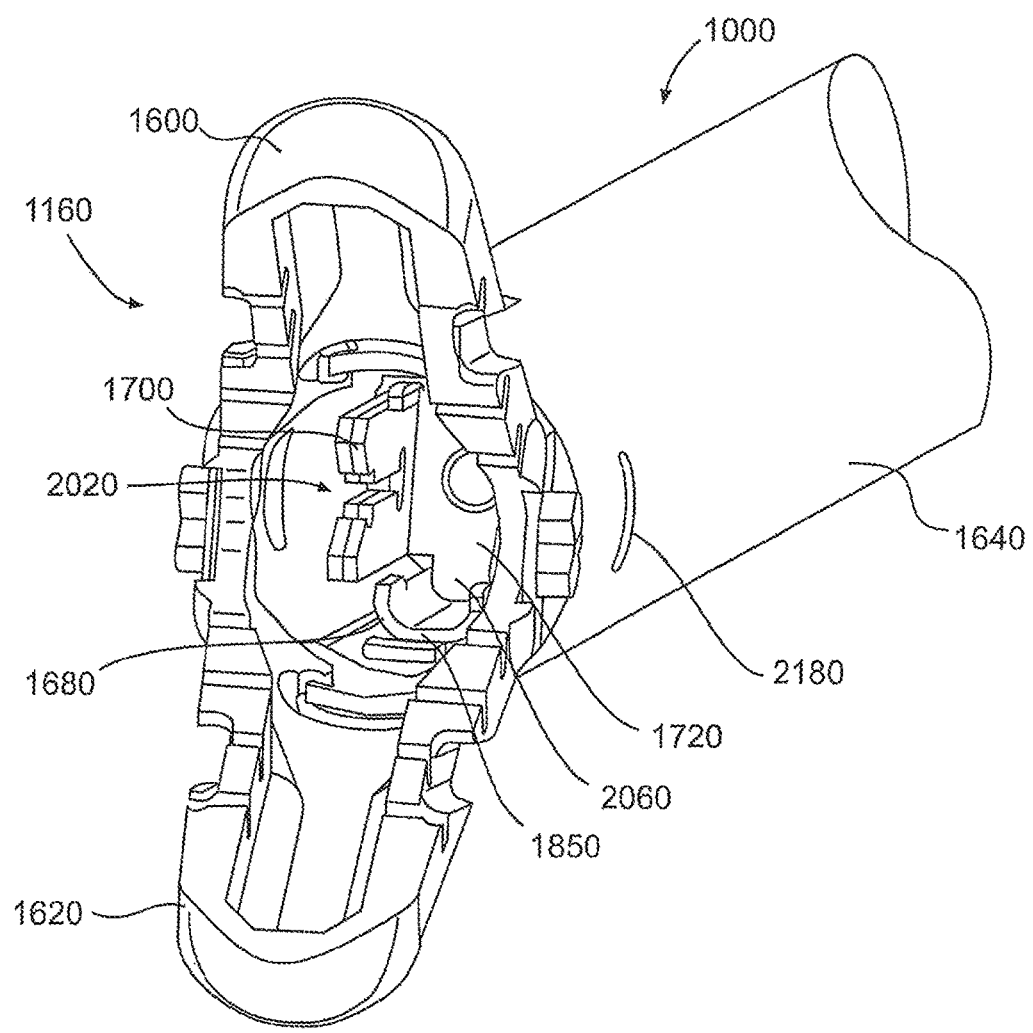
FIG. 58 shows a isometric view of distal end of applier.

FIG. 58 is an isometric view of the distal end 1160 of the applier 1000. The viewing port 2180 can be seen in the outer tube 1640. The viewing port 2180 allows the user to see if there is a clip 100 in the applier 1000 or whether, as shown in FIG. 58, there is no clip in the applier 1000. The punch 1720 can be seen along with the projections 2060 of the punch 1720, the projections are riding in the wedge 1680. The slot 2020 can be seen in the catch 1700.

FIG. 59 is similar to FIG. 58 with the exception that a clip 100 is shown within the applier 1000. The distal end 1180 of the applier 1000 is shown. The first leg 101 and the second leg 102 of the clip 100 in the open position. The jaws 1140 of the applier 1000 are also shown in the open position.

Figure 60:
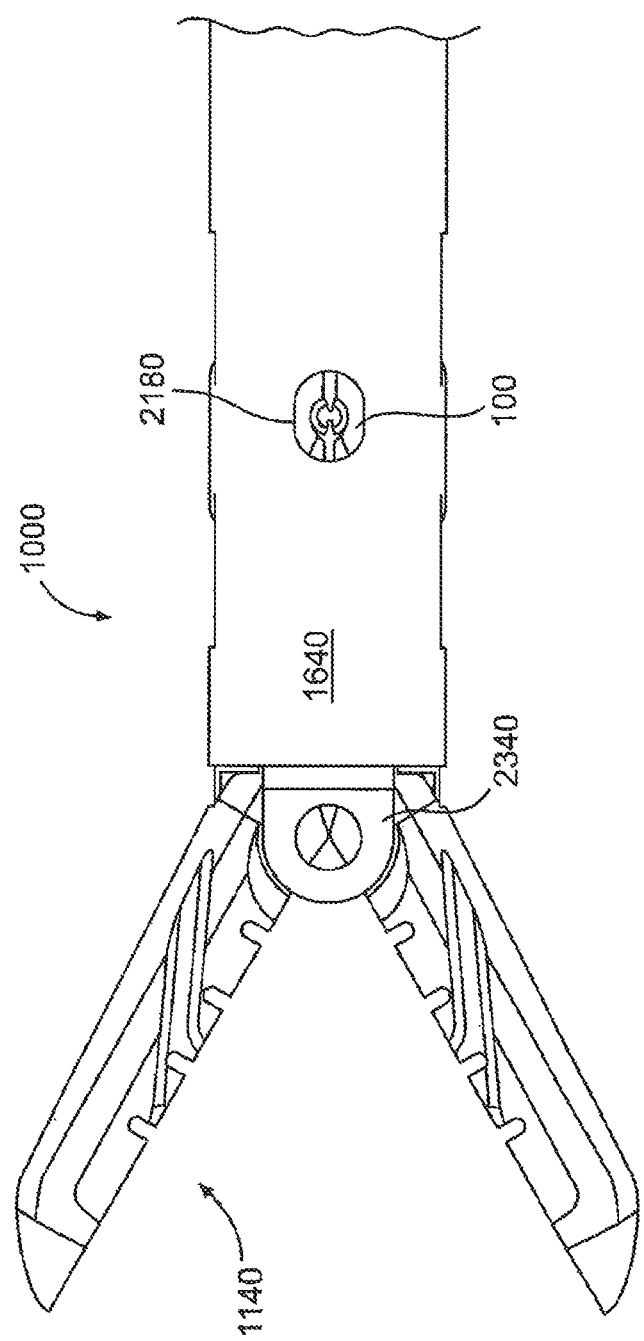
FIG. 60 shows a clip viewport.

FIG. 60 is a side-view of a portion of the applier 1000. The viewing port 2180 in the outer housing 1640 allows a user to see that a clip 100 is loaded into the applier 1000. The eye brackets 2340 of the outer tube 1640 are also seen, the jaws 1140 are in the open position.

Figure 61:
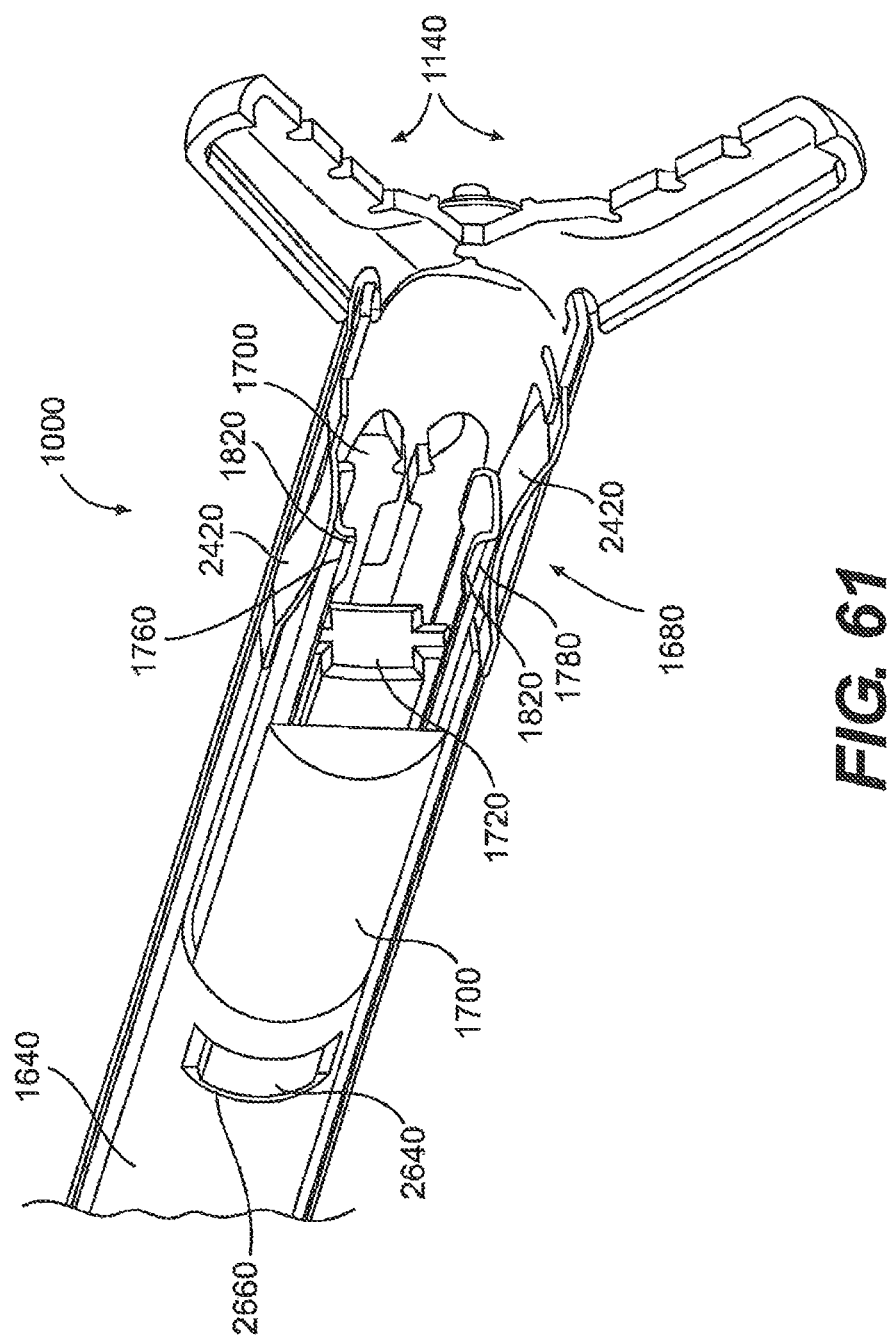
FIG. 61 shows a second embodiment of the applier.

FIG. 61 illustrates another embodiment of the applier 1000 where the wedges 1760 and 1780 and catch 1700 are visible in a cutaway. As shown in FIG. 61 applier 1000 has an outer tube 1640. The top wedge 1760 and bottom wedge 1780 are both located in the applier 1000. Spring legs 2420 are located on the outer tube 1640 and configured compress wedges 1760 and 1780 as the wedges 1760 and 1780 pass by. The spring legs 2420 push the wedges 1760 and 1780 inward towards each other. Catch 1700 is also shown. The thicker portion 1820 of the wedges 1760 and 1780 are also shown. The thicker portions 1820 will actuate part of the clip 100 (as shown in FIG. 61) as the wedges pass by the spring legs 2420. The punch 1720 can be seen as well as the catch 1700. A spring loaded tab 2640 connects the catch 1700 to the outer tube 1640.

FIG. 62 illustrates another view of the embodiment shown in FIG. 61 of the applier 1000. In this embodiment there is a catch wedge combination 2700. The catch 1700 is connected to the wedges 1680. The forked end 1960 of the catch 1700 can be shown as well as the slot 2020. The spring loaded button or tab 2640 is shown or tabbed and shown connecting the catch wedge combination 1700 to the outer tube 1640.

In FIG. 63 the outer tube 1640 has been removed to better show the catch wedge combination 2700. The upper wedge 1760 and lower wedge 1780 are shown and they are integrated with the catch 1700. The spring loaded tab 2640 is shown as well as the flex spring 2680 which connects the spring loaded tab 2640 to the catch wedge combination 2700.

Figure 64:
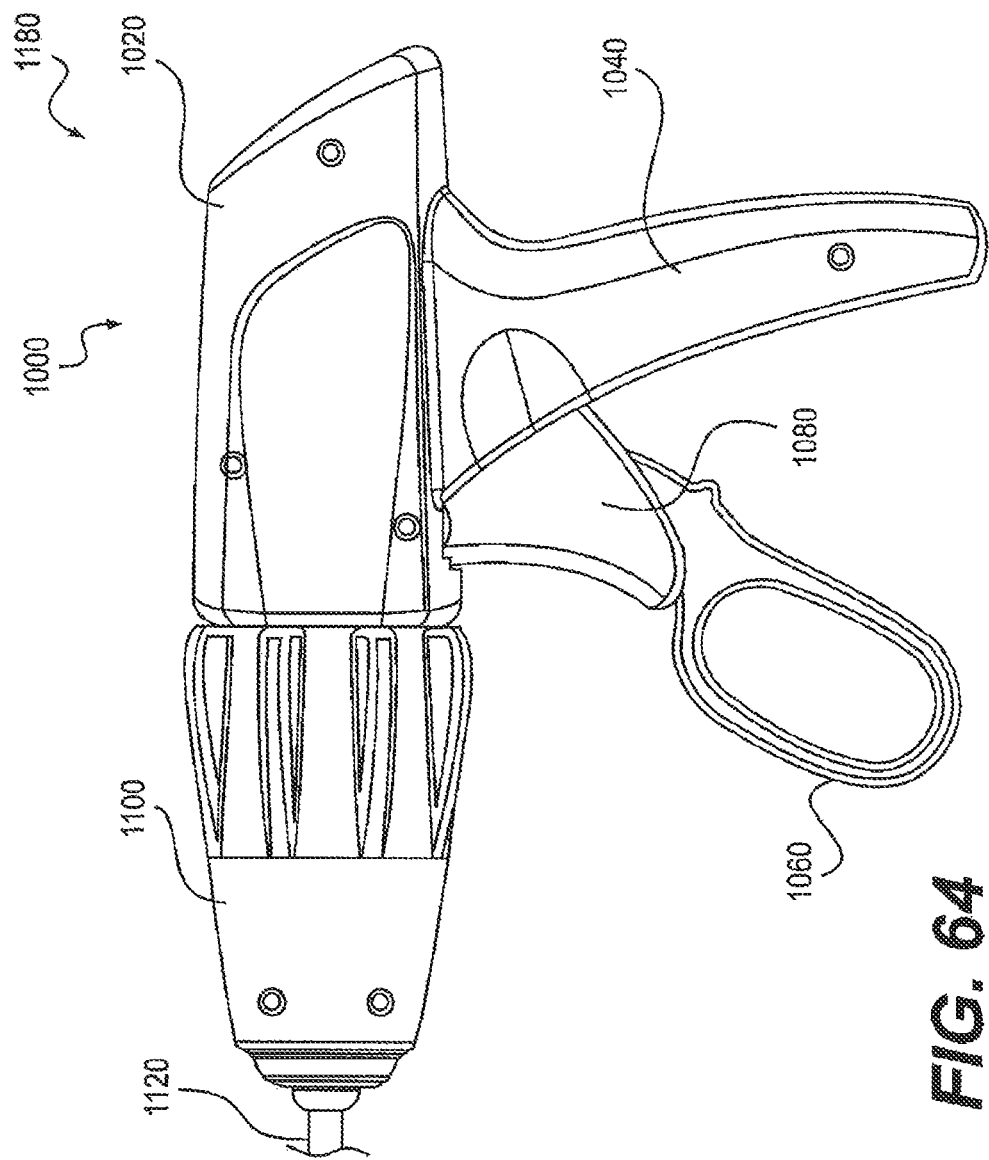
FIG. 64 shows an applier handle.

FIG. 64 is a side-view illustrating a proximal end 1180 of a portion of the applier 1000. The applier 1000 includes a housing 1020 which in some embodiments may be a clam shell type housing. A handle 1040 is also included along with a jaw actuating trigger 1060 and a ligate trigger 1080. A transmission housing 1100, houses a transmission to be discussed later and provides a transition between the housing 1020 and the shaft 1120.

FIG. 65 illustrates a portion of the applier 1000 as shown in FIG. 64, however, part of the housing 1020 is removed in order to illustrate interior components.

FIG. 66 is an exploded view of the interior components.

FIG. 67 is similar to FIG. 65 in that the housing 1020 has been removed.

Figure 68:
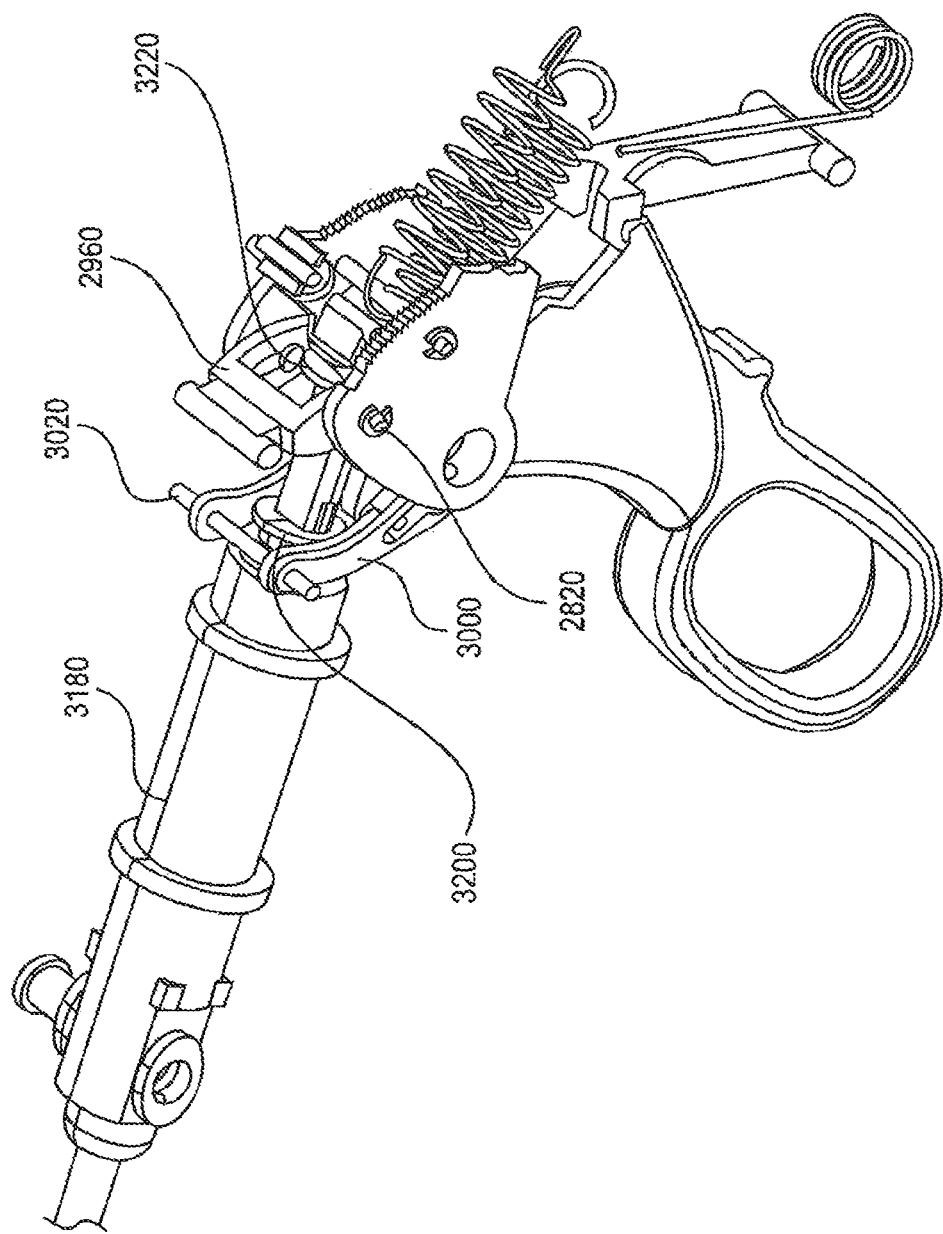
FIG. 68 shows internal handle components.

FIG. 68 illustrates interior components where the housing 1020 is removed.

The following description will apply to FIGS. 65-68, however, not all of the reference numerals may be called out in all the figures nor will they be necessary be all visible in FIGS. 65-68. Both the jaw triggers 1060 and the ligate trigger 1080 pivot about the trigger pivot shaft 2940. The user may pull either ligate trigger 1080 or the jaw trigger 1160 toward the handle 1040. Both of these triggers are spring loaded. There is a ligate lever spring 2760 and a grasper lever spring 2770 which bias the triggers 1080 and 1060 to an outward position. However, the triggers do not always remain in an outward position, even when a user has let go of the triggers 1080 and 1060 due to the ratchet plates 2800. The ratchet plates 2800 are similar but have slightly different ratcheting systems that will be described herein. Ratchet plates 2800 contain ratchet teeth 2860. The ratchet plates 2800 are connected to a spring bias first pawl 2880 and second pawl 2890. The first pawl 2880 and the second pawl 2890 are connected by a pawl pivot pin 2900. The first and second pawls 2880 and 2890 are spring loaded by a pawl spring 2910 which urges against a pawl spring anchor 2930 which is attached to the back of the housing 2720. The first pawl 2880 engages the ratchet teeth 2860 until a pawl lift projection 2920 lifts either the first pawl 2880 or the second pawl 2890. When the first pawl was disengaged by the pawl lift projection 2920 then the second pawl 2890 is engaged with the ratchet teeth 2860. If it is the second pawl 2890 that is disengaged with the ratchet teeth 2860 by the pawl lift projection 2920, than the first pawl 2880 becomes engaged with the ratchet teeth 2860. In this manner, the first pawl 2880 prevents undesired trigger movement in one direction and the second pawl 2890 prevents undesired trigger movement in the second direction.

Ratchet plates 2800 are connected to the ligate lever pivot shaft 2980 via pivot pins 2820. The pivot pins 2820 have locking clamps 2840 to prevent the pivot pins 2820 from disengaging or coming off the ratchet plates 2800. Though ligate lever pivot shaft 2980 includes a ligate lever slot 3140 and allows the pivot pins 2820 to slide through ligate lever slot 3140, the dimensions of the ligate lever slot 3140 may be selected to achieve desired inputs into the transmission which will be described in further detail below. The ligate trigger 2800 also has a trigger interlock projection 3120 just configured to interacting lock with the trigger lock 3080. The trigger lock 3080 is biased by a spring 2780 to a forward position. The trigger lock 3080 includes a trigger interlock hook 3100 which interacts with the trigger interlock projection 3100 to lock the ligate trigger 1080 with a ligate trigger 1080 is at a specific position. The specific dimensions of the ligate trigger interlock projection 3120 and the trigger interlock may be selected in order to provide a desired input into transmission 3180 one of ordinary skill in the art. A jaw trigger 1060 is connected to a grasper lever 3000. The grasper lever 3000 includes a grasper lever pivot shaft 3020 and a curve slot 3040. A curved slot pin 3060 may travel through the curved slot 3040 and is acted upon by spring extension 3160 which is controlled by the grasper lever spring 2770. Actuation of the jaw trigger 1060 will cause the grasper lever 3000 and the grasper lever pivot shaft 3020 to act upon the transmission 3180 to provide input to the transmission 3180 which will be discussed further detail below.

In some the components described and as shown in FIGS. 65-68 are designed to provide inputs into the transmission 3180. Various connecting mechanisms may be used to connect various inputs such as the ligate trigger 1080 and the jaw trigger 1060 provide inputs to a transmission 3180 to actuate the applier 1000 in a manner desired by a user. The ligate lever spring 2760 and grasper lever spring 2770 may be anchored to the housing by the spring anchors 2740. The size and dimension of the curve slot 3040 can be selected by one of ordinary skill in the art in order to provide the desired input into the transmission 3180 at a desired trigger 1060 position.

As shown specifically in FIG. 68, a grasper lever pivot shaft 3020 engages the jaw actuator link 3200 of the transmission 3180. The center actuator link 3220 engages the ligate lever 2960 via the pivot pins 2820. In some embodiments of the invention, the pawls 2880 and 2890 and the ratchet teeth 2860 along with the pawl lift projection 2920 are configured so that once the ligate trigger 1080 starts to move in a direction, it cannot reverse course until it is completed movement in that direction and, at that point, it may reverse course. In other words, once the user starts to pull that trigger 1060, 1080, the trigger 1060, 1080 may not move forward until the trigger 1060, 1080 has first become all the way back. Once the trigger 1060, 1080 has come all the way back, then it may move forward, but once a trigger 1060, 1080 starts a forward position it cannot move back until it first moves all the way forward.

Figure 69:
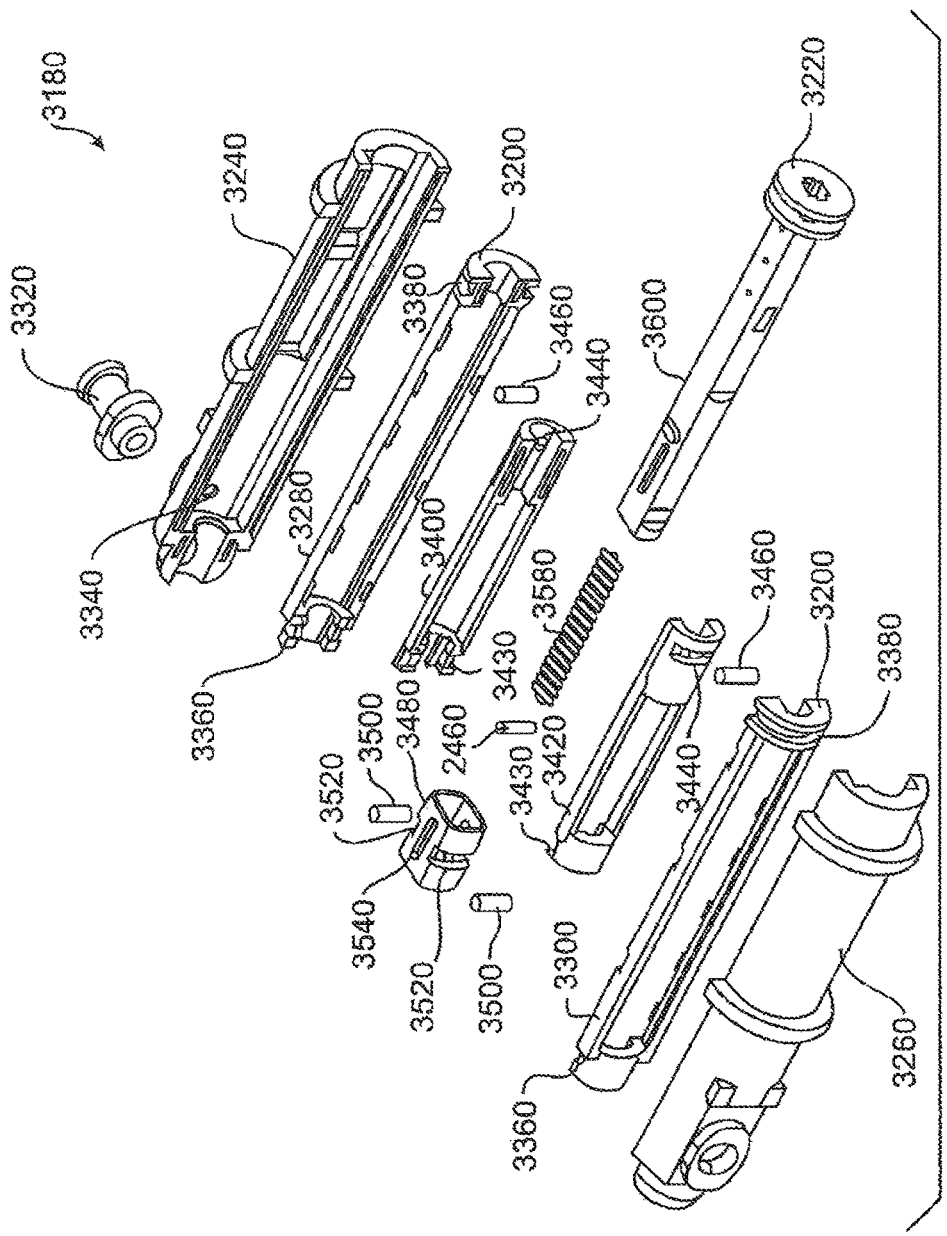
FIG. 69 shows multistage transmission components.

FIG. 69 is an exploded view of the transmission 3180 according to an embodiment of the invention. The transmission 3180 includes an outer clam shell housing 3240 and 3260. The Leur port 3320 connects to a hole 3340 in the clam shell housing 3240. The Leur port 3320 is used to connect the transmission 3180 to a cleaning fluid for flushing and cleaning not only the transmission 3180 but the entire applier 1000 between uses. Cleaning of surgical tools as well known in the art and will not be described further here. Inside the outer clam shells 3240 and 3260 are jaw actuator links 3280 and 3300, they are also in a clam shell configuration. The jaw actuator links 3300 and 3280 include attaching structure 3360 at the front for attaching to various components which will be described later. The jaw actuator links 3300 and 3280 also define a jaw actuator input 3200. The jaw actuator input 3200 defines an engaging groove 3380 which allows the jaw actuator input 3200 to attach to pin 3020 as shown in FIG. 68. In the jaw actuating links 3280 and 3300, between the jaw actuator links 3280 and 3300 and the catch pusher latches 3400 and 3420 are connecting pins 3460. Connecting pins 3460 reside in slots 3440 in the catch pusher latches 3400 and 3420. The catch pusher latches 3400 and 3420 also include attaching structure 3430 for attaching components which will be described later below. The catch pusher latches 3400 and 3420 contain the center spindle 3600. The center spindle 3600 is attached to the center actuator link 3220. Center actuator link 3220 is connected to pivot pins 2820 (shown in FIG. 66) which allows the center actuator link 3220 to be actuated by a user. The center spindle 3600 also houses and is attached to punch return spring 3580. A punch latch interlock 3480 attaches to the center spindle 3600 and provides slots 3520 for pins 3500 to reside. The punch latch interlock 3480 also defines a pin slot 3540 for pin 2460. The purpose for these pins and slots will be described in more detail later blow.

FIG. 70 is a perspective view of transmission 3180. The outer clam shell housing 3240 and 3260 are shown as well as the Leur port 3320. The jaw actuator input 3200, the center spindle 3600 and the center actuator link 3220 are also shown.

In FIG. 71 the outer clam shell housing 3240 and 3260 have been removed in order to better show the interior components. The jaw actuator links 3280 and 3300 are shown as well as the catch punch latches 3420, the pin grooves 3520 and punch latch interlock pins 3500 are set therein. The slot 3440 is also shown with the connecting pin 3460 shown therein. The jaw actuator link 3200, the center spindle 3600 and the center actuator link 3220 are also shown.

In FIG. 72, the jaw actuator link is removed to better show various aspects of the transmission 3180. Other features are also shown in showing connections to the transmission. For example, the outer tubes 1640 is shown with the rim 2380. The brackets 2160 on the proximate end of the inner tube 1660 are also shown as well as the catch 1700 connected to the transmission 3180. The catch puncher latches 3400 and 3420 are also shown as well as the center actuator link 3220.

In FIG. 73, the catch pusher latches are removed. The outer tube 1640 is shown as well as the inner tube 1660 and the attaching brackets 2160 are attached to the inner tube 1660. The catch 1700 is shown having its attaching brackets 1950 also shown. The punch latch interlock 3480 is shown as well as the punch latch interlock pins 3500. The pin slot 3540 and the connecting pin 3460 residing in the pin slot 3540. The punch latch interlock 3480 is attached to and carried on the center spindle 3600.

Figure 74:
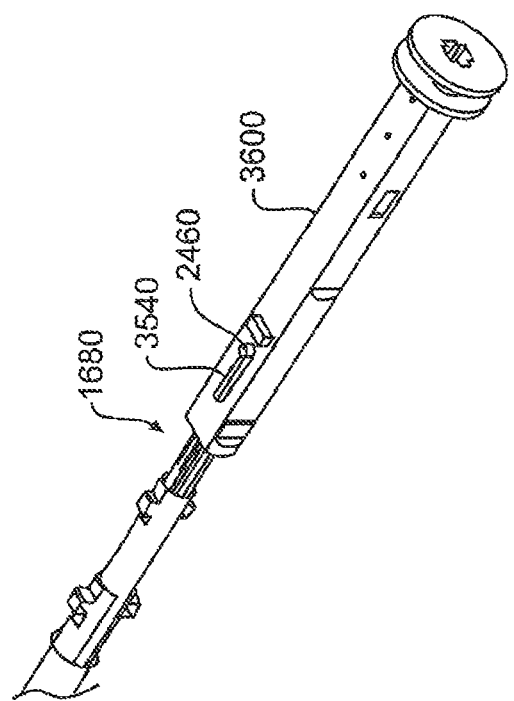
FIG. 74 shows a transmission with the punch latch interlock and dowel removed.

In FIG. 74, the punch latch interlock and pins are removed thus showing the center spindle 3600, the pin 2460 residing in a pin slot 3540. The wedges 1680 can also be seen in part.

Figure 75:
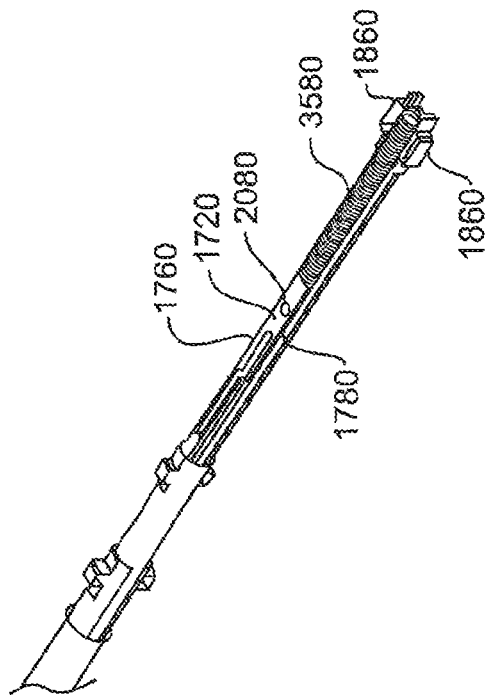
FIG. 75 shows a transmission with the center spindle and dowel removed.

In FIG. 75, the center spindle 3600 has been removed. The top 1760 and bottom 1780 wedges are shown and the punch 1720 is shown in between the top 1760 and bottom wedge 1780. The hole 2080 in the punch 1720 is the same hole 2080 in which the pin 2460 shown in FIG. 74 resides. The punch return spring 3580 is also shown urging against the punch 1720 and fit between the wedges 1760 and 1780. Connecting brackets 1860 on the wedges 1760 and 1780 are also shown. Connecting brackets 1860 connect the wedges 1760 and 1780 to the center spindle 3600 found in FIG. 74.

Figure 76:
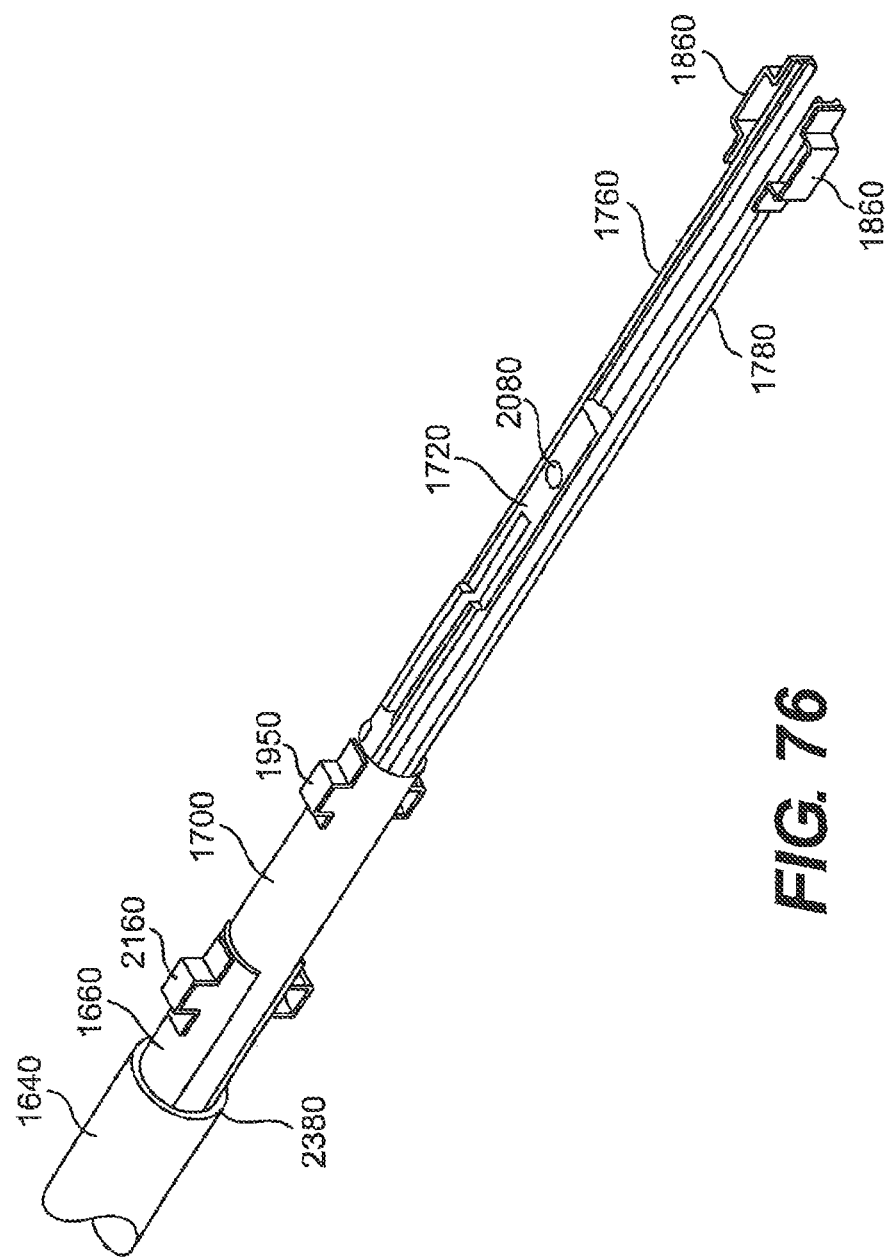
FIG. 76 shows a transmission with the punch return spring removed (distal shaft connection points shown).

FIG. 76 is similar to FIG. 75 but it shows the punch return spring 3580 removed. The outer tube 1640 is shown along with the rim 2380. The inner tube 1660 is shown with the brackets 2160 on the approximate end of the inner tube 1660. The catch 1700 is shown along with the attaching bracket 1950. The punch 1720 is also shown riding along in between the top wedge 1760 and bottom wedge 1780. The hole 2080 and the punch 1720 is also shown. The connecting bracket 1860 on the wedges 1760 and 1780 are also shown. The transmission is, for the most part, absent from the drawing shown in FIG. 76, but rather the only components left are those the transmission connects to and provides movement to.

Figure 77:
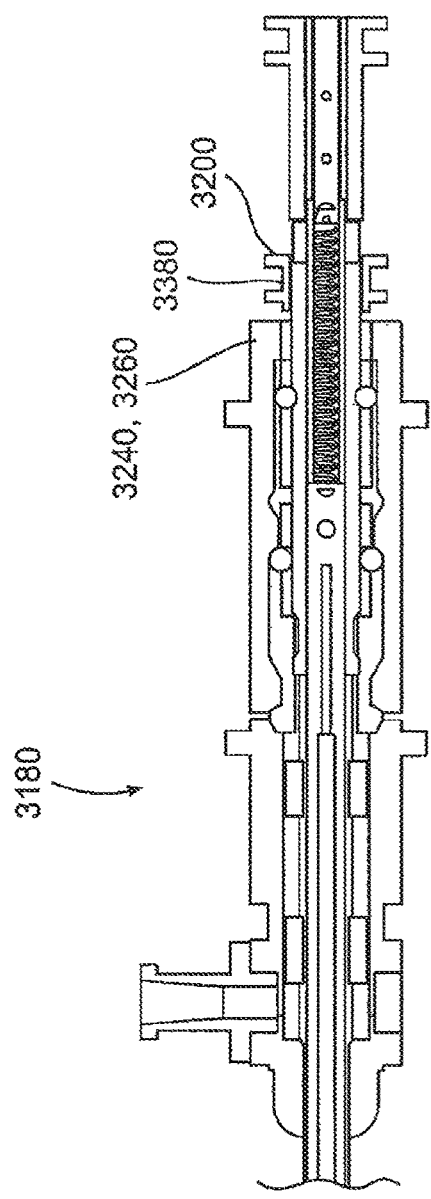
FIG. 77 shows a cross-section of the transmission where the jaws are open (clip loaded)

FIG. 77 is a cross-sectional view of the transmission 3180 and various elements that the transmission connects to. In FIG. 77, the outer clam shell housing 3240 and 3260 are shown as well as the jaw actuator link clam shell 3380 and the jaw actuator input 3200. The jaw actuator link or input 3200 is not contacting the outer clam shell housing 3240 and 3260. The actuator link or input 3380 is in a position to allow the jaws (not shown in FIG. 77) being open in order to load a clip 100 (not shown) into the applier 1000.

Figure 78:
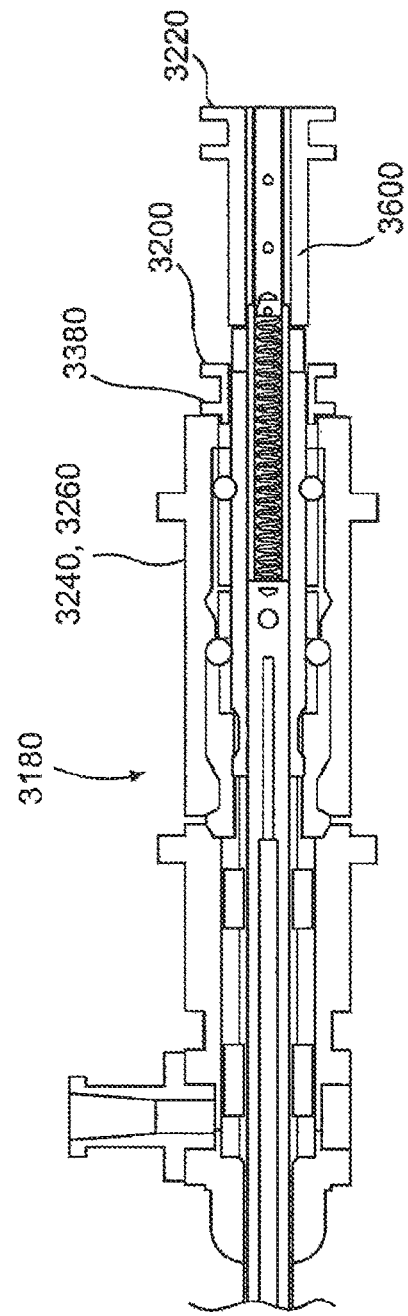
FIG. 78 shows a cross-section of the transmission where the jaws are closed (clip loaded).

FIG. 78 is a cross-sectional view of the transmission 3180 where the jaws 1140 (not shown in FIG. 77) are closed. The jaw actuator link or input 3200 has moved forward and is contacting the outer clam shell housing 3240 and 3260. Note that the center actuator link 3220 riding on the center spindle 3600 is about the same distance from the jaw link or input 3380 as shown in FIG. 77. Thus the center actuator link 3220 moved forward about the same distance as the jaw actuator link or input 3380 when it moved up against the outer clam shell housing 3240 and 3260.

Figure 79:
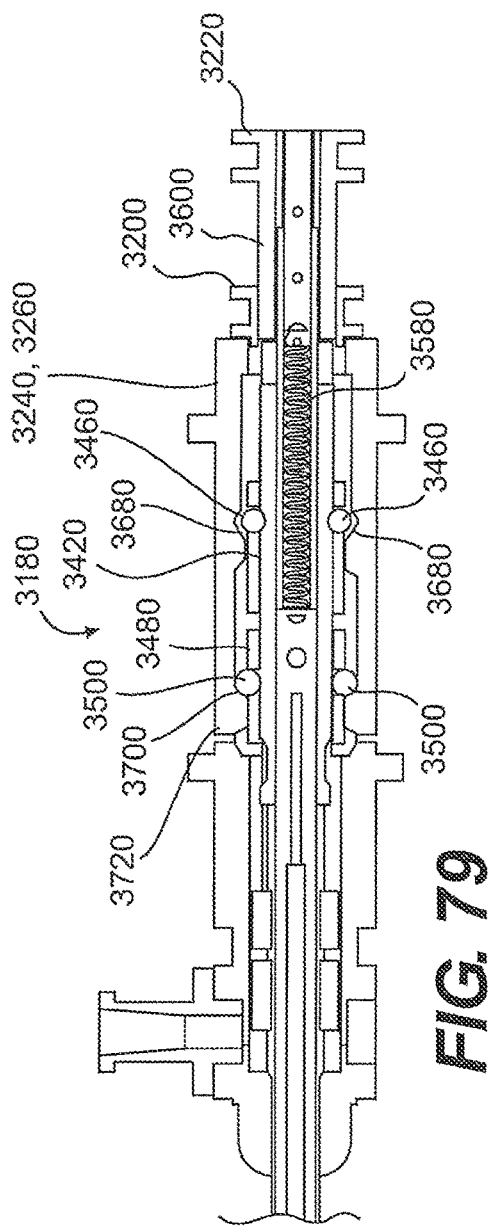
FIG. 79 shows a cross-section of the transmission where the clip is advanced.

FIG. 79 is a cross-sectional view of a transmission 3180 where the center spindle 3600 has advanced. The jaw actuator link or input 3200 is still pressed against the outer clams shell housing 3240 and 3260. The connecting pin 3460 resides within the pocket 3680 in the outer shell 3240 and 3260. Further, punch latch interlock pins 3500 have cam surfaces 3700 and will urge against the fingers 3720 on the outer shell 3240 and 3260. As the center spindle 3600 advances, the catch pusher latch 3420 and the punch latch interlock 3480 move forward. Tension begins to build in the punch return spring 3580. The pins 3460 and 3500 are pins that act as connection points to allow everything to advance together and thus the clip 100 (not shown in FIG. 79) is advanced.

Figure 80:
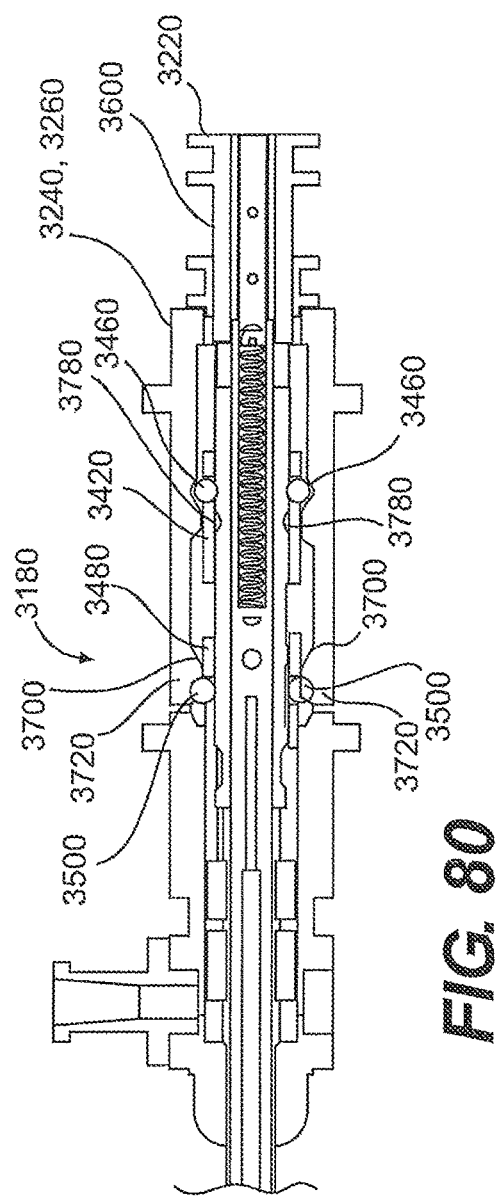
FIG. 80 shows a cross-section of the transmission where the clip is closed.

Turning now to FIG. 80 the transmission 3180 is shown where the clip 100 (not shown in FIG. 80) is closed. The center spindle 3600 continues to advance by actuation of the center, actuator link 3220. The catch pusher latch 3420 disengages as the pins 3460 come out of the pocket 3780 of the outer shell 3240 and 3260. Thus, the catch pusher latch 3420 stops. The punch latch interlock 3480 moves forward and the cam surface 3700 causes the FIG. 3720 of the outer shell 3240 and 3260 to move aside and allow a punch latch interlock 3480 to move forward. While the fingers 3720 in the outer shell 3240 and 3260 are not shown in a more spread apart position in FIG. 80, they should be as they have moved regularly outward slightly by way of the caming surface 3700 acting upon the fingers 3720.

FIG. 81 illustrates a position of the transmission 3180 where the clip 100 (not shown) is latched. The center spindle 3600 is fully advanced by means of the center actuator link 3220 being pressed forward into the transmission 3180. The punch latch interlock 3480 moves forward and the punch latch interlock pins 3500 moves forward and drop into pockets 3740 behind the outer shell fingers 3720.

FIG. 82 illustrates the transmission 3180 when the wedges 1680 return. The center spindle 3600 moves outward by the input placed on the center link 3220. The jaw actuator link or input 3200 remains in a position but up against the outer clam shell housing 3240 and 3260. The punch latch interlock 3480 stays in position. The catch pusher latch 3420 began to return allowing the connecting pins 3460 to return to the pin connecting groove 3780.

FIG. 83 illustrates the transmission 3180. The center spindle 3600 continues to return via an input on the center actuator link 3220. A jaw actuator or link 3200 is still butted against the outer clam shell housing 3240 and 3260. The punch latch interlock 3480 continues to pull back and the catch pusher latch 3420 continues to return. The punch latch interlock pins 3500 cause the fingers 3720 on the outer shell 3240 and 3260 to spread apart. The connecting pins 3460 are no longer in the pocket 3680 of the outer shell 3240 or 3260.

FIG. 84 shows the position of the transmission 3180 where the punch 1720 is unlatched. The center spindle 3600 continues to return to an extended position. The punch latch interlock 3480 continues to pull back. The catch pusher latch 3400 continues to return. The pins 3500 force the fingers 3720 apart.

Figure 85:
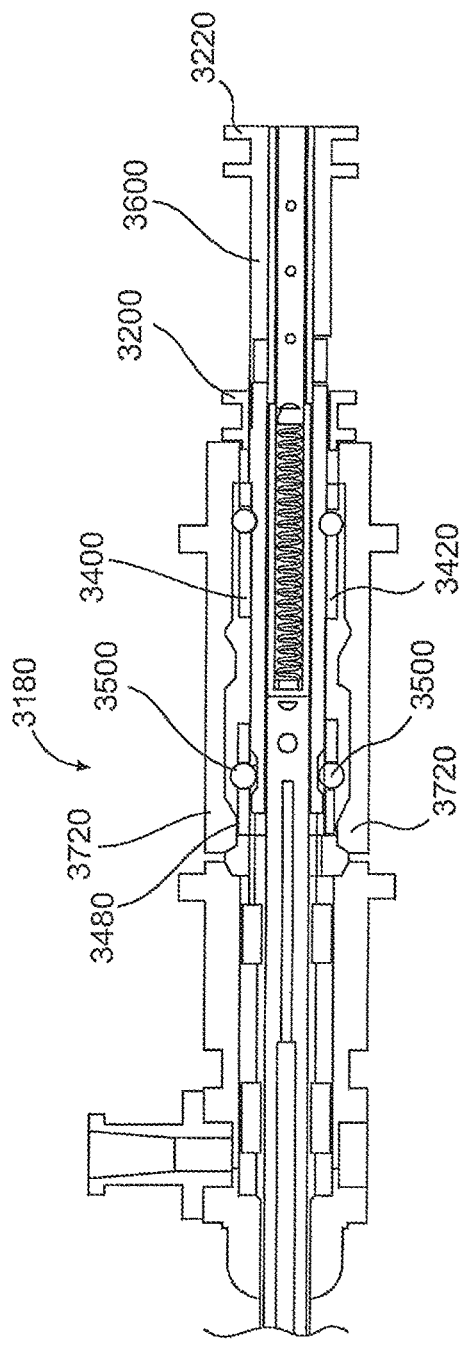
FIG. 85 shows a cross-section of the transmission where the clip is free from the device.

FIG. 85 illustrates a transmission 3180 in a position to free the clip 100 (not shown). The center spindle 3600 reaches a fully extended end position by input placed on the center spindle 3220. A punch latch interlock 3480 continues to pull back. The catch pusher latch 3400 reaches an end position. The punch latch interlock pins 3500 are passed the fingers 3720 and the outer shell 3240 and 3260 and the punch latch interlock 3480 is therefore free to return.

Figure 86:
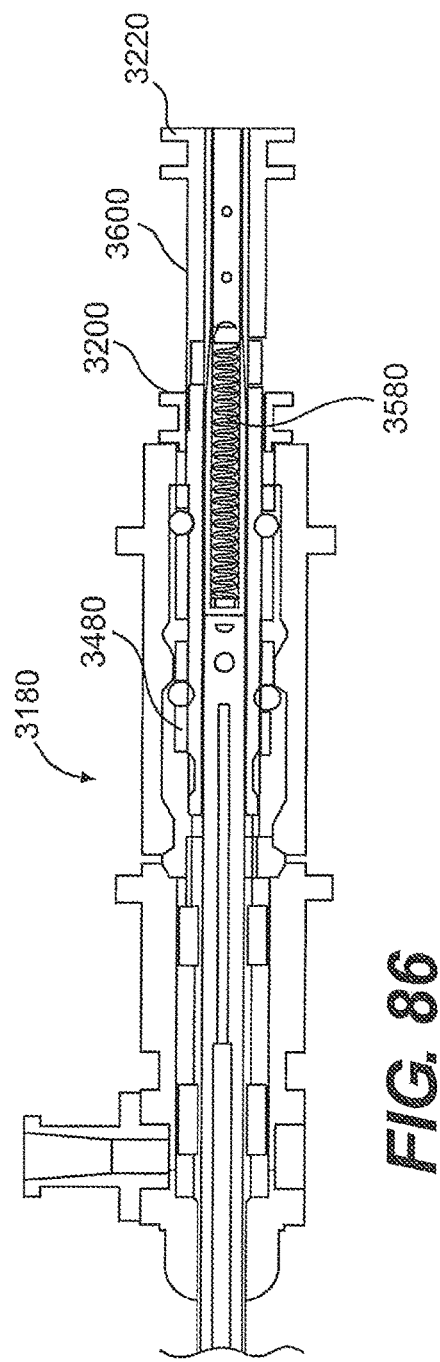
FIG. 86 shows a cross-section of the transmission where the punch spring has returned.

FIG. 86 illustrates the transmission 3180 in a position for the punch return spring 3580 to be relieved. A center spindle 3600 is at the end position. The punch latch interlock 3480 pulls back to an end position under force from the extension spring of punch return spring 3580.

Figure 87:
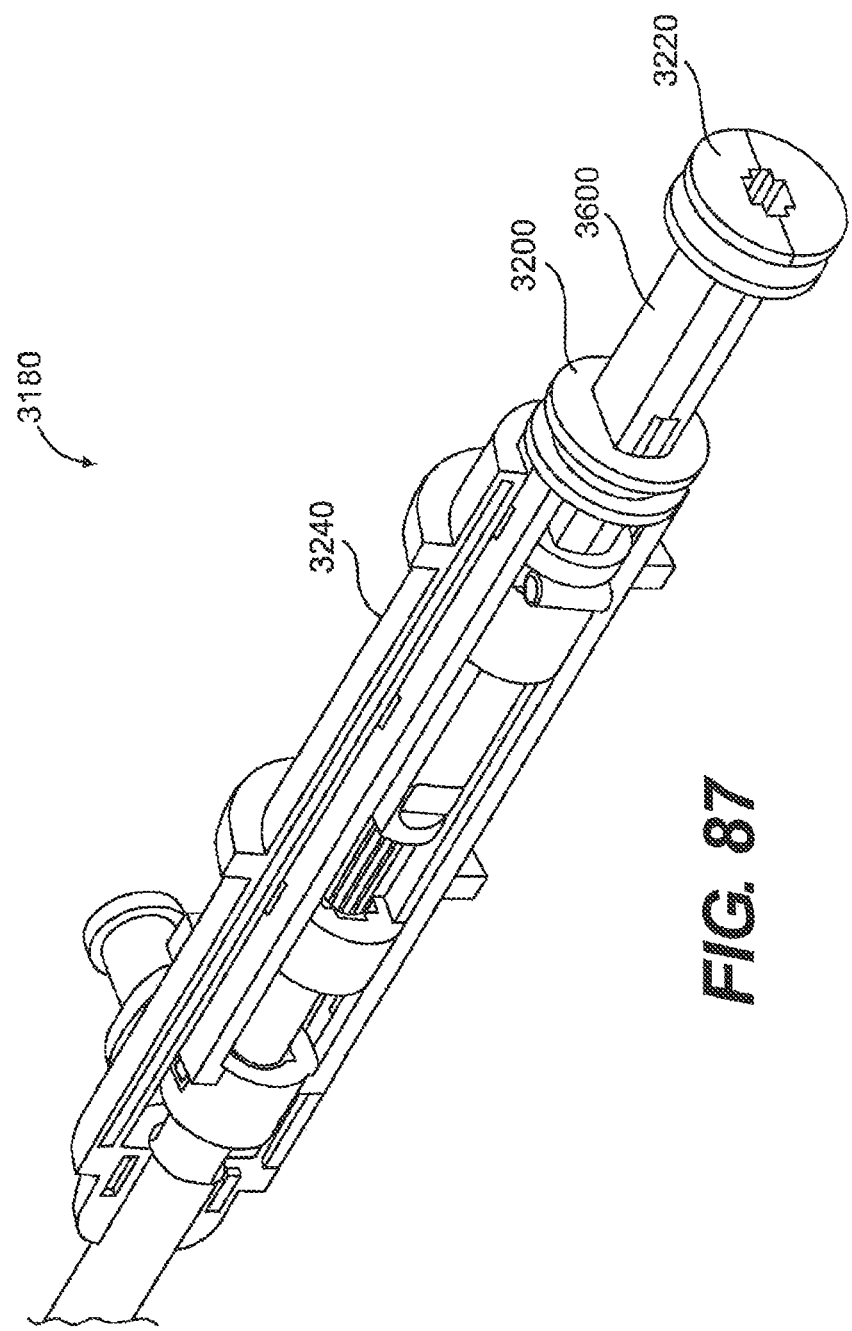
FIG. 87 shows an isometric view of a transmission in an embodiment that does not have a punch latch interlock.

FIG. 87 illustrates a second embodiment of the transmission 3180 wherein the second embodiment there is no punch latch interlock. As shown in FIG. 87, part of the clam shell housing 3260 is removed to expose interior elements. The outer clam shell housing 3240 is shown along with various elements such as but not limited to a jaw actuator input link 3200, the center spindle 3600 and the center actuator link 3220.

Figure 88:
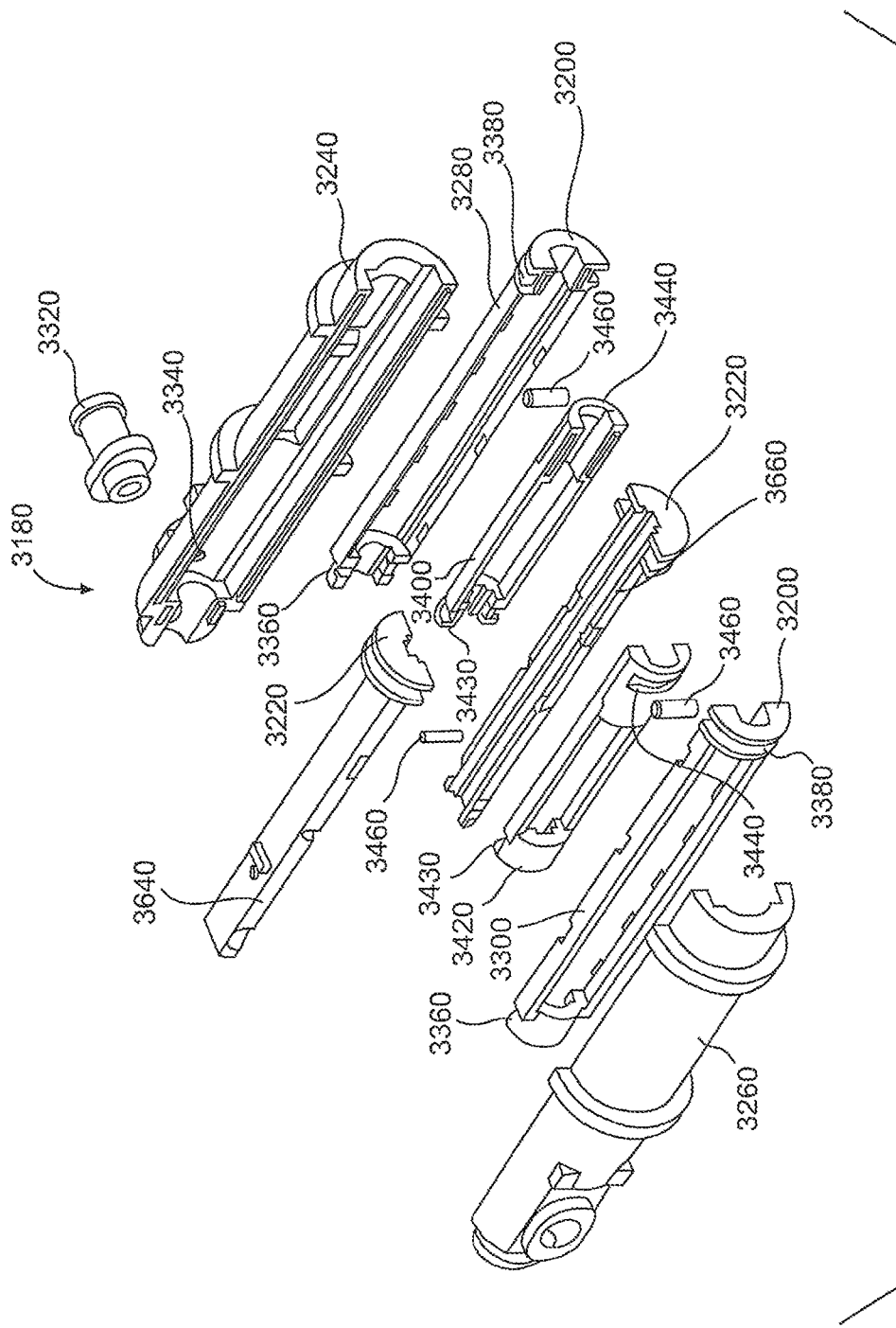
FIG. 88 shows an exploded isometric view of another embodiment showing multistage transmission components.

FIG. 88 is an exploded view of a transmission 3180 in accordance within a second embodiment. FIG. 88 shows outer clam shell housing 3260 and 3240. The outer clam shell housing 3240 has a hole 3340 for connecting to a Leur port 3320 which is used to connect a cleaning device with cleaning solution to clean a transmission and a 3180 and the rest of the tool. Cleaning of surgical tools will not be discussed in detail here.

Inside the outer clam shell housing 3260 and 3240 are jaw actuator links 3280 and 3300. The jaw actuator links 3280 and 3300 include attaching structure 3360 at one end and jaw actuator input link 3200 at another end. The jaw actuator input or link 3200 includes an engaging groove 3380. Between the jaw actuator links 3280 and 3300 resides a connecting pin 3460 for connecting the jaw actuator links 3280 and 3300 with catch puncher latches 3400 and 3420. The catch puncher latches 3400 and 3420 include attaching structure 3430 at one end. The catch puncher latches 3400 and 3420 also include slots 3440 for the pin 3460. The catch puncher latches 3420 and 3400 house the center spindles 3640 and 3660. The center spindles 3640 and 3660 may be in a clam shell configuration as shown and may entrap a pin 3460.

Figure 89:
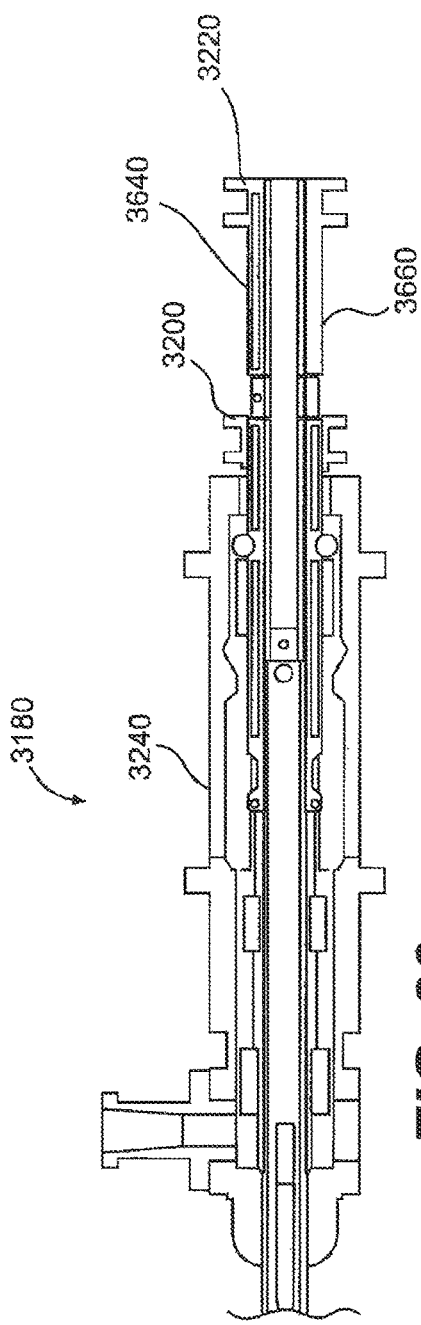
FIG. 89 shows a cross-section of the transmission where the jaws are open (clip loaded).

FIG. 89 is a side cross-sectional view of the transmission 3180 according to the second embodiment. The jaw actuator link or input 3200 is shown spaced away from the outer clam shell 3240. The center spindle clam shell 3640 and 3660 as shown as well as the center actuator link 3220. The jaws 1140 are open when the transmission 3180 is in the position as shown in FIG. 89. The clip 100 (not shown) may be loaded when the jaws 1140 are open in the transmission 3180 is in the position shown in FIG. 89.

Figure 90:
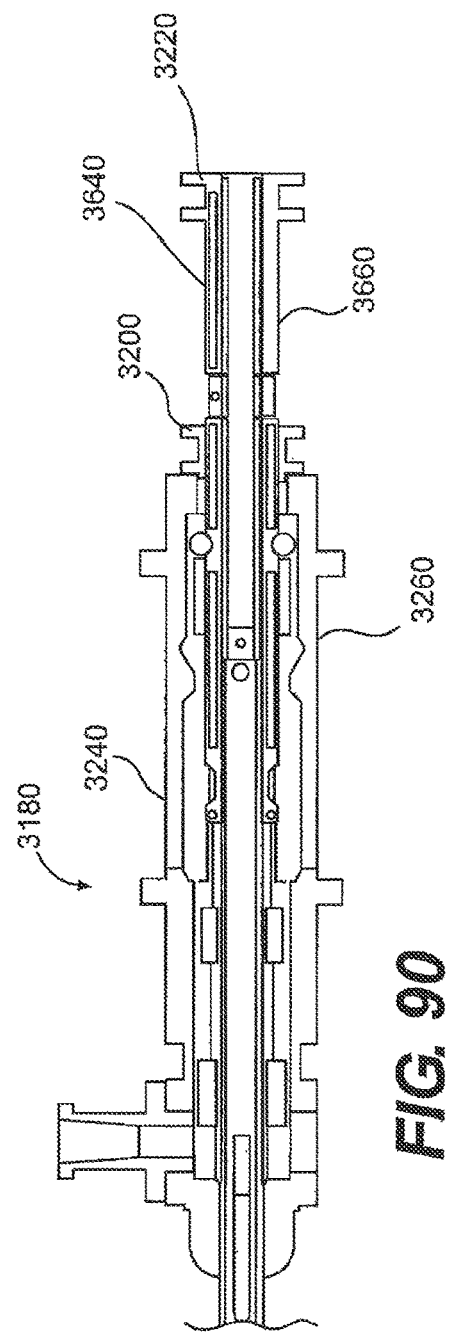
FIG. 90 shows a cross-section of the transmission where the jaws are closed (clip loaded).

FIG. 90 shows a transmission 3180 in an position where the jaws 1140 are closed and the clip 100 may be loaded inside the jaws 1140. The jaw actuator link 3200 is pressed against the clam shell housing 3240 and 3260. The center spindle clam shell 3640 and 3660 are shown and carry the center actuator link 3220. Center actuator link 3220 and the jaw actuator link or input 3200 are located about the same distance from each other in FIG. 90 as they are shown in FIG. 89.

Figure 91:
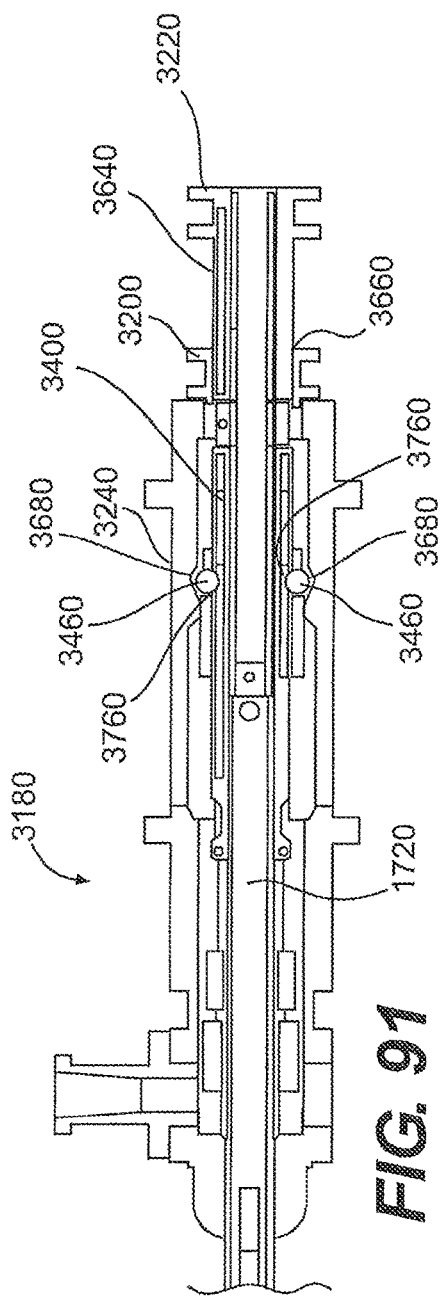
FIG. 91 shows a cross-section of the transmission where the clip is advanced (wedges and catch move together).

FIG. 91 shows a side view of the transmission 3180 where the clip 100 advances into the jaws 1140. The wedges 1680 and catch 1700 (not shown in FIG. 91) can move together. The center spindle 3640 and 3660 began to advance by an input placed on the center actuator link 3220. The jaw actuator link or input 3200 remains in position. Connecting pins 3460 are in the pocket 3680 in the outer shell 3240 and 3260. The locking pin grooves 3760 moved away from the connecting pin 3460. The punch 1720 and catch puncher latch 3420 and 3400 work together.

Figure 92:
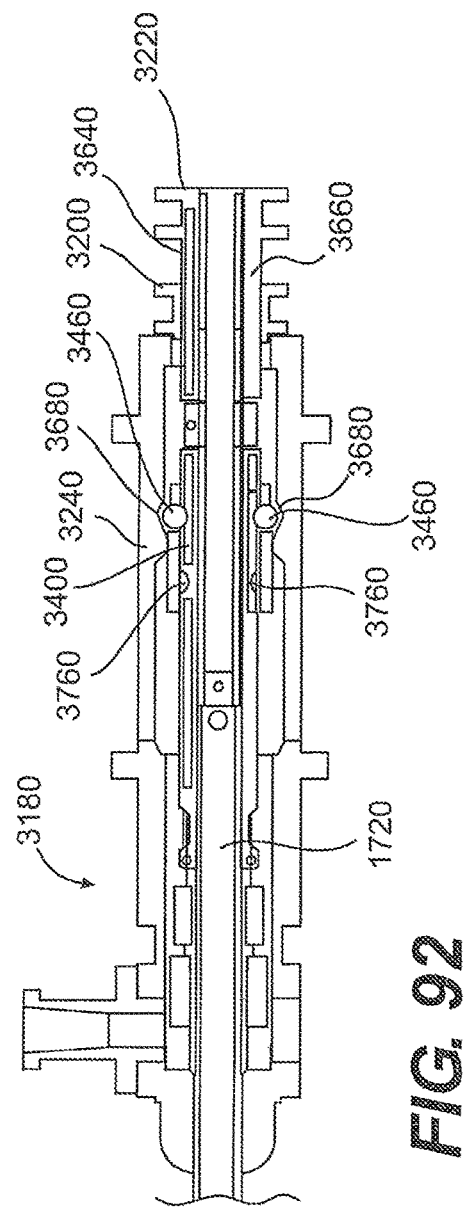
FIG. 92 shows a cross-section of the transmission where the clip is latched.

FIG. 92 is a side sectional view of transmission 3180 and the clip 100 (not shown) is closed or latched. The center spindle 3640 and 3660 continues to advance. Connecting pins 3460 are located in the pockets 3680 in the outer shell 3240 and 3260. The catch puncher latch 3400 stops. The punch 1720 continues forward with the center spindle 3640 and 3660 until the clip 100 (not shown) is latched, everything returns in reverse order after latching.

Figure 93:
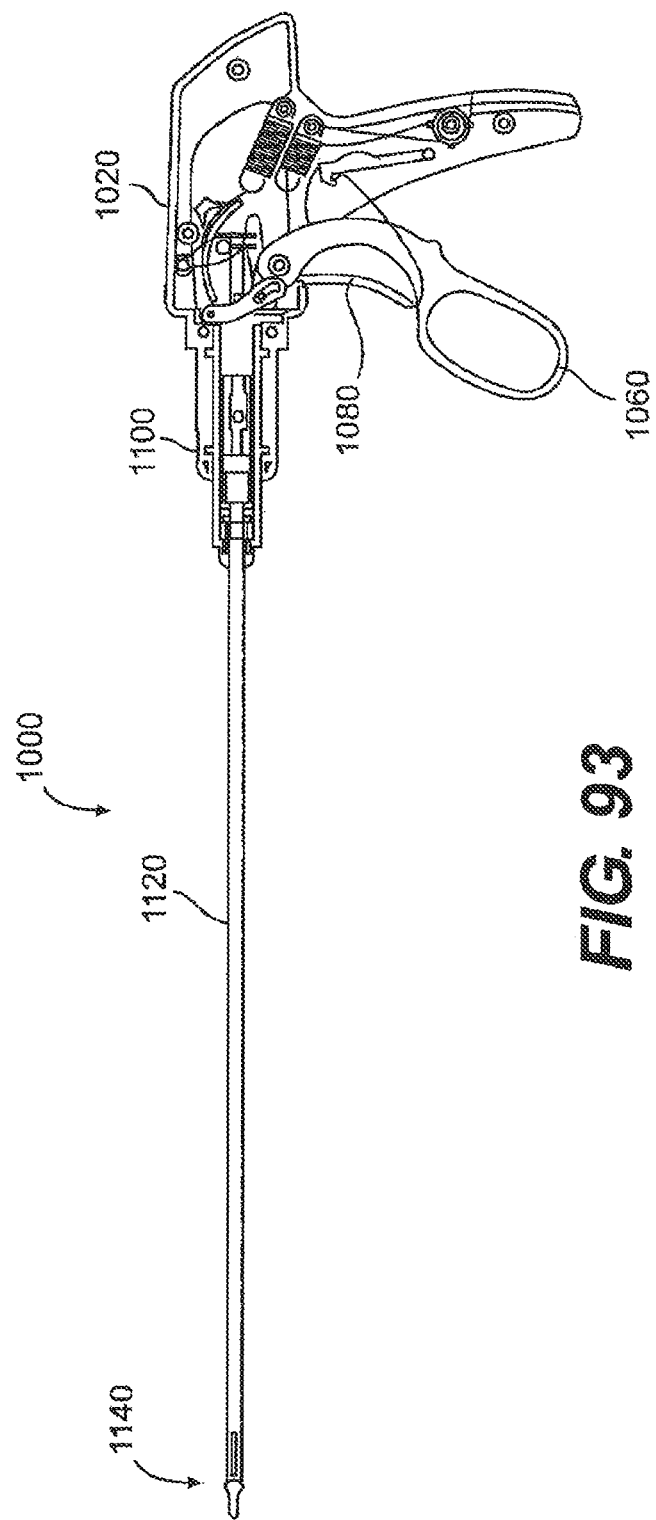
FIGS. 93-97 show side views of an applier in some FIGS. internal components are exposed and illustrated.

FIG. 93 is a side view with part of the housing removed of the applier 1000. The jaws 1140 are shown on the shaft 1120. The shaft 1120 extends from the transmission housing 1100. Part of the housing 1020 is open to show interior elements. The ligate trigger 1080 is shown as well as the jaw trigger 1060. The applier 1000 as shown in FIG. 93, shows the applier 1000 ready to receive a clip 100 as shown.

Figure 94:
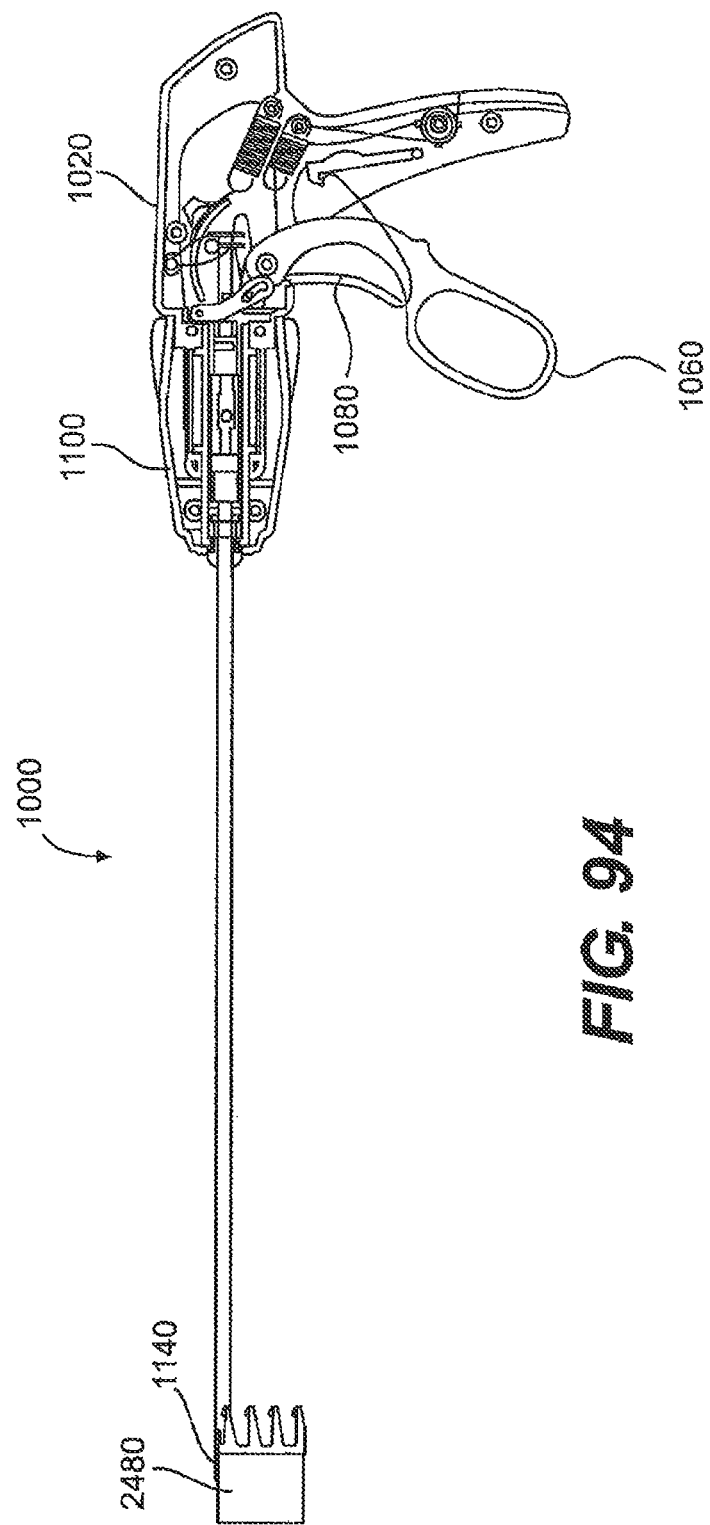

FIG. 94 is a side view of an applier 1000 with part of the transmission housing 1100 and clam shell housing 1120 removed to show interior elements. Applier 1000 is retrieving a clip 100 (not shown) from a cartridge 2480 into the jaws 1140 of the applier 1000. The ligate trigger 1080 is shown as well as the jaw trigger 1160. Position of the jaw trigger 1160 and the ligate trigger 1080 are shown when the applier 1000 is in a cartridge loading position.

Figure 95:
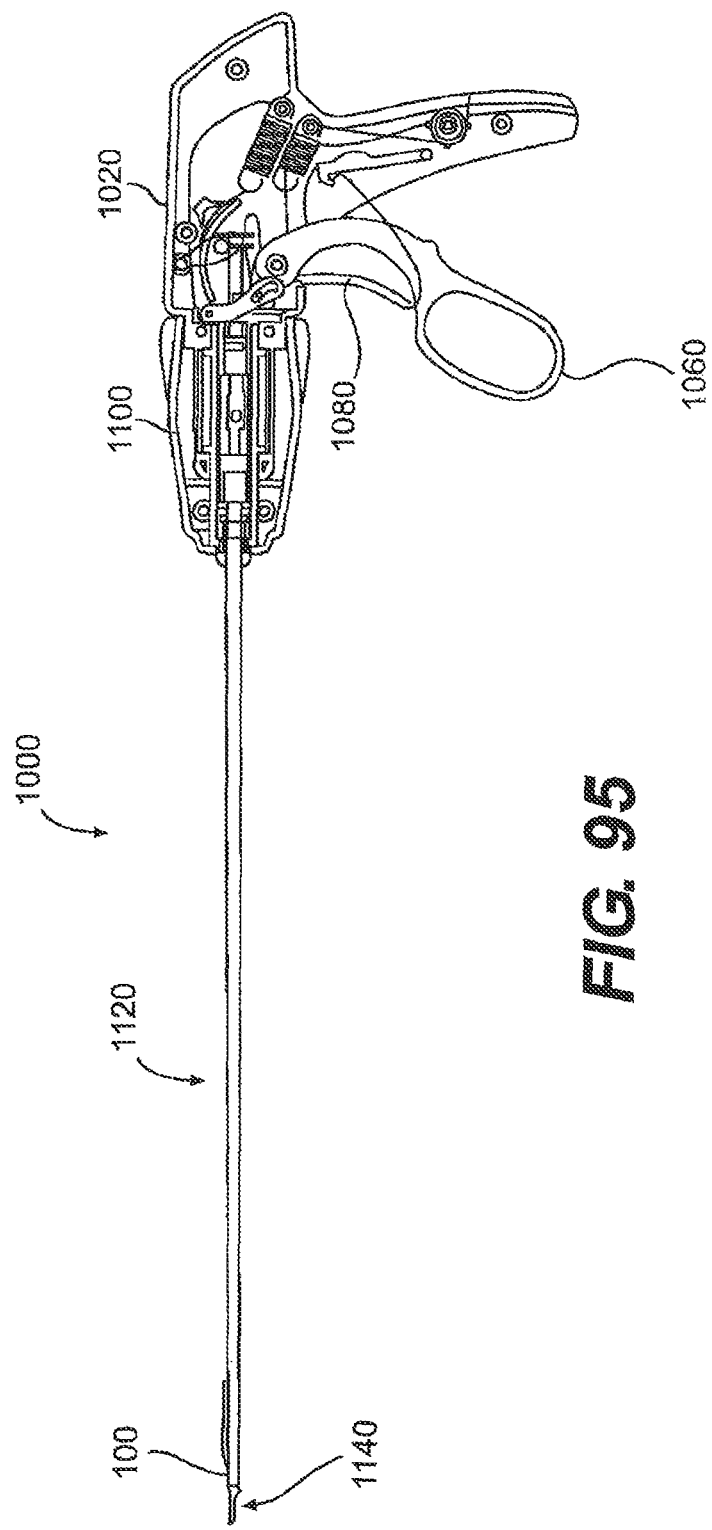

FIG. 95 is a side view of the applier 1000. The transmission housing 1100 is cut away and the clam shell housing 1020 is cut away to show positions of interior elements. Part of the jaws 1140 and the top part of the shaft 1120 are missing to better show interior elements. The positions of the ligate trigger 1080 and the jaw trigger 1060 are shown where the applier 1000 is ready to have the clip 100 to move forward into the jaws 1140.

Figure 96:
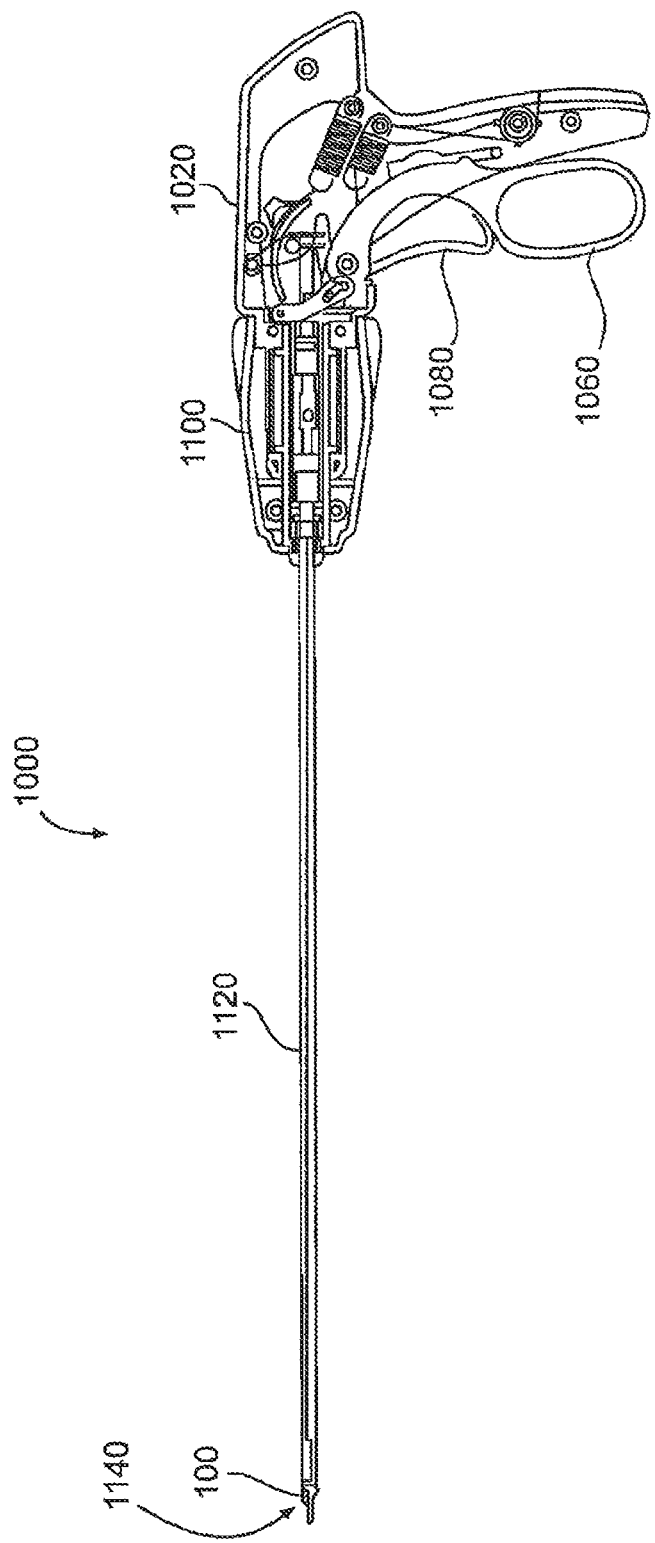

FIG. 96 illustrates an applier 1000 where part of the transmission housing 1100, clam shell housing 1020, the shaft 1120 and the jaws 1140 are missing. The ligate trigger 1080 and the jaw trigger 1060 are in a position for allowing the clip 100 to move forward.

Figure 97:
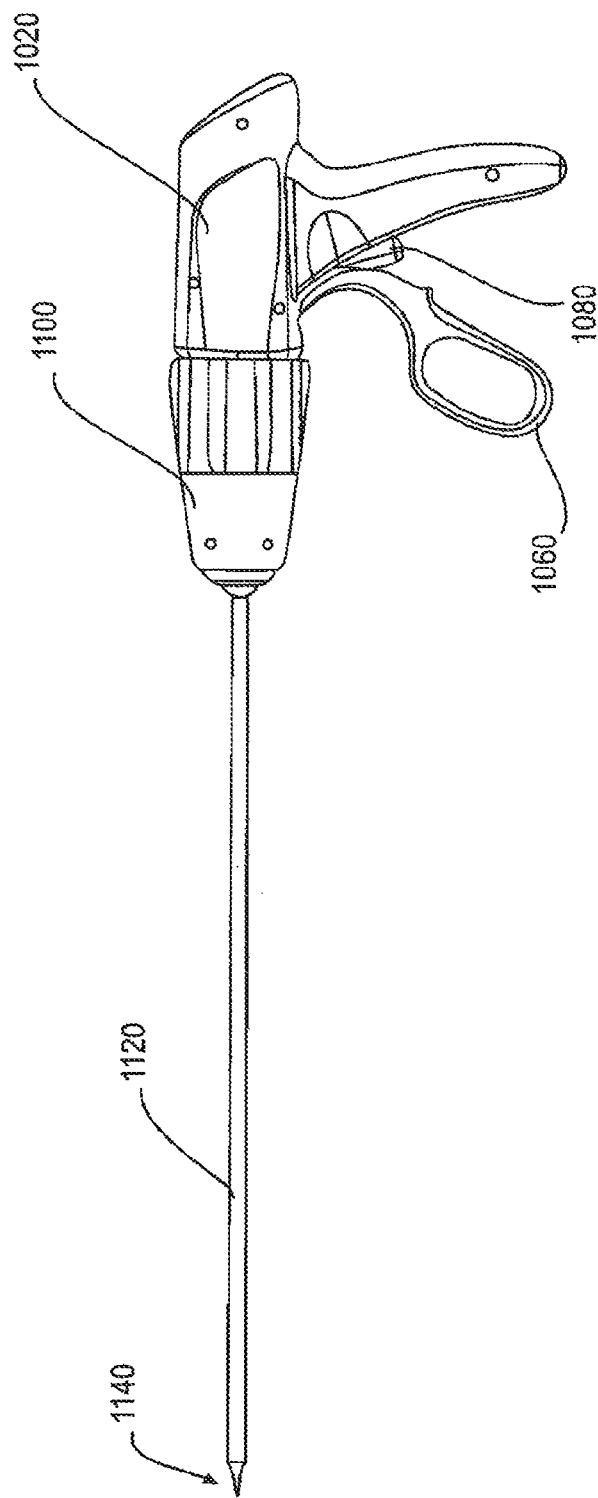

The applier 1000 shown in FIG. 97 shows an applier where the ligate trigger 1080 and the jaw actuator 1060 are in a position where the clip 100 (not shown) is to be latched. Transmission housing 1100 and the clam shell housing 1020 are shown intact.

Figure 98:
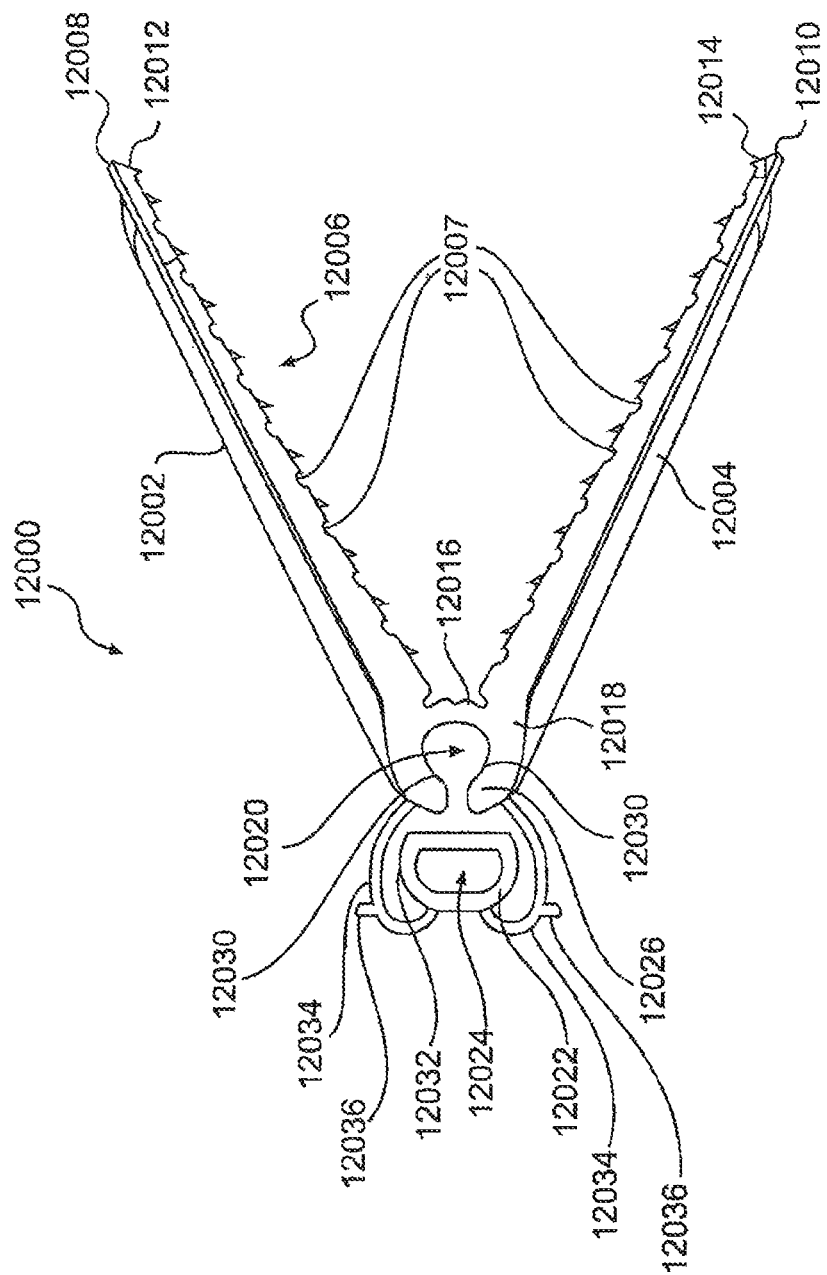
FIG. 98 is a side view of another clip used in accordance with an embodiment of the invention.

In another embodiment, a different clip 12000 and adapter 12040 is used. This clip 12000 and adapter 12040 is shown and described in FIGS. 98-122. FIG. 98 shows a side view of the clip 12000. The clip 12000 includes an upper leg 12002 and a lower leg 12004. Both legs 12002 and 12004 include teeth 12006 and grooves 12007. The upper leg 12002 includes an upper front end and 12008 in the lower leg 12004 includes a lower front and 12010. The upper front end 12008 includes an upper slanted edge 12012 and the lower front end 12010 includes a lower slanted edge 12014. The upper leg 12002 and the lower leg 12004 pivot about a hinge portion 12016 which is part of a body portion 12018.

The body portion 12018 includes a locking void 12020. The clip 12000 is locked by moving a buttress 12022 into the locking void 12020. The buttress 12022 includes a buttress void 12024. The body portion 12018 includes locking wings 12026. The locking wings 12026 help retain the buttress 12022 into the locking void 12020 when the clip 12000 is in a locking position. The buttress void 12024 includes locking interior surfaces 12030. The buttress 12022 includes locking exterior surfaces 12032. When the buttress 12022 is in the buttress void 12024 the locking interior surfaces 12030 and the locking exterior surfaces 12032 will be in contact with each other.

The buttress 12022 is attached to the body portion 12018 the connectors 12034. The connectors 12034 are resilient and will flex to permit the movement of the buttress 12022 with respect to the body portion 12018. The connectors 12034 are equipped with projections 12036. The projections 12036 are useful when the clips 12000 are arranged in an automatic applier in a nose to tail fashion. In such an instance, the upper front end 12008 and lower front end 12010 of a clip 12000 behind a first clip 12000 will engage the projections 12036 of the clip 12000 in front.

Figure 99:
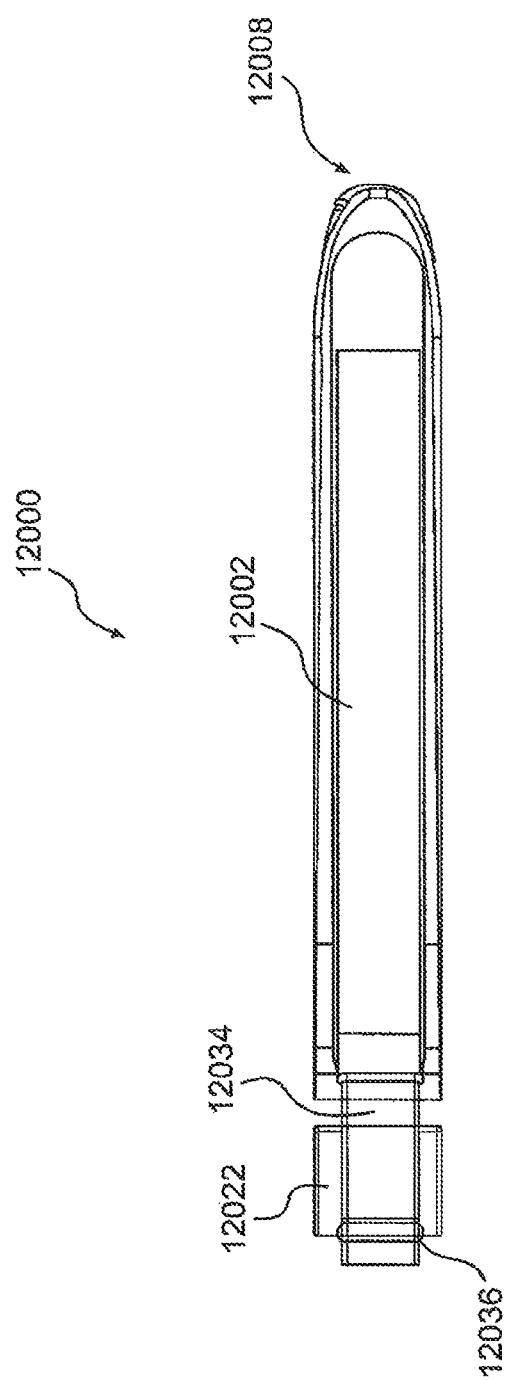
FIG. 99 is a top view of a clip illustrated in FIG. 98.

FIG. 99 illustrates a top view of the clip 12000. The upper leg 12002 and the upper front end 12008 are visible. The connector 12034 connecting the buttress 12022 and having the projection 12036 is also shown in FIG. 99.

Figure 100:
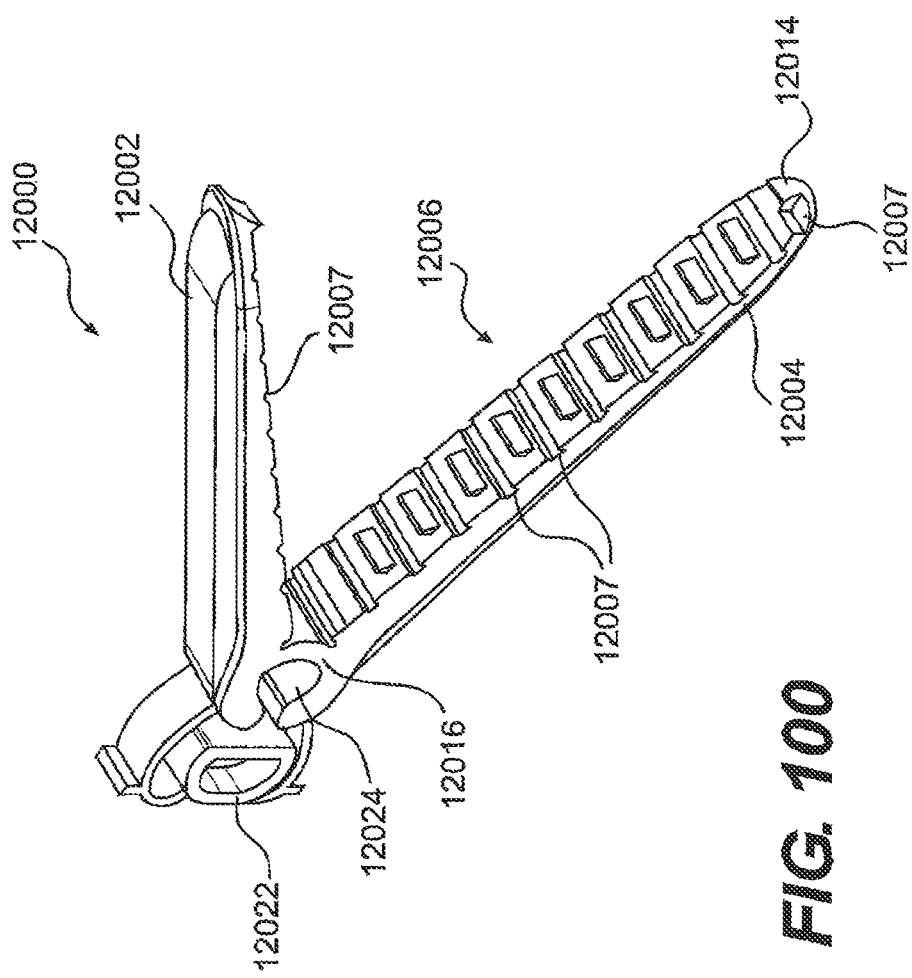
FIG. 100 is a isometric view of the clip illustrated in FIG. 98.

FIG. 100 illustrates an isometric view of the clip 12000. The upper leg 12002, the lower leg 12004, the grooves 12007, and teeth 12006 are visible. The lower slanted edge 12014 can also be seen. The hinge portion 12016, the buttress void 12024, and the buttress 12022 are also visible in the isometric view shown in FIG. 100.

Figure 101:
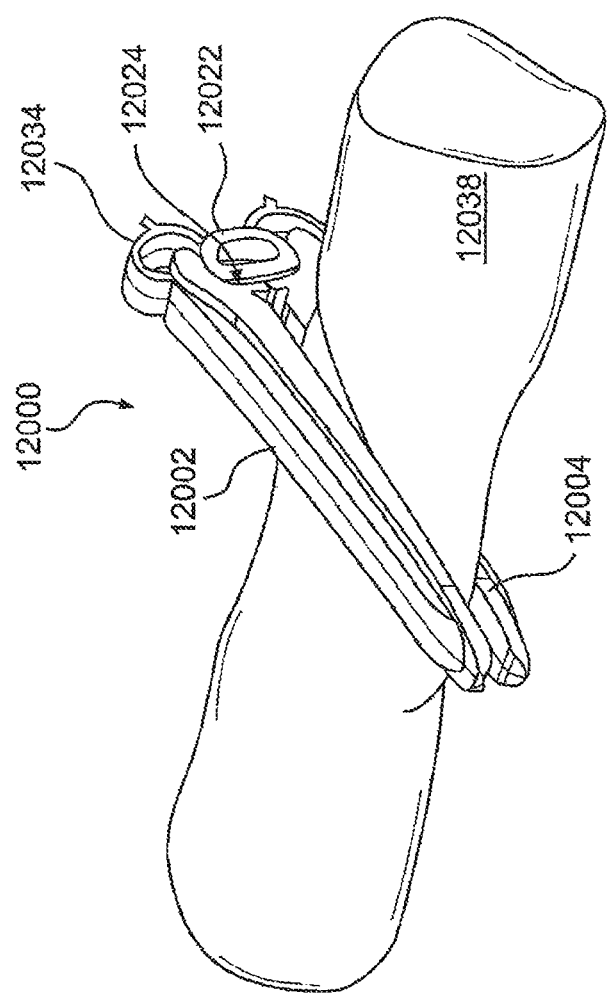
FIG. 101 is an isometric view of a clip applied onto tissue or a blood vessel.
Figure 102:
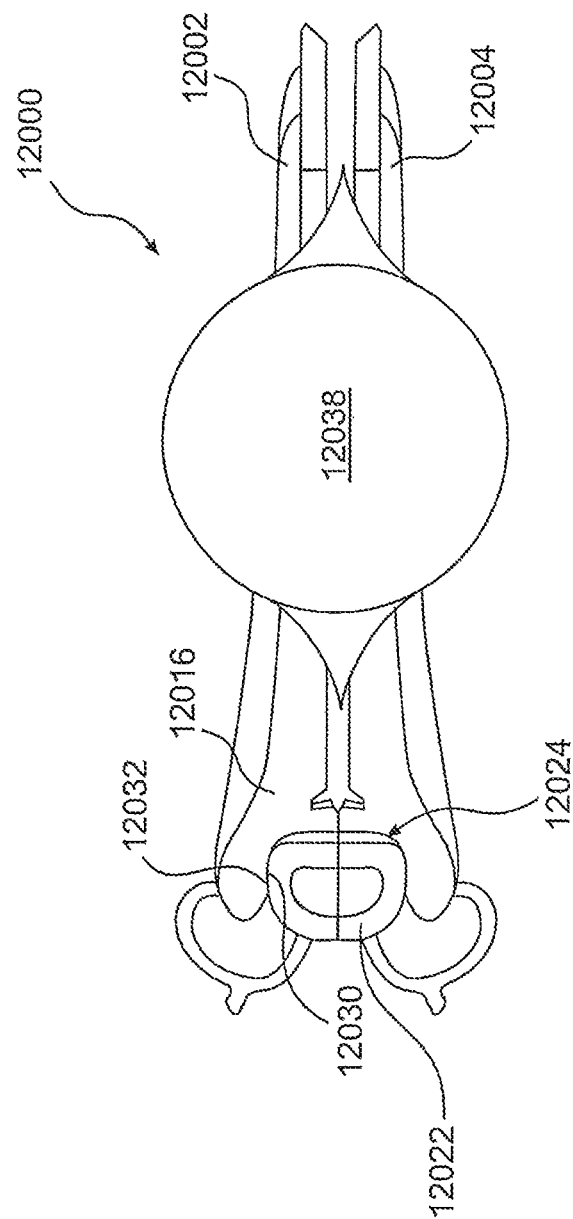
FIG. 102 is a side view of a clip locked onto a tissue or blood vessel.

FIGS. 101 and 102 illustrate the clip 12000 clamping onto a vessel 12038. The grooves and teeth are not shown and are removed for clarity in FIGS. 101 and 102. The vessel 12038 is clamped between the upper leg 12002 and the lower leg 12004. The buttress 12022 has been moved into the buttress avoid 12024 causing the locking interior surfaces 12030 and a locking exterior surfaces 12032 to be in contact with each other. Movement of the buttress 12022 into the buttress avoid 12024 has caused the upper leg 12002 and the lower leg 12004 to be locked in a closed position. It will be appreciated that closing of the clip 12000 will cause the hinge portion 12016 to rotate thereby enlarging the buttress avoid 12024 and allowing the buttress 12022 to be pushed or moved into the buttress void 12024 thereby locking the clip 12000 in the closed position. Once the clip 12000 is in the closed position the vessel 12028 is clamped.

Figure 103:
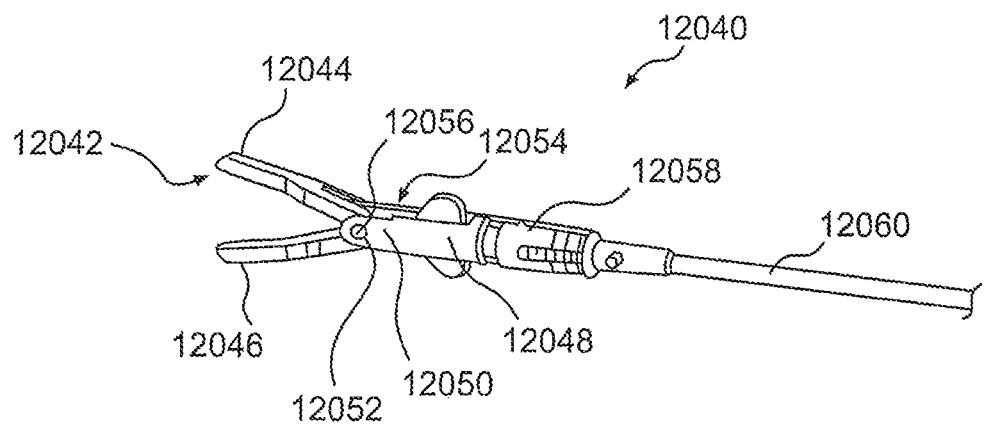
FIG. 103 is a isometric view of a distal end of applier.

A manual applier 12040 may be used with the clip 12000 shown and described in FIGS. 98 through 102. A partial isometric view of a manual applier 12040 that may be used with the clip 12000 is shown in FIG. 103. The manual applier 12040 includes a pair of jaws 12042. The jaws 12042 may include an upper jaw 12044 and a lower jaw 12046. The jaws 12042 may be pivotally attached to a distal locking clevis tube 12048. The distal locking clevis tube 12048 may include a boss 12050 having a hole 12052. The distal locking clevis tube 12048 may also include a slot 12054 through which part of the jaws 12042 extend. The jaws 12042 may attached to the distal locking clevis tube 12048 via a pivot rivet 12056 extending through the hole 12052 in the distal locking clevis tube 12048 and the jaws 12042. Behind distal locking clevis tube 12048 is a proximal locking clevis tube 12058 and an actuation shaft 12108 (See FIG. 117).

Figure 104:
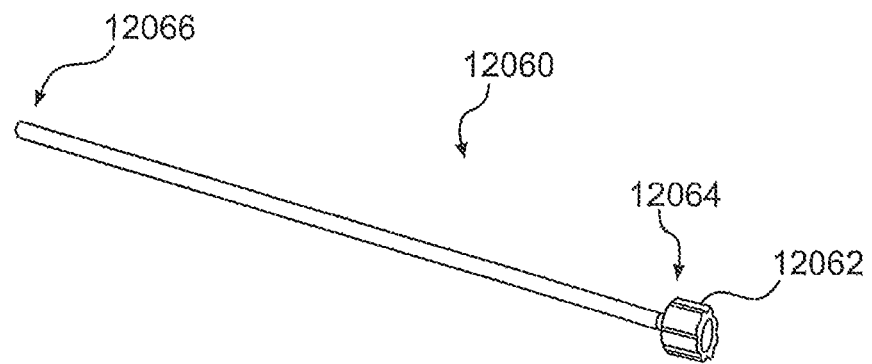
FIG. 104 is a isometric view of a shaft assembly.

FIG. 104 illustrates a shaft tube assembly 12060. The shaft tube assembly 12060 includes a handle interface 12062 located at the proximal end 12064 of the shaft tube assembly 12060. The shaft tube assembly 12060 also includes a distal end 12066. In some embodiments, the shaft tube assembly 12060 fits over the actuation shaft 12108 (hidden in FIG. 117) and part of the proximal locking clevis tube 12058. The shaft tube assembly 12060 provides a housing for the actuation shaft 12108. The shaft tube assembly 12060 is removed in the other figures to show the internal comport parts of the manual applier 2040.

Figure 105:
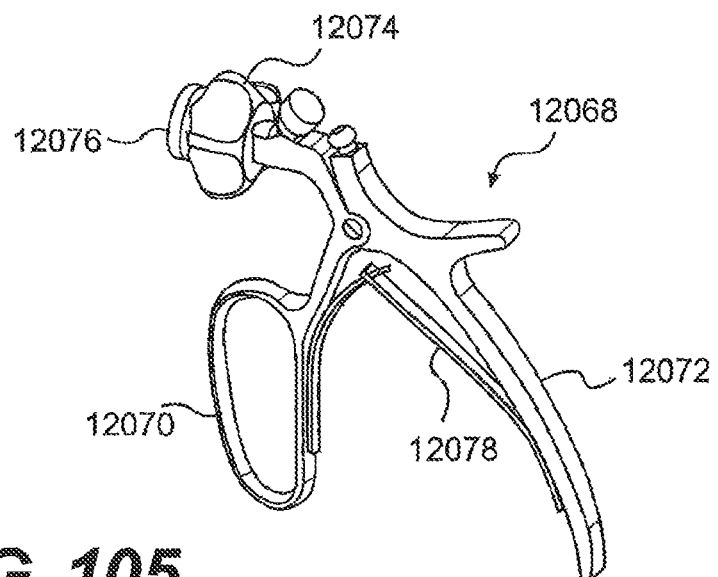
FIG. 105 is a isometric view of a handle assembly.

FIG. 105 is an isometric view of a handle assembly 12068. In some embodiments of the invention, the handle assembly to 12068 may be standard off-the-shelf feature. For example, the handle 12068 sold as the Hem-o-loc® handle identified as number 544965P may be used. The handle 12068 may include a pivoting lever 12070 attached to the handle 12072. A rotator 12074 is configured to allow an operator to rotate the rotator 12074 and thereby rotate also the shaft tube assembly 12060 (See FIG. 103) and jaws 12042 along with the components located at the distal end of the applier 12040. This rotation capability allows a user to orient the jaws 12042 to a desired angular rotation. The handle 12068 also includes an actuation shaft interface 12076. It is the actuation shaft interface 12076 that communicates with the handle interface 12062 on the shaft tube assembly 12060 to cause the rotation of the shaft tube assembly 12060, its internal components, the jaws 12042, and other complements located at the distal end of the applier 12040 when the rotator 12074 is rotated by a user. The lever 12070 is biased away from the handle 12072 by the leaf spring assembly 12078.

Figure 106:
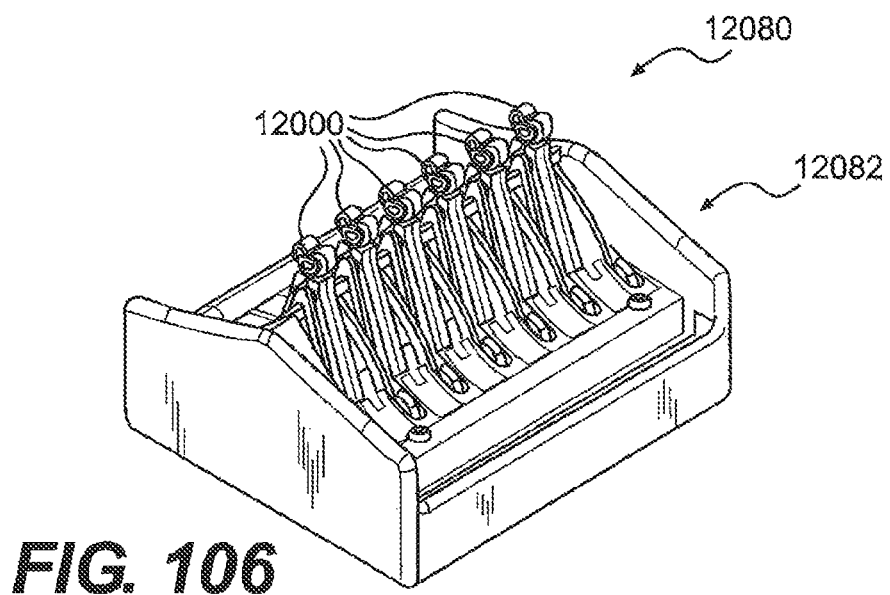
FIG. 106 is an isometric view of a clip cartridge.

According to some embodiments, the applier 12040 is capable of applying only a single clip 12000 at a time. In order to load a clip 12000 into the jaws 12042, a clip cartridge 12080 as shown in FIG. 106 may be used. The clip cartridge 12080 may include several clips 12000 located in clip retainers 12082 within the clip cartridge 12080. To obtain a clip 12000 from the clip cartridge 12080, the jaws 12042 are placed over a clip 12000 and then the jaws 12042 are removed from the clip cartridge 12080 thereby causing the clip 12000 to be removed from the clip retainer 12082 and stay in the jaws 12042.

Figure 107:
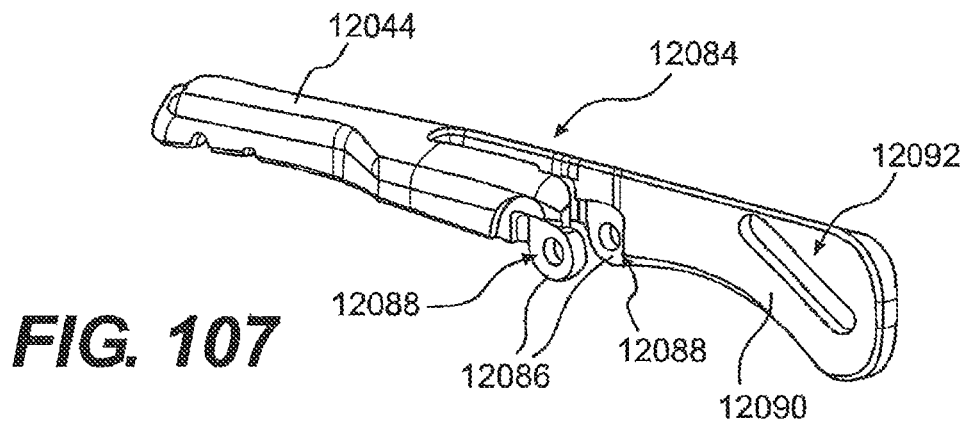
FIG. 107 is an isometric view of a jaw.

FIGS. 107 through 114 illustrate single components of the manual applier 12040. FIGS. 115 through 122 illustrate how these components are assembled together. Each will be discussed in turn. FIG. 107 illustrates an upper jaw 12044. In some embodiments, the upper jaw 12044 and the lower jaw 12046 are the same part just installed in opposite orientations. The jaw 12044 includes a slot 12084. The jaw 12044 also includes bosses 12086 which define holes 12088. The rear of the jaw 12044 includes an actuation body 12090 which defines an actuation slot 12092. It is by moving a part through the actuation slot 12092, which will be discussed in further detail below that the jaw 12044 will pivot about a pivot rivet 12056 that extends through the holes 12088 in the bosses 12086.

Figure 108:
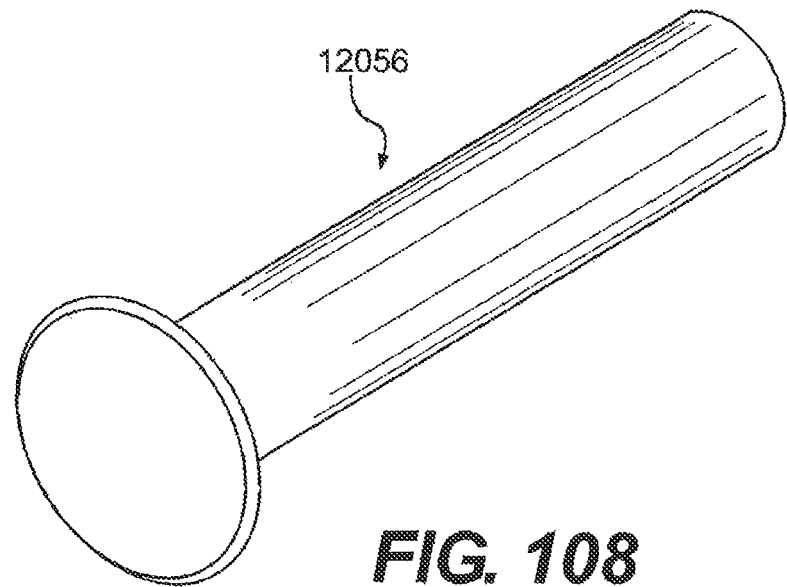
FIG. 108 is an isometric view of a pivot rivet.

FIG. 108 is an isometric view of the pivot rivet 12056 which, as shown in FIG. 103 extends through the hole 12052 in the boss 12050 of the distal locking clevis tube 12048. The pivot rivet 12056 also extends through the holes 12088 in the bosses 12086 in the jaw 12044 to pivotally connect the jaw 12044 to the distal locking clevis tube 12048. The pivot rivet 12056 will attach both the upper jaw 12044 and the lower jaw 12046 to the distal locking clevis tube 12048.

Figure 109:
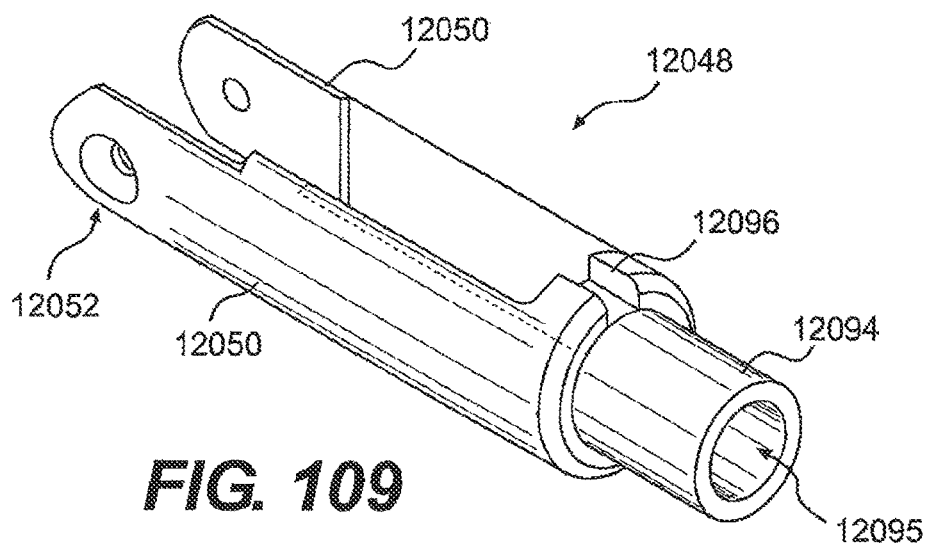
FIG. 109 is an isometric view of a distal locking clevis tube.

FIG. 109 is an isometric view of the distal locking clevis tube 12048. The distal locking clevis tube 12048 includes bosses 12050 defining holes 12052 a guiding slot 12096 and a narrow diameter portion 12094. The narrow diameter portion 12094 defines a hole 12095, or is another words, is hollow.

Figure 110:
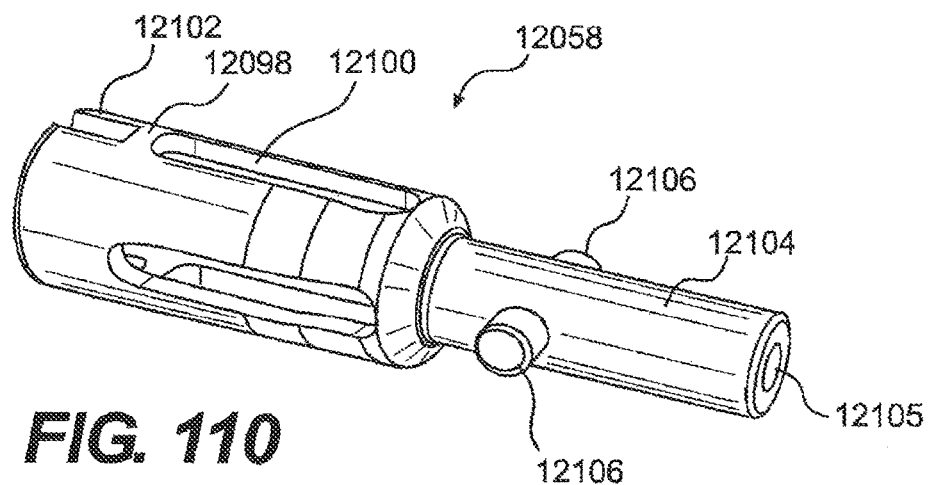
FIG. 110 is an isometric view of a proximal locking clevis tube.

FIG. 110 is an isometric view of the proximal locking clevis tube 12058. The proximal locking clevis tube 12058 includes a large diameter housing 12098 which has slits 12100 the large diameter housing 12098 also defines a guiding slot 12102. The large diameter housing 12098 is dimensioned to fit over and ride on the narrow diameter portion 12094 of the distal locking clevis tube 12048 as illustrated in FIG. 109. An illustration of the proximal locking clevis tube 12058 fit over the narrow diameter portion 12094 of the distal locking clevis tube 12048 will be described and illustrated in later figures described further below. The guiding slot 12102 on the proximal locking clevis tube 12058 will align with the guiding slot 12096 in the distal locking clevis tube 12048 when the proximal locking clevis tube 12058 is mounted onto the narrow diameter portion 12094 of the distal locking clevis tube 12048.

The proximal locking clevis tube 12058 also includes a narrow diameter portion 12104 which defines a hole 12105, or in other words, is hollow. The narrow diameter portion 12104 of the proximal locking clevis tube 12058 includes trunnions 12106. The trunnions 12106 are useful for attaching or locking the proximal locking clevis tube 12058 to the shaft tube assembly 12060 when the shaft tube assembly 12060 is fit over the narrow diameter portion 12104 of the distal locking clevis tube 12048. The trunnions 12106 fit into corresponding internal slots with in the shaft tube assembly 12060 to lock the shaft tube assembly 12060 to the proximal locking clevis tube 12058.

Figure 111:
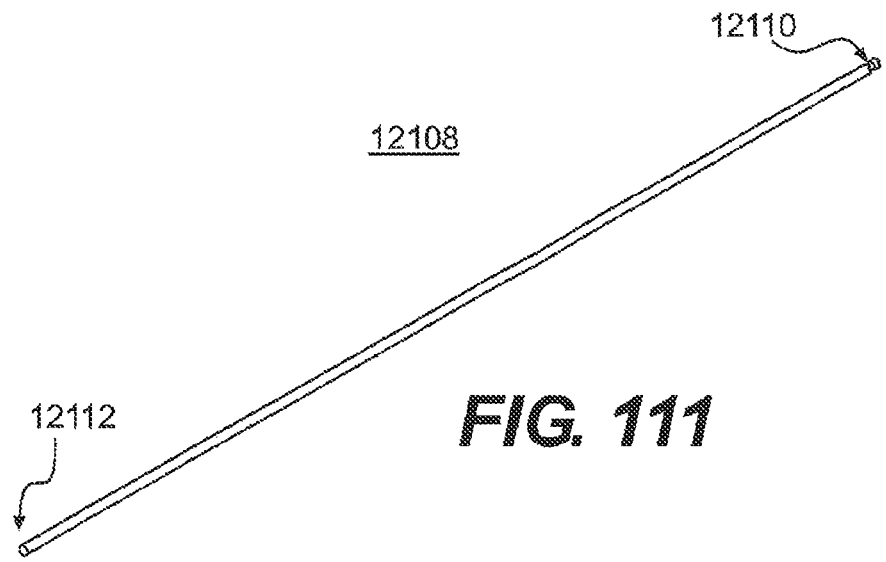
FIG. 111 is an isometric view of an actuation shaft.

FIG. 111 illustrates the actuation shaft 12108. The actuation shaft 12108 includes ends 12110 and 12112. The end 12110 interacts with the handle 12068 so the actuation of the lever 12070 on the handle 12068 causes the actuation shaft 12108 to move.

Figure 112:
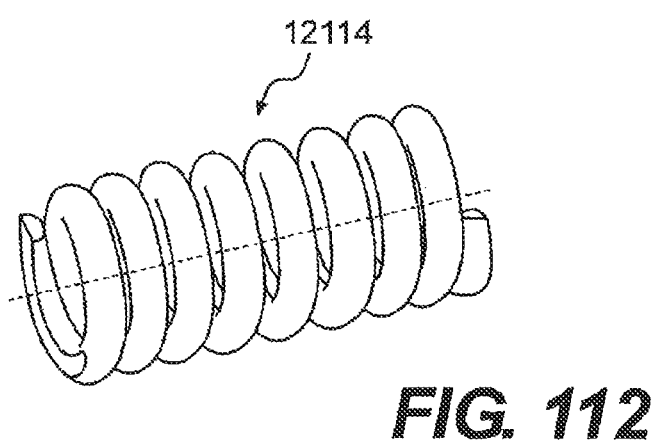
FIG. 112 is an isometric view of a spring.
Figure 113:
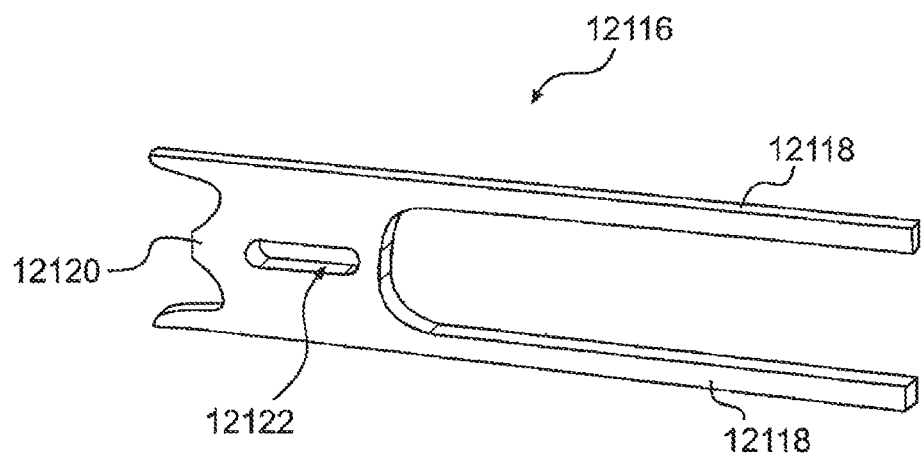
FIG. 113 is an isometric view of a clip lock actuator.
Figure 114:
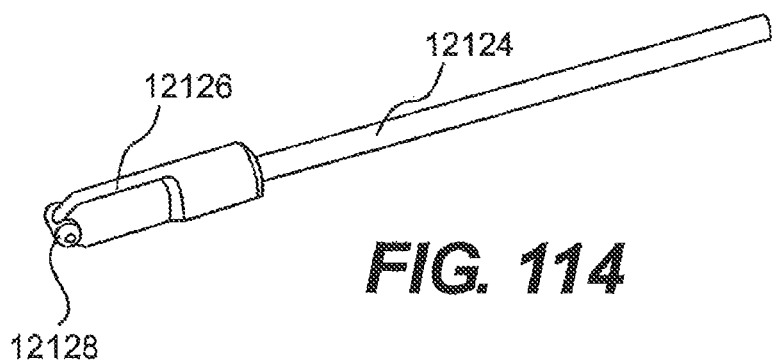
FIG. 114 is an isometric view of a distal pushrod.

FIG. 112 illustrates a spring 12114. The spring 12114 is used to bias the jaws 12042 in a distal position. This will be discussed further below. FIG. 113 illustrates a clip lock actuator 12116. The clip lock actuator 12116 includes legs 12118 and a locking projection 12120. The clip lock actuator 12116 also includes a slot 12122. FIG. 114 is a isometric view of a distal pushrod 12124. The distal pushrod 12124 includes a flat portion 12126 having projections 12128 located at one end. The projections 12128 are what ride with in the slot 12092 illustrated in the jaws 12044 of FIG. 107. By moving axially, the distal pushrod 12124 causes the jaws 12044 to open and close.

Figure 115:
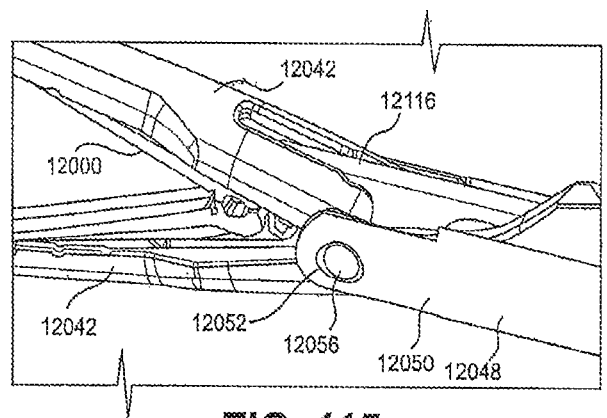
FIG. 115 is a partial isometric view of applier jaws.

FIGS. 115 through 122 are partial, isometric, assembly views of the parts described in FIGS. 104 through 114. FIG. 115 illustrates the clip 12000 contained within the jaws 12042. The distal locking clevis tube 12048 has the boss 12050 defining the hole 12052 through which the pivot rivet 12056 extends to provide a pivot shaft for the jaws 12042. The pivot rivet 12056 extends through the hole 12052 in the boss 12050, the holes 12088 in the jaws 12042 (as shown in FIG. 107) and through the slot 12122 in the clip lock actuator 12116 (shown in FIG. 113).

Figure 116:
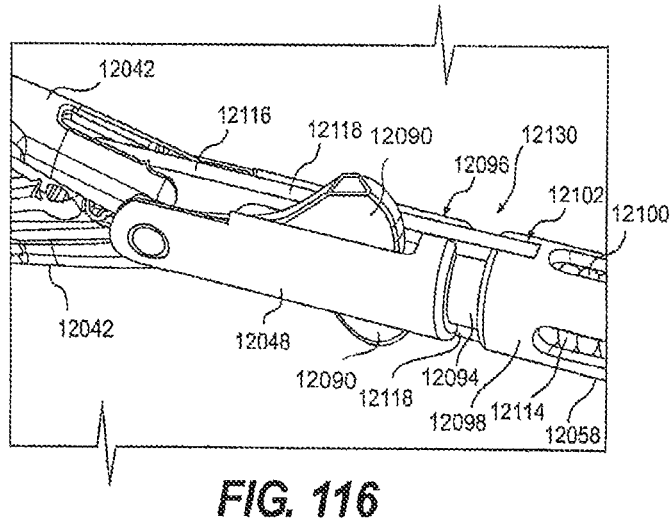
FIG. 116 is a partial isometric view of a distal portion of an applier.

FIG. 116 shows the jaws 12042 and a generally open position. Legs 12118 of the clip lock actuator 12116 are shown extending through the guiding slot 12096 on the distal locking clevis to 12048 and the guiding slot 12102 in the housing 12098 of the proximal locking clevis tube 12058. In some embodiments, the legs 12118 of the clip lock actuator 12116 are welded into the guiding slot 12102 of the proximal locking clevis tube 12058. The actuation bodies 12090 of the jaws 12042 extend through the distal locking clevis tube 12048. The spring 12114 is shown through the slits 12100 in the housing 12098 of the proximal locking clevis tube 12058. A relief 12130 is shown between the distal locking clevis tube 12048 and the housing 12098 of the proximal locking clevis tube 12058. The housing 12098 rides on the narrow diameter portion 12094 of the distal locking clevis tube 12048. The jaws 12042 are in the open position and are therefore in a distal position making the relief 12130 to be relatively large.

Figure 117:
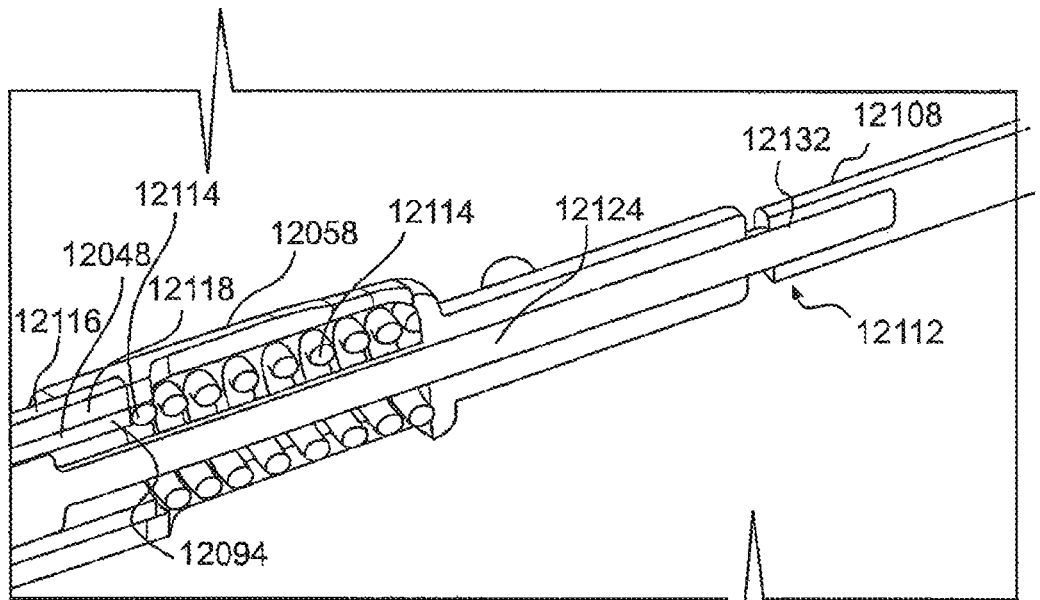
FIG. 117 is an isometric, cross-sectional, partial view of a portion of an applier.

FIG. 117 is a partial cross-sectional view illustrating the actuation shaft 12108 attached to the end 12112 of the distal pushrod 12124. The end 12112 of the distal pushrod 12124 is placed into the hole 12132 in the actuation shaft 12108. In some embodiments, the end 12112 of the distal pushrod 12124 is welded into the hole 12132 in the actuation shaft 12108. The distal pushrod 12124 extends through the spring 12114, proximal locking clevis tube 12058, the narrow diameter portion 12094 of the distal locking clevis tube 12048, and the legs 12118 of the clip lock actuator 12116. The spring 12114 urges the narrow diameter portion 12094 of the distal locking clevis tube 12048 to bias the distal locking clevis tube 12048 to a distal position.

Figure 118:
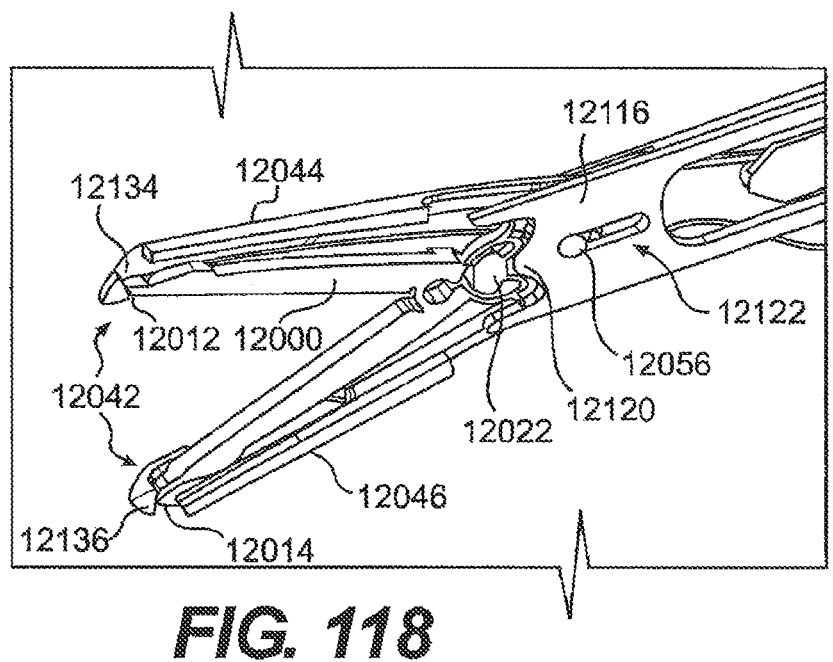
FIGS. 118-120 are partial cutaway views of the distal portion of an applier.

FIG. 118 shows the clip 12000 located in the jaws 12042 and an upper slanted edge 12012 is butted against an angled surface 12134 in the upper jaw 12044. Likewise a lower slanted edge 12014 of the clip 12000 is butted against an angled surface 12136 in the lower jaw 12046. In this manner, the clip 12000 is retained within the jaws 12042. A locking projection 12120 on the clip lock actuator 12116 is located near the buttress 12022. The pivot rivet 12056 is shown to be located in the slot 12122 within the clip lock actuator 12116.

Figure 119:
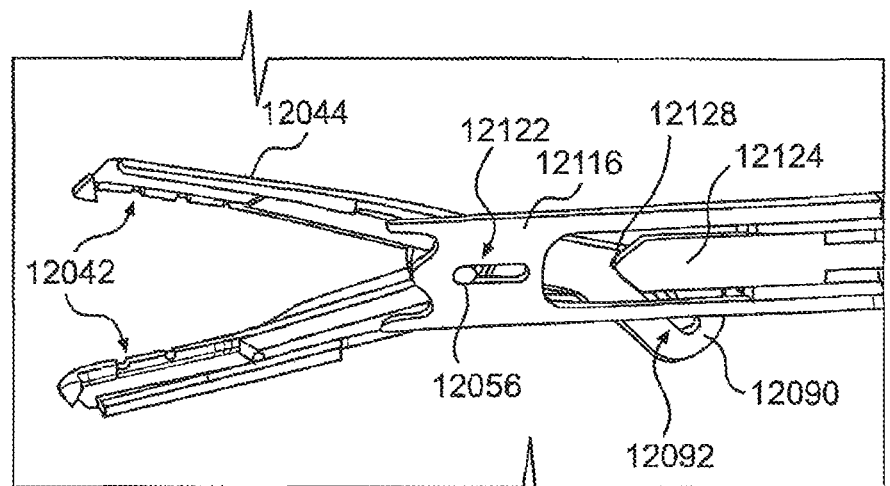

FIG. 119 illustrates a partial cross-sectional view with some of the parts removed for clarity. The jaws 12042 are in an open position. The pivot rivet 12056 is located in the slot 12122 within the clip lock actuator 12116. The distal pushrod 12124 is shown in cross-section so the front portion is removed. However, the back projection 12128 of the distal pushrod 12124 is located in the actuation slot 12092 in the actuation body 12090 of the jaw 12044. It will be appreciated that rearward or proximal movement of the distal pushrod 12124 will cause the projection 12128 to slide through the slot 12092 causing the jaw 12044 to move to a closed position. Once the projection 12128 reaches the end of the slot 12092 and the distal pushrod 12124 still continues to move rearward or in a distal direction, the jaws 12042 will then be moved also in the distal direction.

Figure 120:
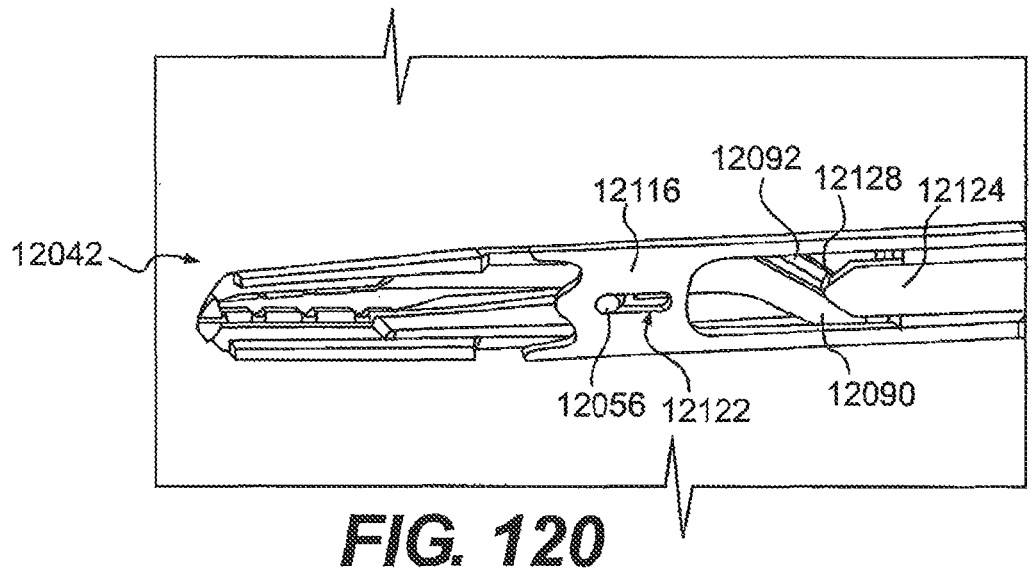

FIG. 120 shows the jaws 12042 in a closed position. The projection 12128 on the distal pushrod 12124 has moved to the end of the slot 12092. The pivot rivet 12056 is shown residing in the slot 12122 of the clip lock actuator 12116.

Figure 121:
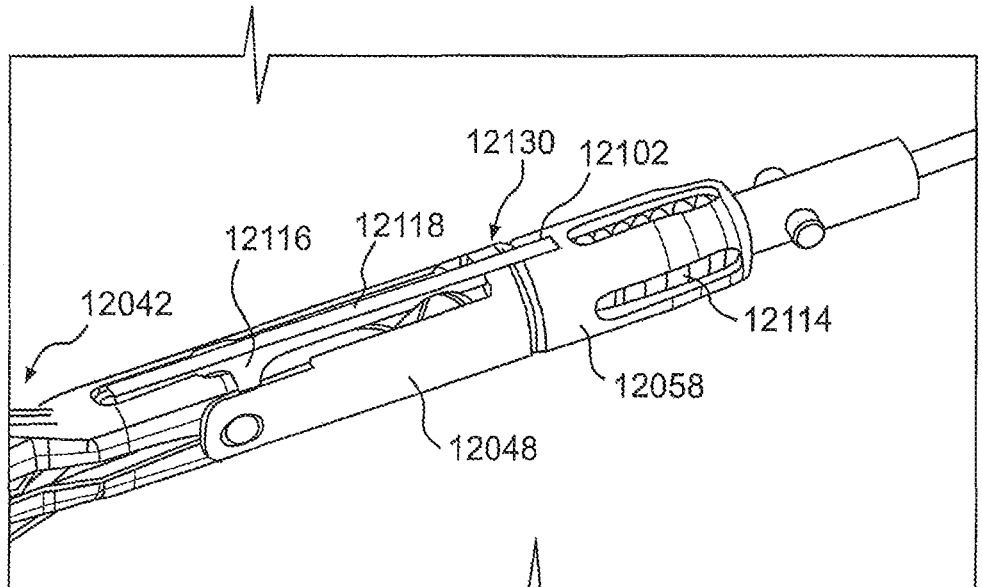
FIG. 121 is a partial distal view of a midsection of an applier.

FIG. 121 illustrates additional features where the jaws 12042 are in the closed position as shown in FIG. 120. The clip lock actuator 12116 and its legs 12118 are shown in the distal locking clevis tube 12048. The spring 12114 has become compressed within the proximal locking clevis tube 12058. The compression of the spring 12114 was caused by movement of the jaws 12042 and the distal locking clevis tube 12048 to the rearward or proximal position. The relief 12130 between the distal locking clevis tube 12048 and the proximal locking clevis tube 12058 has shrunk drastically. In some embodiments, the relief 12130 may disappear completely.

Figure 122:
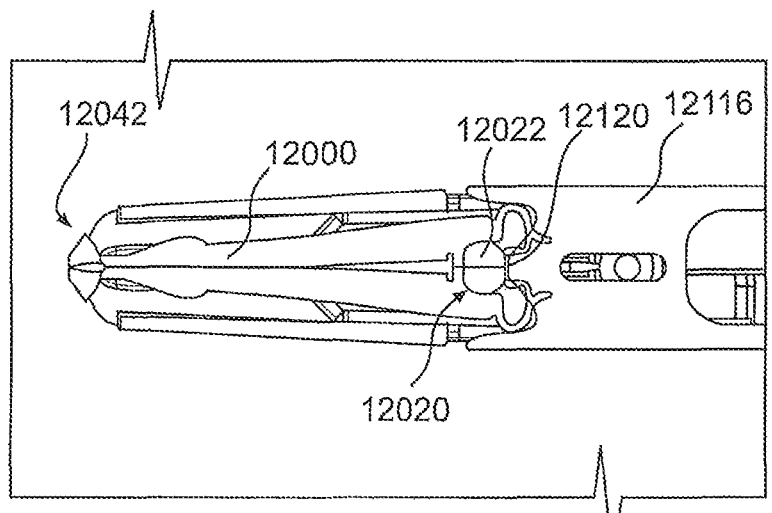

FIG. 122 has some of the parts removed for clarity. The jaws 12042 and clip 12000 are in the closed position. The jaws 12042 have moved to a distal position causing the buttress 12022 to contact the locking projection 12120 on the clip lock actuator 12116. Not only has the buttress 12022 contacted the projection 12120 but continued proximal movement has caused the buttress 12122 to move into the locking void 12020 thereby locking the clip 12000 in the closed position. In this manner, the clip 12000 is closed and locked.

Actuation of the jaws 12042 is accomplished by the proximal movement or pulling on the actuation shaft 12108 (see FIG. 117). Proximal movement of the actuation shaft 12108 can be accomplished by actuating a handle assembly 12068 (see FIG. 105) or by any other means. For example, the actuation shaft 12108 may be attached to a robot or any other suitable instrument. Because the actuation shaft 12108 is positively connected to the distal pushrod 12124 (see FIG. 119), proximally pulling on the actuation shaft 12108 will cause proximal movement of the distal pushrod 12124. Distal movement of the distal pushrod 12124 will cause the projections 12128 (see FIG. 119) to slide through the actuation slot 12092 in the jaws 12042.

Proximal movement of the projections 12128 will cause the jaws 12042 to close. Once the jaws 12042 are closed, continued proximal movement of the distal pushrod 12124 will cause the jaws 12042 to move distally. Proximal movement of the distal pushrod 12124 will cause the jaws 12042 to move proximally and continued proximal movement of the distal pushrod 12124 will cause the jaws to open. In some embodiments of the invention, the proximal movement of the distal pushrod 12124 is provided by the spring 12114.

Figure 123:
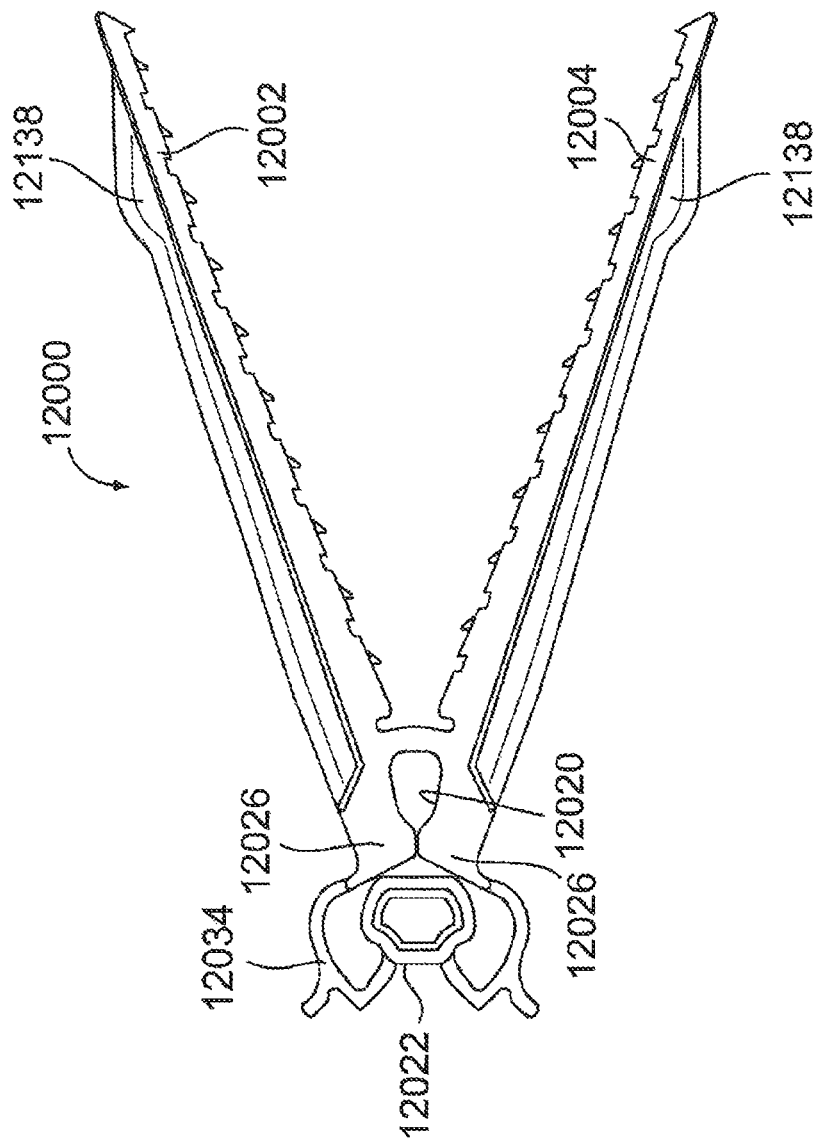
Figure 124:
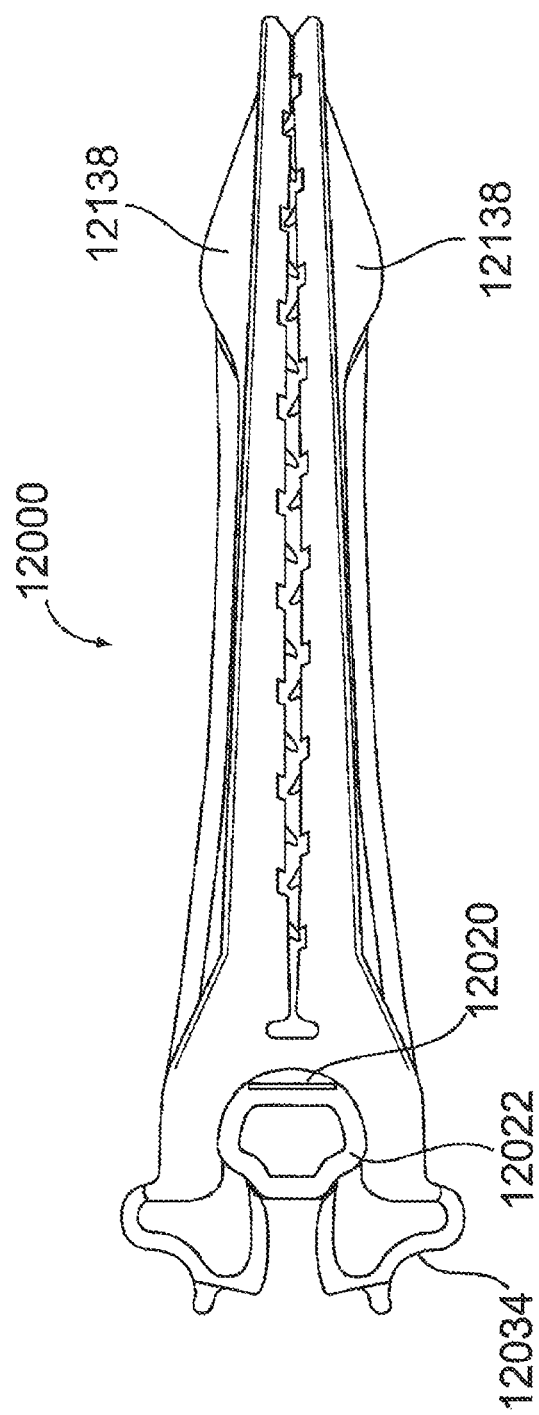
Figure 125:
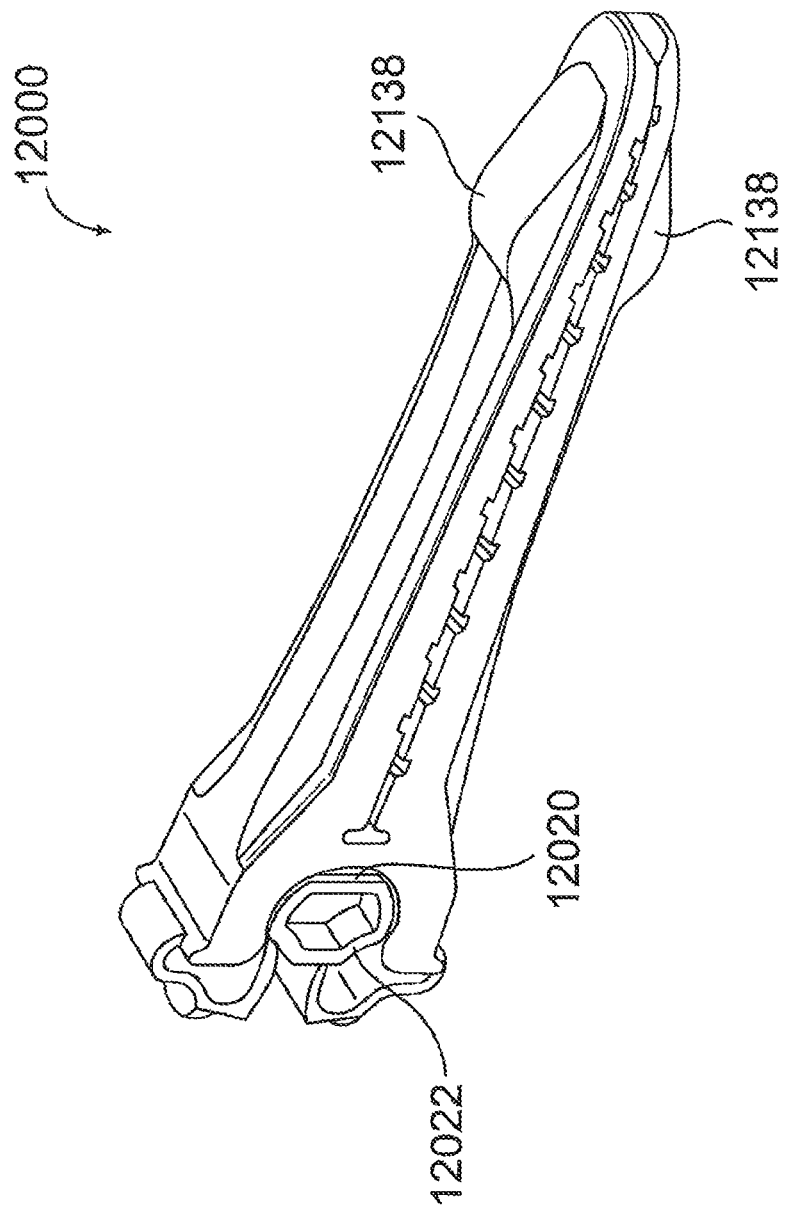

FIGS. 123-123 illustrate another clip 12000 that may be used in some embodiments of the invention. The clip 12000 shown in FIGS. 123-125 is similar to the clip illustrated in FIGS. 98-102. Differences between the clip 2000 shown in FIGS. 123-125 include the buttress 12022 having a different exterior geometry. The buttress 12022 is attached the connectors 12034 which, in turn, are connected to the locking wings 12026 of the clip 12000. The locking wings 12026 have a slightly different geometry as the clips 12000 shown earlier figures, but are shaped to correspond to the exterior geometry of the buttress 12022. The different exterior geometry of the buttress 12022 provides desired locking and unlocking characteristics for facilitating insertion or removal of the buttress 12022 from the locking void 12020. The clip 12000 also has bulges 12138 mounted on the upper leg 12002 and the rear bottom leg 12004. In some embodiments, the bulges 12138 assist in the retention and removal of the clip 12000 in the jaws 12042 of the applier 12040. In other embodiments of the invention, appliers 1000 can be used with various shaped clips and are not limited to the various clips described herein. For example, other clips are shown and described in the application titled "Narrow Profile Surgical Ligation Clip" filed Sep. 14, 2012 and identified as U.S. patent application Ser. No. 13/616,120 which is incorporated by reference in its entirety herein.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention. All ranges cited herein specifically incorporate all values and sub-ranges within the cited range.

What is claimed is:

1. A method of applying a clip having a pair of legs onto a vessel, the method comprising:
retaining the clip in a pair of jaws through engagement between an inclined surface on a distal portion of each leg of the clip and an inclined surface of each jaw;
moving a distal pushrod proximally to slide a projection along a slot in at least one of the jaws and to rotate the at least one of the jaws to a closed position;
moving the legs of the clip by closing the jaws;
moving the at least one of the jaws proximally by urging the projection against an end of the slot; and
moving a buttress on the clip to a locking position with a clip lock actuator as the at least one of the jaws continues to move proximally.

2. The method of claim 1, further comprising biasing the at least one of the jaws to a distal position with a spring.

3. The method of claim 1, further comprising actuating a pivotal handle to move the distal pushrod proximally.

4. The method of claim 1, further comprising limiting an amount of closing pressure that can be exerted by closing the jaws.

5. The method of claim 1, wherein moving the distal pushrod proximally includes sliding the projection through a slot in the clip lock actuator.

6. The method of claim 1, wherein moving the buttress includes moving the buttress into a void of the clip.

7. The method of claim 1, wherein the buttress is integrally joined to the clip through at least one connector.

8. A method of applying a clip having a pair of legs, the method comprising:
retaining the clip in a pair of jaws through engagement with a distal portion of each leg of the clip;
moving a distal pushrod proximally to slide a projection along a slot in at least one of the jaws and to rotate the at least one of the jaws to a closed position;
moving the legs of the clip by closing the jaws;
moving the at least one of the jaws proximally by urging the projection against an end of the slot; and
moving a buttress with a clip lock actuator to a locking position with respect to the clip.

9. The method of claim 8, further comprising biasing the at least one of the jaws to a distal position with a spring.

10. The method of claim 8, further comprising actuating a pivotal handle to move the distal pushrod proximally.

11. The method of claim 8, further comprising limiting an amount of closing pressure that can be exerted by closing the jaws.

12. The method of claim 8, wherein moving the distal pushrod proximally includes sliding the projection through a slot in the clip lock actuator.

13. The method of claim 8, wherein moving the buttress includes moving the buttress into a void of the clip.

14. The method of claim 8, wherein the buttress is integrally joined to the clip through at least one connector.

* * * * *